US008014000B2

(12) United States Patent  (10) Patent No.: US 8,014,000 B2
Harrison  (45) Date of Patent: *Sep. 6, 2011

(54) BROAD BAND REFERENCING REFLECTOMETER

(75) Inventor: Dale A. Harrison, Austin, TX (US)

(73) Assignee: Jordan Valley Semiconductors Ltd., Migdal Haemek (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/590,151

(22) Filed: Nov. 3, 2009

(65) Prior Publication Data

US 2010/0051822 A1  Mar. 4, 2010

Related U.S. Application Data

(63) Continuation of application No. 12/231,350, filed on Sep. 2, 2008, now abandoned, which is a continuation of application No. 11/517,894, filed on Sep. 8, 2006, now Pat. No. 7,446,876, which is a continuation of application No. 10/909,126, filed on Jul. 30, 2004, now Pat. No. 7,126,131, which is a continuation-in-part of application No. 10/669,030, filed on Sep. 23, 2003, now Pat. No. 7,026,626, said application No. 10/909,126 is a continuation-in-part of application No. 10/668,642, filed on Sep. 23, 2003, now Pat. No. 7,067,818, said application No. 10/909,126 is a continuation-in-part of application No. 10/668,644, filed on Sep. 23, 2003, now Pat. No. 7,394,551.

(60) Provisional application No. 60/440,434, filed on Jan. 16, 2003, provisional application No. 60/440,435, filed on Jan. 16, 2003, provisional application No. 60/440,443, filed on Jan. 16, 2003.

(51) Int. Cl.
*G01N 21/55* (2006.01)

(52) U.S. Cl. ........ 356/445; 356/328; 250/372; 250/339; 250/2

(58) Field of Classification Search .................. 356/445, 356/328; 250/372, 339, 2
See application file for complete search history.

(56) References Cited

U.S. PATENT DOCUMENTS 3,091,154 A  5/1963 Hall
(Continued)

FOREIGN PATENT DOCUMENTS

CN  99254233.2  11/1999
(Continued)

OTHER PUBLICATIONS

U.S. Appl. No. 09/394,375, "Vacuum Ultraviolet Optical System for Operation in Ambient Atmosphere" Inventors: Michael J. Mandella & Dale A. Harrison, filed Sep. 10, 1999.

(Continued)

*Primary Examiner* — Tarifur Chowdhury
(74) *Attorney, Agent, or Firm* — D. Kligler I.P. Services Ltd

(57) ABSTRACT

A spectroscopy system is provided which is optimized for operation in the VUV region and capable of performing well in the DUV-NIR region. Additionally, the system incorporates an optical module which presents selectable sources and detectors optimized for use in the VUV and DUV-NIR. As well, the optical module provides common delivery and collection optics to enable measurements in both spectral regions to be collected using similar spot properties. The module also provides a means of quickly referencing measured data so as to ensure that highly repeatable results are achieved. The module further provides a controlled environment between the VUV source, sample chamber and VUV detector which acts to limit in a repeatable manner the absorption of VUV photons. The use of broad band data sets which encompass VUV wavelengths, in addition to the DUV-NIR wavelengths enables a greater variety of materials to be meaningfully characterized. Array based detection instrumentation may be exploited to permit the simultaneous collection of larger wavelength regions.

20 Claims, 33 Drawing Sheets

U.S. PATENT DOCUMENTS

| | | |
|---|---|---|
| 3,160,752 A | 12/1964 | Bennett |
| 3,572,951 A | 3/1971 | Rothwarf et al. |
| 3,751,643 A | 8/1973 | Dill et al. |
| 3,825,347 A | 7/1974 | Kaiser |
| 4,029,419 A | 6/1977 | Schumann et al. |
| 4,040,750 A | 8/1977 | Zwiener |
| 4,368,983 A | 1/1983 | Bennett |
| 4,645,349 A | 2/1987 | Tabata |
| 4,729,657 A | 3/1988 | Cooper et al. |
| 4,837,603 A | 6/1989 | Hayashi |
| 4,899,055 A | 2/1990 | Adams |
| 4,984,894 A | 1/1991 | Kondo |
| 5,042,949 A | 8/1991 | Greenberg et al. |
| 5,045,704 A | 9/1991 | Coates |
| 5,120,966 A | 6/1992 | Kondo |
| 5,128,549 A | 7/1992 | Kaye |
| 5,182,618 A | 1/1993 | Heinonen |
| 5,241,366 A | 8/1993 | Bevis et al. |
| 5,251,006 A | 10/1993 | Hongis et al. |
| 5,357,448 A | 10/1994 | Stanford |
| RE34,783 E | 11/1994 | Coates |
| 5,388,909 A | 2/1995 | Johnson et al. |
| 5,440,141 A | 8/1995 | Horie |
| 5,452,091 A | 9/1995 | Johnson |
| 5,486,701 A | 1/1996 | Norton et al. |
| 5,493,401 A | 2/1996 | Horie et al. |
| 5,581,350 A | 12/1996 | Chen et al. |
| 5,607,800 A | 3/1997 | Ziger |
| 5,608,526 A | 3/1997 | Piwonka-Corle et al. |
| 5,686,993 A | 11/1997 | Kokubo et al. |
| 5,747,813 A | 5/1998 | Norton et al. |
| 5,754,296 A | 5/1998 | Law |
| 5,771,094 A | 6/1998 | Carter |
| 5,777,733 A | 7/1998 | Radziuk |
| 5,781,304 A | 7/1998 | Kotidis et al. |
| 5,784,167 A | 7/1998 | Ho |
| 5,798,837 A | 8/1998 | Aspnes et al. |
| 5,805,285 A | 9/1998 | Johs et al. |
| 5,867,276 A | 2/1999 | McNeil et al. |
| 5,880,831 A | 3/1999 | Buermann et al. |
| 5,900,939 A | 5/1999 | Aspnes et al. |
| 5,903,351 A | 5/1999 | Jeong et al. |
| 5,917,594 A | 6/1999 | Norton |
| 5,991,022 A | 11/1999 | Buermann et al. |
| 6,052,401 A | 4/2000 | Wieser et al. |
| 6,091,485 A | 7/2000 | Li et al. |
| 6,122,052 A | 9/2000 | Barnes et al. |
| 6,128,085 A | 10/2000 | Buermann et al. |
| 6,129,807 A | 10/2000 | Grimbergen et al. |
| 6,181,427 B1 | 1/2001 | Yarussi et al. |
| 6,184,529 B1 | 2/2001 | Contini |
| 6,184,984 B1 | 2/2001 | Lee |
| 6,226,086 B1 | 5/2001 | Holbrook et al. |
| 6,261,853 B1 | 7/2001 | Howell et al. |
| 6,265,033 B1 | 7/2001 | Hilliard |
| 6,275,292 B1 | 8/2001 | Thakur et al. |
| 6,278,519 B1 | 8/2001 | Rosencwaig et al. |
| 6,297,880 B1 | 10/2001 | Rosencwaig et al. |
| 6,304,326 B1 | 10/2001 | Aspnes et al. |
| 6,313,466 B1 | 11/2001 | Olsen et al. |
| 6,340,602 B1 | 1/2002 | Johnson et al. |
| 6,361,646 B1 | 3/2002 | Bibby, Jr. et al. |
| 6,392,756 B1 | 5/2002 | Li et al. |
| 6,411,385 B2 | 6/2002 | Aspnes et al. |
| 6,414,302 B1 | 7/2002 | Freeouf |
| 6,417,921 B2 | 7/2002 | Rosencwaig et al. |
| 6,433,878 B1 | 8/2002 | Niu et al. |
| 6,453,006 B1 | 9/2002 | Koppel |
| 6,485,872 B1 | 11/2002 | Rosenthal et al. |
| 6,525,829 B1 | 2/2003 | Powell et al. |
| 6,549,279 B2 | 4/2003 | Adams et al. |
| 6,556,303 B1* | 4/2003 | Rangarajan et al. .......... 356/446 |
| 6,572,951 B2 | 6/2003 | Hasegawa et al. |
| 6,580,510 B2 | 6/2003 | Nawracala |
| 6,590,656 B2 | 7/2003 | Xu et al. |
| 6,608,690 B2* | 8/2003 | Niu et al. ...................... 356/635 |
| 6,630,673 B2 | 10/2003 | Khalil et al. |
| 6,630,996 B2 | 10/2003 | Rao et al. |
| 6,633,831 B2 | 10/2003 | Nikoonahad et al. |
| 6,643,354 B2 | 11/2003 | Koppel et al. |
| 6,657,737 B2 | 12/2003 | Kimba et al. |
| 6,665,075 B2 | 12/2003 | Mittleman et al. |
| 6,673,637 B2 | 1/2004 | Wack et al. |
| 6,710,865 B2 | 3/2004 | Forouhi et al. |
| 6,713,775 B2 | 3/2004 | Chelvayohan et al. |
| 6,721,052 B2 | 4/2004 | Zhao et al. |
| 6,734,968 B1 | 5/2004 | Wang et al. |
| 6,765,676 B1 | 7/2004 | Buermann |
| 6,768,785 B2 | 7/2004 | Koppel |
| 6,801,309 B1 | 10/2004 | Nelson |
| 6,806,951 B2 | 10/2004 | Wack et al. |
| 6,879,395 B2 | 4/2005 | Oka et al. |
| 6,891,626 B2 | 5/2005 | Niu et al. |
| 6,897,456 B2 | 5/2005 | Hasegawa et al. |
| 6,917,419 B2 | 7/2005 | Fielden et al. |
| 6,919,957 B2 | 7/2005 | Nikoonahad et al. |
| 6,934,025 B2 | 8/2005 | Opsal et al. |
| 6,979,578 B2 | 12/2005 | Venugopal |
| 6,982,792 B1 | 1/2006 | Woollam et al. |
| 6,987,832 B2 | 1/2006 | Koppel et al. |
| 7,006,235 B2 | 2/2006 | Levy et al. |
| 7,026,165 B2 | 4/2006 | DeGrandpre |
| 7,026,626 B2 | 4/2006 | Harrison |
| 7,061,614 B2 | 6/2006 | Wang et al. |
| 7,067,818 B2 | 6/2006 | Harrison |
| 7,072,050 B2 | 7/2006 | Kimba et al. |
| 7,095,511 B2 | 8/2006 | Chalmers et al. |
| 7,126,131 B2 | 10/2006 | Harrison |
| 7,130,029 B2 | 10/2006 | Wack et al. |
| 7,189,973 B2 | 3/2007 | Harrison |
| 7,196,785 B2 | 3/2007 | Nishiyama et al. |
| 7,224,471 B2 | 5/2007 | Bischoff et al. |
| 7,242,477 B2 | 7/2007 | Mieher et al. |
| 7,271,394 B2 | 9/2007 | Harrison |
| 7,282,703 B2 | 10/2007 | Walsh et al. |
| 7,342,235 B1 | 3/2008 | Harrison |
| 7,391,030 B2 | 6/2008 | Harrison |
| 7,394,551 B2 | 7/2008 | Harrison |
| 7,399,975 B2 | 7/2008 | Harrison |
| 7,485,869 B2 | 2/2009 | Harrison et al. |
| 7,511,265 B2 | 3/2009 | Walsh et al. |
| 7,643,666 B2 | 1/2010 | Setija et al. |
| 7,684,037 B2 | 3/2010 | Harrison et al. |
| 2001/0055118 A1 | 12/2001 | Nawracala |
| 2002/0030826 A1 | 3/2002 | Chalmers et al. |
| 2002/0088952 A1 | 7/2002 | Rao et al. |
| 2002/0126277 A1 | 9/2002 | Norton et al. |
| 2002/0131055 A1* | 9/2002 | Niu et al. ...................... 356/603 |
| 2002/0149774 A1 | 10/2002 | McAninch |
| 2002/0154302 A1 | 10/2002 | Rosencwaig |
| 2002/0190207 A1 | 12/2002 | Levy et al. |
| 2003/0071996 A1 | 4/2003 | Wang et al. |
| 2003/0081201 A1* | 5/2003 | Shibata et al. ............. 356/237.2 |
| 2004/0150820 A1* | 8/2004 | Nikoonahad et al. ......... 356/364 |
| 2005/0002037 A1 | 1/2005 | Harrison |
| 2005/0036143 A1 | 2/2005 | Huang |
| 2006/0001885 A1 | 1/2006 | Hertzsch et al. |
| 2006/0192958 A1 | 8/2006 | Harrison |
| 2007/0030488 A1 | 2/2007 | Harrison |
| 2007/0181793 A1 | 8/2007 | Harrison |
| 2007/0215801 A1 | 9/2007 | Walsh et al. |
| 2008/0073560 A1 | 3/2008 | Harrison et al. |
| 2008/0181793 A1 | 7/2008 | Mistry et al. |
| 2008/0246951 A1 | 10/2008 | Walsh et al. |
| 2009/0002711 A1 | 1/2009 | Harrison |
| 2009/0248074 A1 | 10/2009 | Kliegman et al. |
| 2010/0051822 A1 | 3/2010 | Harrison |

FOREIGN PATENT DOCUMENTS

| | | |
|---|---|---|
| CN | 2430682 Y | 5/2001 |
| JP | 10160572 A | 6/1998 |
| JP | 2003202266 A | 7/2003 |
| JP | 2003232681 A | 8/2003 |
| WO | 9902970 A1 | 1/1999 |
| WO | 2007126612 A2 | 11/2007 |
| WO | 2007130295 A2 | 11/2007 |

OTHER PUBLICATIONS

McPherson Product Brochure "Reflectometer for Sample Analysis," McPherson, Inc., Massachusetts, Published Prior to Sep. 23, 2003, 1-2 pps.
McPherson Product Brochure "Spectral Reflectometer," McPherson, Inc., Massachusetts, Nov. 12, 2001, 1 pg.
McPherson Product Brochure "VUVaS Spectrophotometers for 115 nm to >380 nm," McPherson, Inc., Massachusetts, Published Prior to Sep. 23, 2003, 1-4 pps.
McPherson Product Brochure "VUVaS Spectrophotometers, Made to Measure 115-380 nm," McPherson, Inc., Massachusetts, Published Prior to Sep. 23, 2003, 1-8 pps.
Acton Research Product Brochure "Acton Research Purged CAMS Optical Measurement System," Acton Research Corporation, Massachusetts, Published Prior to Sep. 23, 2003, 1-2 pps.
"The Thin Film tool for next generation lithography at 157nm," Web page from http://www.sopra-sa.com, Sopra, Printed From Internet on Feb. 19, 2002, 1pg.
"SE and GXR combined on the same instrument," Web page from http://www.sopra-sa.com, Sopra, Printed From Internet on Feb. 19, 2002, 1pg.
"The ideal Thin Film characterization unit for Development and Pilot Line environment," Web page from http://www.sopra-sa.com, Sopra, Printed From Internet on Feb. 19, 2002, 1 pg.
"VUV-VASE™, The Award Winning VUV-VASE™ is the latest addition to our line of Spectroscopic Ellipsometers," Web pages from http://www.jawoolam.com, J.A. Woollam Company, Nebraska, Printed From Internet on Nov. 5, 2002, 1-2 pps.
"Vacuum UV Spectroscopic Ellipsometers," Web pages from http://www.sentech.de, Sentech Instruments, Printed From Internet on Feb. 20, 2002, 1-3 pps.
Search Report;PCT/US04/30859; 13 pgs.
Rubloff, "Surface Reflectance Spectroscopy System", Technical Disclosure, Ip.com, www.ip.com, May 1, 1977, 5 pgs.
Request for Ex Parte Reexamination Transmittal Form for U.S. Patent 7,067,818, May 30, 2008, 23 pgs.
Harrison, Ex Parte Reexamination Communication Transmittal Form, Sep. 19, 2008, 12 pgs.
Request for Ex Parte Reexamination Transmittal Form for U.S. Patent 7,026,626, Harrison et al., Nov. 4, 2008, May 30, 2008, 22 pgs.
Request for Ex Parte Reexamination Transmittal Form for U.S. Patent 7,189,973, Harrison, Feb. 11, 2009, 24 pgs.
Das et al., "Image Evaluation of the High-Resolution VUV Spectrometer at SURF II by Ray Tracing", Journal of Research of the National Institute of Standards and Technology, vol. 103, No. 5, pp. 483-495, Sep.-Oct. 1998.
US Re-Examination U.S. Appl. No. 90/009,409 Official Action dated Jun. 18, 2010.
Chinese Patent Application No. 200480027513.6 Official Action dated Jul. 18, 2008.
US Re-Examination U.S. Appl. No. 90/009,320 Official Action dated Sep. 25, 2009, and Notice of Intent to Issue Re-Exam Certificate dated Jun. 23, 2010.
Aspnes, D.E., "Determination of Optical Properties by Ellipsometry", Handbook of Optical Constants of Solids, vol. 1, pp. 104-108, Academic Press, 1998.
Bloomstein et al., "Contamination Rates of Optical Surface at 157nm in the Presence of Hydrocarbon Impurities", Optical Microlithography XV, Proceedings of the SPIE, vol. 4691, pp. 709-723, Jul. 30, 2002.
Field et al., "Method of Using the Reflectance Ratios of Difference Angles of Incidence for the Determination of Optical Constants", Applied Optics, vol. 10, No. 6, pp. 1402-1405, Jun. 1971.
Hunter, W., "Errors in Using the Reflectance vs Angle of Incidence Method for Measuring Optical Constants", Journal of the Optical Society of America, vol. 55, No. 10, part 1, pp. 1197-1204, Oct. 1965.
Hunter et al., "Thickness of Absorbing Films Necessary to Measure Their Optical Constants Using the Reflectance-Vs-Angle-of-Incidence Method", Journal of the Optical Society of America, vol. 64, No. 4, pp. 429-433, Apr. 1974.
Jellison et al., "Parameterization of the Optical Functions of Amorphous Materials in the Interband Region", Applied Physics Letter, Jul. 15, 1996 (vol. 69, No. 3, pp. 371-373), and Sep. 30, 1996 (vol. 69, No. 14, p. 2137).
Okoroanyanwu et al., "Contamination Monitoring and Control on ASML MS-VII 157nm Exposure Tool", Optical Microlithography XVII, Proceedings of the SPIE, vol. 5377, pp. 1695-1707, May 28, 2004.
Press et al., "Numerical Recipes in C: 15.5 Non-Linear models", The Art of Scientific Computing, Second Edition, 15.5 Non-Linear models, pp. 681-688, Cambridge University Press 2002.
Rivas, C., "Optical Characterization of Hafnium-Based High-K Dielectric Films Using Vacuum Ultraviolet Reflectometry", Proceedings of the XV International Conference on Vacuum Ultraviolet Radiation Physics, Berlin, Germany Jul. 29-Aug. 3, 2007.
International Application PCT/US2007/010003 Search Report issued Dec. 17, 2008.
U.S. Appl. No. 10/930,339 Official Action dated Sep. 29, 2009.
U.S. Appl. No. 10/930,339 Official Action dated Jan. 18, 2007.
U.S. Appl. No. 10/930,339 Official Action dated Sep. 6, 2007.
U.S. Appl. No. 10/930,339 Official Action dated Apr. 18, 2008.
U.S. Appl. No. 10/930,339 Official Action dated Nov. 13, 2008.
Hurst et al., U.S. Appl. No. 12/454,837 "Automated Calibration Methodology for VUV Metrology System" filed on May 22, 2009.
Visentine, J., "Optical Characterization of Molecular Contaminant Films", Photonics Tech Briefs, Jan. 1, 2007.
U.S. Appl. No. 12/592,641 Official Action dated Aug. 20, 2010.
Japanese Patent Application # 528098/06 Official Action dated Jun. 15, 2010 (including English translation).
US Re-Examination U.S. Appl. No. 95/000,535 Official Action dated May 14, 2010.
U.S. Appl. No. 12/876,242 Official Action dated Nov. 19, 2010.
U.S. Appl. No. 12/592,641 Official Action dated Aug. 20, 2010.
U.S. Appl. No. 12/834,939 Official Action dated Jun. 10, 2011.
U.S. Appl. No. 12/876,242 Official Action dated May 20, 2011.

* cited by examiner

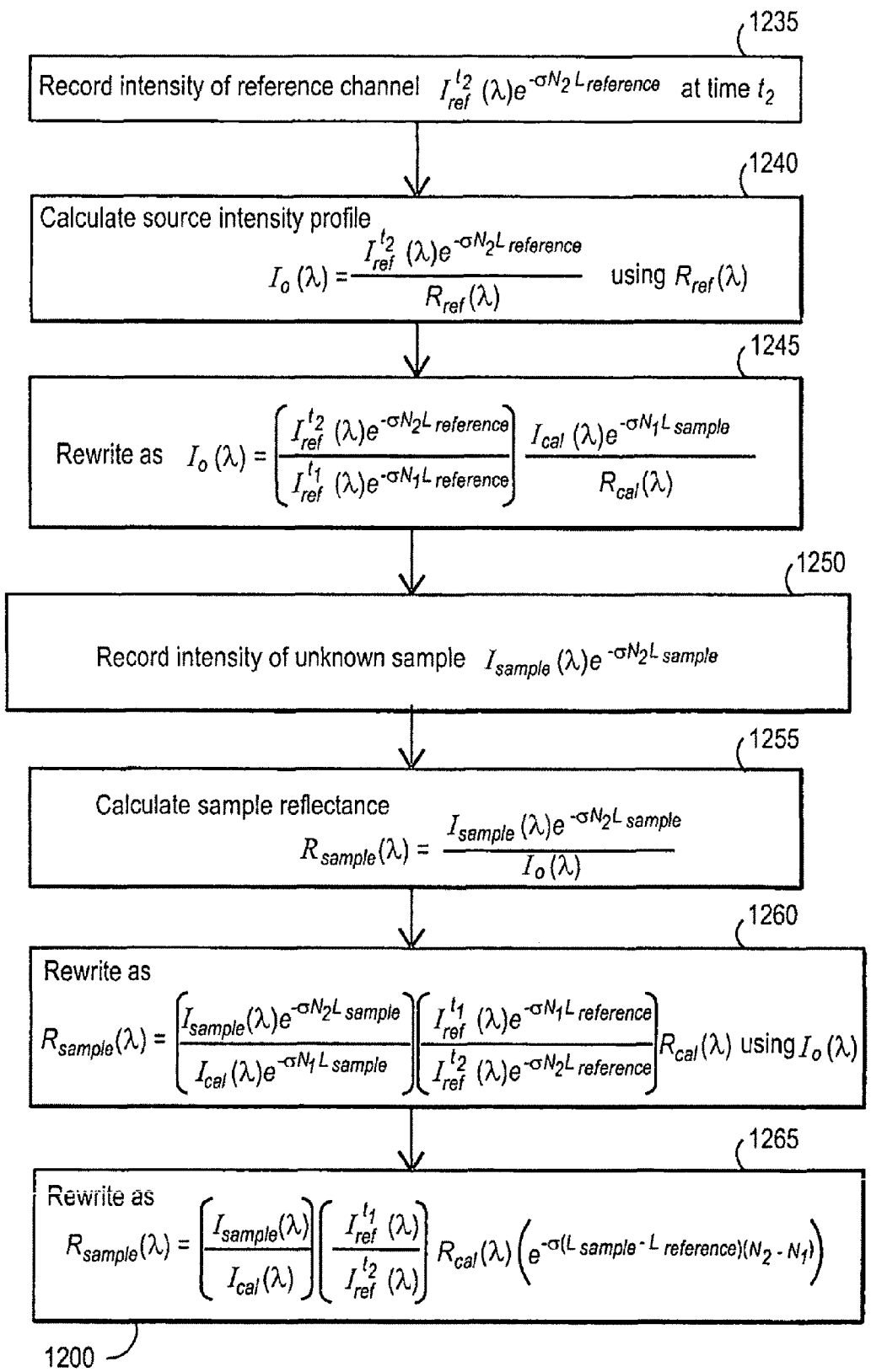
FIG. 12A-B

BROAD BAND REFERENCING REFLECTOMETER

CROSS-REFERENCE TO RELATED APPLICATIONS

This application is a continuation of U.S. patent application Ser. No. 12/231,350 filed on Sep. 2, 2008 now abandoned which is a continuation of U.S. patent application Ser. No. 11/517,894 filed on Sep. 8, 2006, now U.S. Pat. No. 7,446,876 which is a continuation of U.S. patent application Ser. No. 10/909,126 filed on Jul. 30, 2004, now U.S. Pat. No. 7,126,131, which is a continuation-in-part of (1) U.S. patent application Ser. No. 10/669,030 filed on Sep. 23, 2003, now U.S. Pat. No. 7,026,626, which claims priority to Provisional Patent Application Nos. 60/440,434, 60/440,435, and 60/440,443 all filed Jan. 16, 2003; (2) U.S. patent application Ser. No. 10/668,642 filed on Sep. 23, 2003, now U.S. Pat. No. 7,067,818, which claims priority to Provisional Patent Application Nos. 60/440,434, 60/440,435, and 60/440,443 all filed Jan. 16, 2003; and (3) U.S. patent application Ser. No. 10/668,644 filed on Sep. 23, 2003, now U.S. Pat. No. 7,394,551, which claims priority to Provisional Patent Application Nos. 60/440,434, 60/440,435, and 60/440,443 all filed Jan. 16, 2003; the disclosures of which are each expressly incorporated herein by reference.

BACKGROUND OF THE INVENTION

The present invention relates to the field of optical metrology. More specifically it provides a means by which repeatable reflectance measurements may be performed over a broad range of wavelengths that includes the vacuum ultraviolet (VUV) (generally wavelengths less than 190 nm) and at least one other spectral region.

Optical metrology techniques have long been employed in process control applications in the semiconductor manufacturing industry due to their non-contact, non-destructive and generally high-throughput nature. The vast majority of these tools operate in some portion of the spectral region spanning the deep ultraviolet and near-infrared wavelengths (DUV-NIR generally 200-1000 nm). The push towards thinner layers and the introduction of new complicated materials has challenged the sensitivity of such instrumentation. As a result, this has necessitated an effort to develop optical metrology equipment utilizing shorter wavelengths (below 200 nm), where greater sensitivity to subtle changes in material properties can be realized. One approach to performing optical measurements at shorter wavelengths is described in U.S. application Ser. No. 10/668,642, which discloses a system and method for a vacuum ultraviolet (VUV) reflectometer.

Virtually all optical metrology instruments incorporate some form of modeling algorithms to extract meaningful material information from the quantities they initially record. The performance of such algorithms depends heavily on the nature of the data sets they are to reduce. Data sets covering a wider range of wavelengths generally provide more constraint to fitting algorithms thereby rendering faster convergence and more accurate results.

The conventional approach to collecting reflectance data over a broad range of wavelengths covering at least two spectral regions is to employ a step and scan technique wherein a single element detector is used in conjunction with a rotating grating monochromator. Often if the range of wavelengths investigated is large enough, it may be necessary to manually change out gratings, detectors, optics and sources during the acquisition of a single broad-band data set. This approach is often time consuming and not well suited to manufacturing environments like those encountered in the semiconductor industry.

Interferometers are widely used in the infrared spectral region to collect data over a wide range of wavelengths; however, these instruments are not commonly employed in the VUV since optical and mechanical tolerances of the instrument scale with wavelength and are difficult to satisfy in this spectral region.

Wang, in U.S. Patent Application 20030071996, discloses a measurement system with separate optimized beam paths. Although this system enables efficient measurements to be performed over a number of spectral sub-bands, it provides no means of referencing the collected data. Hence, while signal throughput may be high, system repeatability may be quite poor. This is particularly relevant when operating in the VUV since such wavelengths are highly susceptible to atmospheric changes necessitating frequent referencing.

The collection of highly repeatable reflectance data in the VUV is perhaps best achieved using a system designed to minimize and/or altogether eliminate errors introduced by data altering environmental changes which may occur between conclusion of a calibration measurement and commencement of a subsequent sample measurement. An example of such a system is described in U.S. application Ser. No. 10/668,644. The applicant has identified that it would be desirable to extend this capability in order to facilitate its use in a reflectometer capable of acquiring data over a broad range of wavelengths including the VUV and at least one other spectral region.

The applicant has further identified that it would be desirable to ensure that data sets from each of the spectral regions comprising the entire broad band of wavelengths are collected from the same physical location on the sample and with the same spot size. Moreover, it would also be advantageous if such data sets were collected using the same orientation (i.e. angle of incidence and direction) relative to the sample in order to ensure that similar scattering conditions are encountered.

The applicant has also identified that it would be desirable if said system made use of a serial collection process wherein data from each of the spectral regions were collected sequentially to avoid stray light complications, which one would expect if a parallel process was employed.

SUMMARY OF THE INVENTION

An objective of the current invention is to provide the semiconductor manufacturing industry with a reliable optical metrology tool that is capable of characterizing semiconductor devices incorporating thinner layers and new complicated materials. Any fitting algorithms employed by a user of the instrument may achieve faster convergence and more accurate results by taking full advantage of the higher level of constraint afforded by a data set comprised of two or more spectral regions. This instrument will be non-contact and non-destructive and will make use of broad band reflectance data.

The instrument will be optimized for operation in a first spectral region and capable of performing well in at least one other spectral region. A selection of sources and detectors for use in separate spectral regions are incorporated within an optical module in the instrument that permits their selection. Additionally, this module contains common delivery and collection optics to enable measurements in separate spectral regions to be collected using similar spot properties. Furthermore, the invention employs a serial collection approach whereby data from separate spectral regions is collected sequentially to avoid stray light complications.

In one embodiment a spectroscopy system is provided which is optimized for operation in a first spectral region and capable of performing well in at least one other. The system is designed such that no moving optical elements (apart from shutters) are involved in the collection of data from the first spectral region. Additionally, the system incorporates an optical module which presents selectable sources and detectors optimized for separate spectral regions. As well, the optical module provides common delivery and collection optics to enable measurements in separate spectral regions to be collected using similar spot properties. The module also provides a means of quickly referencing measured data so as to ensure that highly repeatable results are achieved.

In another embodiment a spectroscopy system is provided which is optimized for operation in the VUV and capable of performing well in the DUV-NIR. Additionally, the system incorporates an optical module which presents selectable sources and detectors optimized for use in the VUV and DUV-NIR. As well, the optical module provides common delivery and collection optics to enable measurements in both spectral regions to be collected using similar spot properties. The module also provides a means of quickly referencing measured data so as to ensure that highly repeatable results are achieved. The module further provides a controlled environment between the VUV source, sample chamber and VUV detector which acts to limit in a repeatable manner the absorption of VUV photons. The use of broad band data sets which encompass VUV wavelengths, in addition to the DUV-NIR wavelengths enables a greater variety of materials to be meaningfully characterized. Array based detection instrumentation may be exploited to permit the simultaneous collection of larger wavelength regions.

An objective of the current invention is to provide the semiconductor manufacturing industry with a reliable optical metrology tool that is capable of characterizing semiconductor devices incorporating thinner layers and smaller features. This instrument will take full advantage of the heightened levels of sensitivity to small changes in processing conditions that are afforded through the characterization of materials at and below the VUV wavelength region. This instrument will be non-contact and non-destructive and will make use of referenced reflectometry data.

The design of the instrument is simple and robust rendering it easy to operate at VUV wavelengths. As a result of its simplicity it is fast, thereby lending it to use in high throughput manufacturing applications. The system is designed such that it is compact and requires little space. The instrument offers the advantage of minimizing environmental effects so far as to remove the need to sustain a reproducible controlled environment during the course of calibration, referencing and sample measurement. Additionally, it offers a small measurement spot size such that in-line measurements on product samples are possible and employ imaging optics such that multiple measurements on a series of sites within a localized region can be obtained simultaneously.

In one embodiment, a spectroscopy system is provided which operates in the vacuum ultra-violet spectrum. More particularly, a system utilizing reflectometry techniques in the vacuum ultraviolet spectrum is provided for use in metrology applications. The system may further include the use of an array detector in combination with an imaging spectrometer. In this manner data for multiple wavelengths may be simultaneously collected. Moreover, the multiple wavelengths of data may be collected simultaneously for a two dimensional sample area. The system may further include the use of a fixed diffraction grating and does not require the use of polarizing elements. To ensure accurate and repeatable measurement, the environment of the optical path is controlled. The optical path may include a controlled environmental chamber in which non-absorbing purge gases are present or in which vacuum evacuation techniques are utilized. The controlled environment may further include a separate instrument chamber and a separate sample chamber. The controlled environment limits in a repeatable manner the absorption of VUV photons.

In another embodiment, a spectroscopy system is provided which operates in the vacuum ultra-violet spectrum. More particularly, a system utilizing reflectometry techniques in the vacuum ultraviolet spectrum is provided for use in metrology applications. To ensure accurate and repeatable measurement, the environment of the optical path is controlled to limit absorption effects of gases that may be present in the optical path. To account for absorption effects that may still occur, the length of the optical path is minimized. To further account for absorption effects, the reflectance data may be referenced to a relative standard. Referencing is particularly advantageous in the VUV reflectometer due to the low available photon flux and the sensitivity of recorded data to the composition of the gaseous medium contained with the optical path. Thus, errors that may be introduced by changes in the controlled environment may be reduced. In one exemplary embodiment, the VUV reflectometer may utilize a technique in which a beam splitter is utilized to create a sample beam and a reference beam to form the two arms of a near balanced Mach Zehnder interferometer. In another exemplary embodiment, the reference channel may be comprised of a Michelson interferometer.

In still another embodiment, a spectroscopy system is provided which operates in the vacuum ultra-violet spectrum. More particularly, a system utilizing reflectometry techniques in the vacuum ultraviolet spectrum is provided for use in metrology applications. To ensure accurate and repeatable measurement, the environment of the optical path is controlled to limit absorption effects of gases that may be present in the optical path. The VUV reflectometer may be utilized to monitor a wide range of data in a semiconductor processing environment. For example, the techniques may be used for measuring thicknesses, optical properties, composition, porosity and roughness of a film or stack of films. Further, these VUV techniques and apparatus may be used to characterize critical dimensions and other features of a device. The VUV reflectometer system may be utilized as a stand alone tool, or the relatively compact nature of the system may be taken advantage of such that the system is incorporated into other process tools. Thus, for example, the VUV techniques described herein may be incorporated directly into tools used for deposition, etch, photolithography, etc. so that in-line measurements, monitoring and control may be advantageously obtained.

A further understanding of the nature of the advantages of the present invention may be realized following review of the following descriptions and associated drawings.

BRIEF DESCRIPTION OF THE DRAWINGS

A more complete understanding of the present invention and advantages thereof may be acquired by referring to the following description taken in conjunction with the accompanying drawings, in which like references numbers indicate like features. It is to be noted, however, that the accompanying drawings illustrate only exemplary embodiments of the invention and are therefore not to be considered limiting of its scope, for the invention may admit to other equally effective embodiments.

DESCRIPTION OF THE PREFERRED EMBODIMENTS

To enhance the sensitivity of optical metrology equipment for challenging applications it is desirable to extend the range of wavelengths over which such measurements are performed. Specifically, it is advantageous to utilize shorter wavelength (higher energy) photons extending into, and beyond, the region of the electromagnetic spectrum referred to as the vacuum ultra-violet (VUV). Historically there has been relatively little effort expended on the development of optical instrumentation designed to operate at these wavelengths, owing to the fact that VUV (and lower) photons are strongly absorbed in standard atmospheric conditions. Vacuum ultra-violet (VUV) wavelengths are generally considered to be wavelengths less than deep ultra-violet (DUV) wavelengths. Thus VUV wavelengths are generally considered to be wavelengths less than about 190 nm. While there is no universal cutoff for the bottom end of the VUV range, some in the field may consider VUV to terminate and an extreme ultra-violet (EUV) range to begin (for example some may define wavelengths less than 100 nm as EUV). Though the principles described herein may be applicable to wavelengths above 100 nm, such principles are generally also applicable to wavelengths below 100 nm. Thus, as used herein it will be recognized that the term VUV is meant to indicate wavelengths generally less than about 190 nm however VUV is not meant to exclude lower wavelengths. Thus as described herein VUV is generally meant to encompass wavelengths generally less than about 190 nm without a low end wavelength exclusion. Furthermore, low end VUV may be construed generally as wavelengths below about 140 nm.

Indeed it is generally true that virtually all forms of matter (solids, liquids and gases) exhibit increasingly strong optical absorption characteristics at VUV wavelengths. Ironically it is this same rather fundamental property of matter which is itself responsible for the increased sensitivity available to VUV optical metrology techniques. This follows as small changes in process conditions, producing undetectable changes in the optical behavior of materials at longer wavelengths, can induce substantial and easily detectable changes in the measurable characteristics of such materials at VUV wavelengths.

Figure 1:
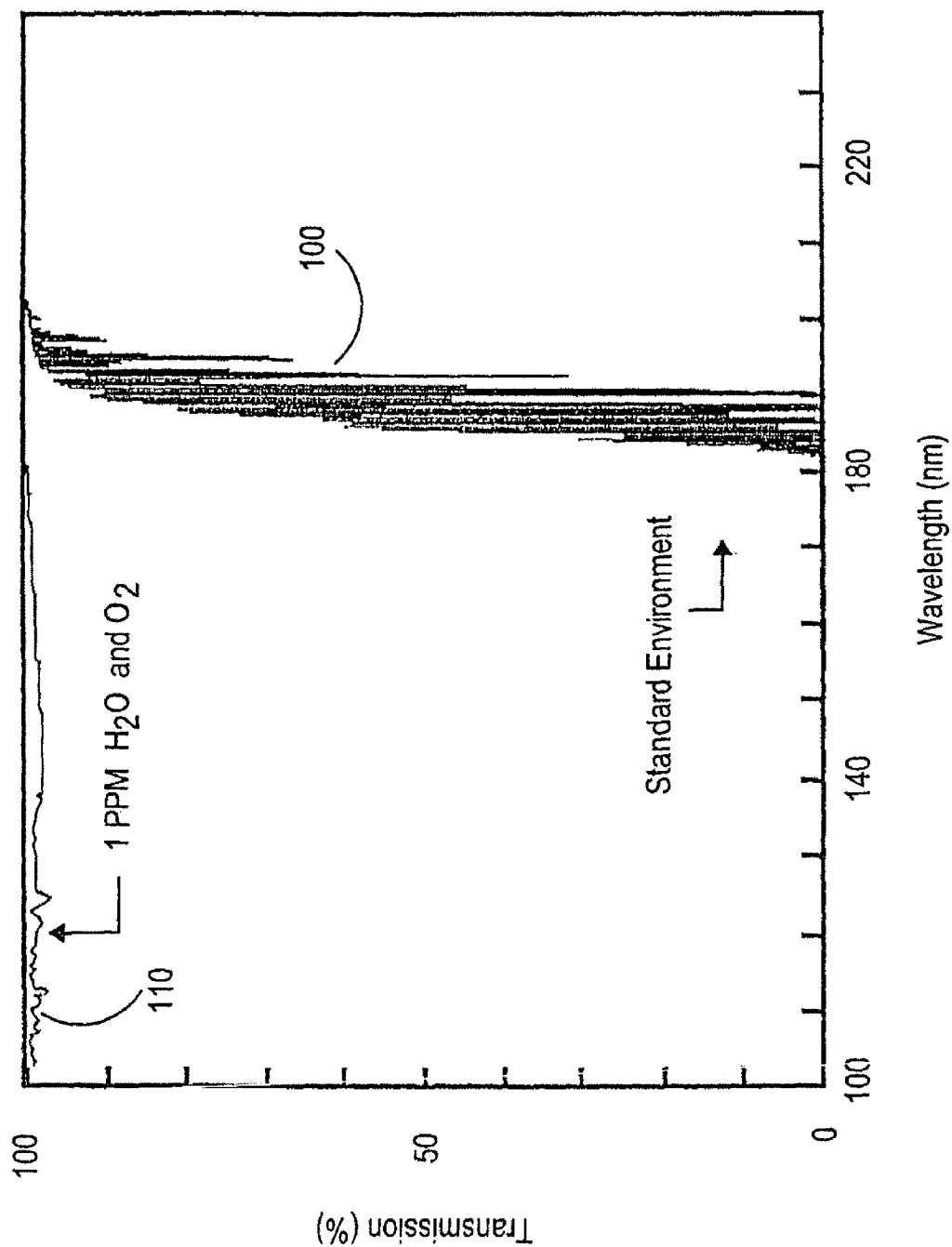
FIG. 1—Comparison of optical transmission through 100 cm of standard atmosphere versus 100 cm of controlled environment containing 1 PPM of H2O and O2.

The fact that VUV photons are strongly absorbed by most forms of matter precludes the simple extension of, or modification to, conventional longer wavelength optical metrology equipment in order to facilitate operation in the VUV. Current day tools are designed to operate under standard atmospheric conditions and typically lack, among other things, the controlled environment required for operation at these shorter wavelengths. VUV radiation is strongly absorbed by both $O_2$ and $H_2O$ molecules and hence these species must be maintained at sufficiently low levels as to permit transmission of VUV photons through the optical path of the instrument. To better illustrate this point the optical transmission through a 100 cm path length of both standard atmosphere (plot 100) and a controlled environment containing $O_2$ and $H_2O$ concentration levels of 1 PPM (plot 110) are plotted as a function of photon wavelength in FIG. 1. As is evident from the figure, the transmission of photons through standard atmosphere drops precipitously at wavelengths shorter than about 200 nm.

Not only are conventional optical instruments intended to function in standard atmospheric conditions they also typically employ an array of optical elements and designs which render them unsuitable for VUV operation. In order to achieve highly repeatable results with a reflectometer it is desirable to provide a means by which reflectance data can be referenced or compared to a relative standard. In this manner changes in the system that occur between an initial time when the system is first calibrated and a later time when a sample measurement is performed, can be properly accounted for. At longer wavelengths such changes are usually dominated by intensity variations in the spectral output of the source. When working at VUV wavelengths, however, changes in the environmental conditions (i.e. changes in the concentration of absorbing species in the environment of the optical path) can play a much larger role.

Thus, conventional longer wavelength systems fail to address the significant influence that the absorbing environment has on the measurement process. To ensure that accurate and repeatable reflectance data is obtained, it is desirable to not only provide a means of controlling the environment containing the optical path, but furthermore to ensure that the absorption effects which do occur are properly taken into account during all aspects of the calibration, measurement and reference processes.

Hence, it is desirable to provide an optical metrology tool with a controlled environment that is designed to operate at and below VUV wavelengths. In addition, in order to ensure that accurate and repeatable results are obtained, it is desirable that the design incorporate a robust referencing methodology that acts to reduce or altogether remove errors introduced by changes in the controlled environment.

Figure 2:
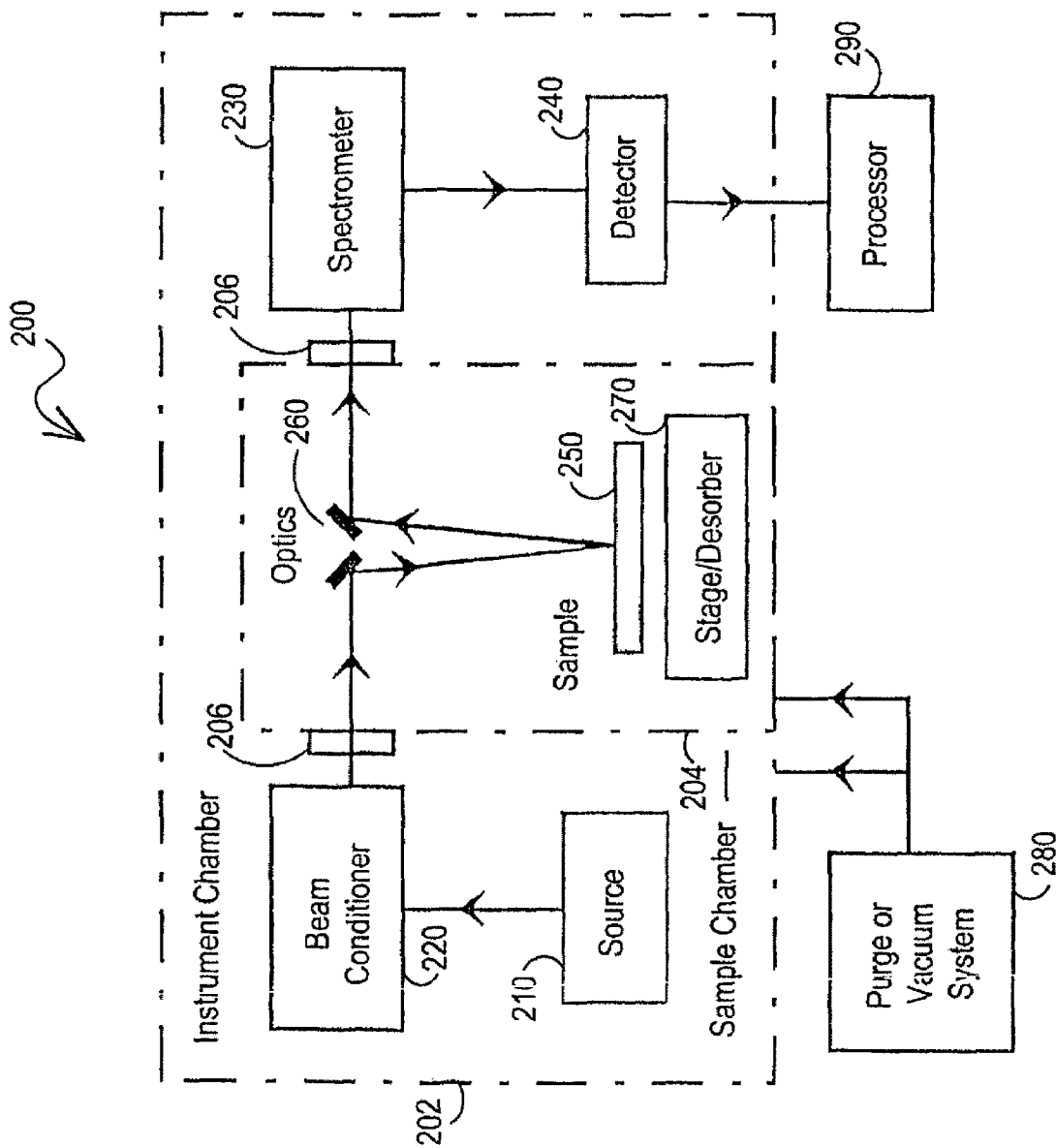
FIG. 2—Schematic representation of a VUV reflectometer.

A schematic representation of an optical reflectometer metrology tool 200 that depicts one embodiment of the present invention is presented in FIG. 2. As is evident, the source 210, beam conditioning module 220, optics (not shown), spectrometer 230 and detector 240 are contained within an environmentally controlled instrument chamber 202. The sample 250, additional optics 260, motorized stage 270 (which may include an optional desorber) are housed in a separate environmentally controlled sample chamber 204 so as to enable the loading and unloading of samples without contaminating the quality of the instrument chamber environment. The instrument and sample chambers are connected via a controllable coupling mechanism 206 which can permit the transfer of photons, and if so desired the exchange of gases to occur. For example, coupling mechanism 206 may be optical windows, may be gate valves which open when an optical transmission path is desired, or may be other mechanisms that suitably allow an optical path to be coupled between the two chambers. In this manner an optical path between the instrument and sample chambers is provided. Additionally a processor 290 located outside the controlled environment may be used to analyze the measured data. It will be recognized that processor 290 may be any of a wide variety of computing means that may provide suitable data processing and/or storage of the data collected.

While not explicitly shown in FIG. 2, it is noted that the system could also be equipped with a robot and other associated mechanized components to aid in the loading and unloading of samples in an automated fashion, thereby further increasing measurement throughput. Further, as is known in the art load lock chambers may also be utilized in conjunction with the sample chamber to improve environmental control and increase the system throughput for interchanging samples.

In operation light from the source 210 is modified, by way of beam conditioning module 220, and directed and focused via delivery optics through the coupling mechanism windows 206 and onto the sample 250 housed in the sample chamber 204. Light reflected from the sample travels back through the coupling mechanism 206, is captured by collection optics and focused onto the entrance plane of a spectrometer 230. As is discussed in more detail below, the spectrometer 230 may be in one embodiment an imaging spectrometer. This type of spectrometer is typically equipped with some form of multi-element detector 240 (for example an array detector), such that it is capable of collecting a range of data points simultaneously. The entire optical path of the device is maintained within controlled environments which function to remove absorbing species and permit transmission of VUV photons. The controlled environments may be created with purge or vacuum system 280 by introducing a non-absorbing purge gas like high purity nitrogen, argon, or helium into the instrument and sample chambers and/or through evacuation via vacuum, depending on the lowest operating wavelength desired. If a high purity purge gas is used, the coupling mechanism 206 could be comprised of $MgF_2$ windows, whereas if the chambers are evacuated then mechanical gate valves could be employed. Other potentially suitable window materials include fused silica, fluorine-doped fused silica, quartz, CaF, SrF, BaF, $MgF_2$, LaF and LiF. It will be recognized that by utilizing a combination of evacuation techniques and mechanical gate valves, absorption of photons may be further decreased.

Figure 3:
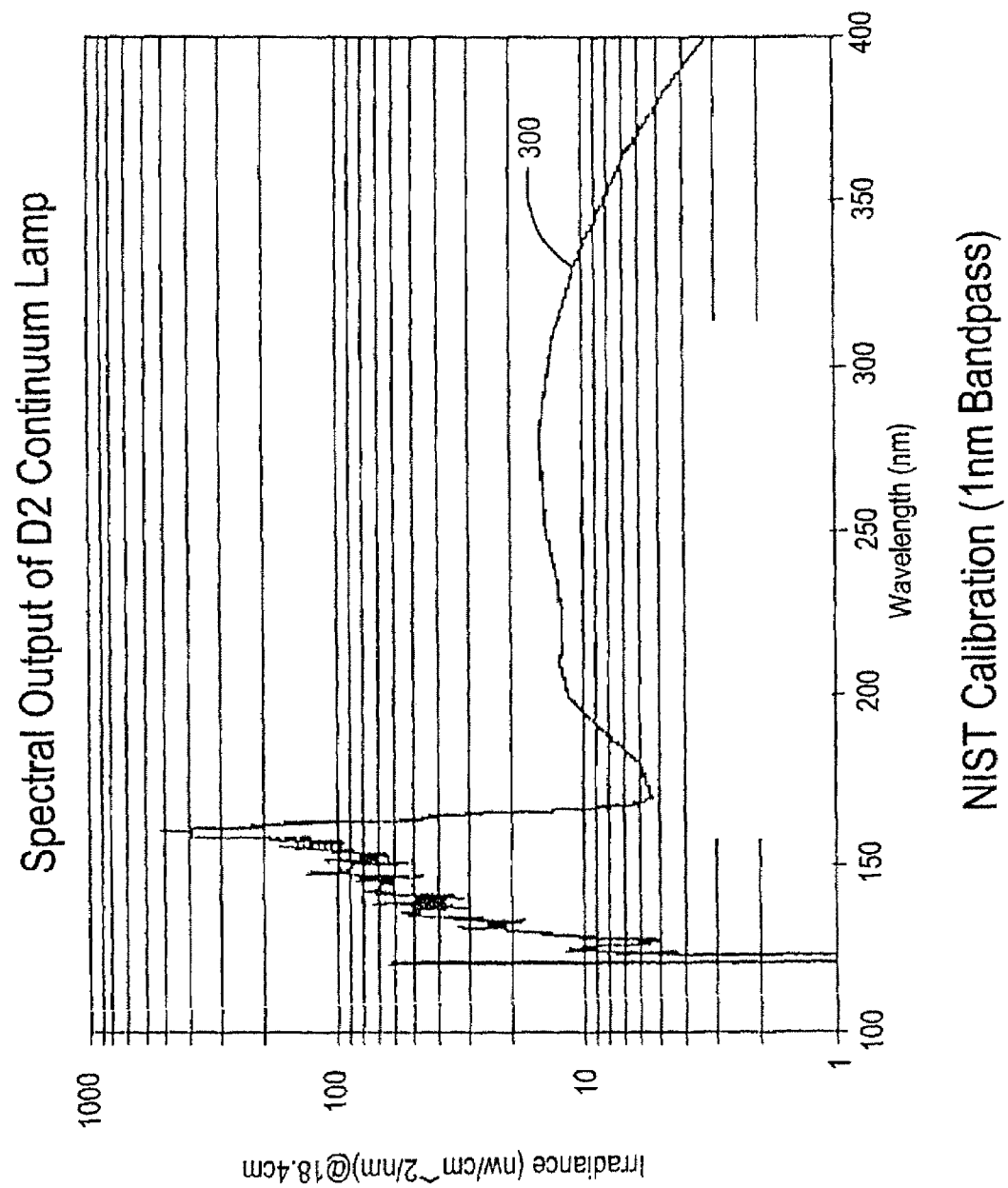
FIG. 3—Spectral output from Hamamatsu deuterium lamp equipped with an MgF2 window.

In one embodiment of the invention the VUV source 210 is a long nose projecting type deuterium ($D_2$) lamp, such as Model #L7293 manufactured by Hamamatsu of Japan. Such a source is a broad band VUV source and combines mature arc lamp technology with a magnesium fluoride (MgF$_2$) window to provide continuous emission down to about 115 nm (see plot 300 of FIG. 3). The window may however be comprised of a variety of VUV materials including fused silica, fluorine-doped fused silica, quartz, CaF, SrF, BaF, MgF$_2$, LaF and LiF. The projecting design of the lamp provides superior directivity thereby enabling efficient coupling of VUV photons into the reflectometer optical system. D$_2$ arc lamps are characterized by high stability, high brightness and long-life rendering them well-suited to demanding semiconductor metrology applications. Alternate embodiments of the invention may incorporate a variety of other VUV sources including, but not limited to, narrow band sources and windowless discharge sources which could emit photons at wavelengths down to and below 115 nm. For example, the windowless source may be a differentially pumped discharge source. Thus, the systems and techniques provided herein are particularly useful for low end VUV (or lower) applications.

Figure 4:
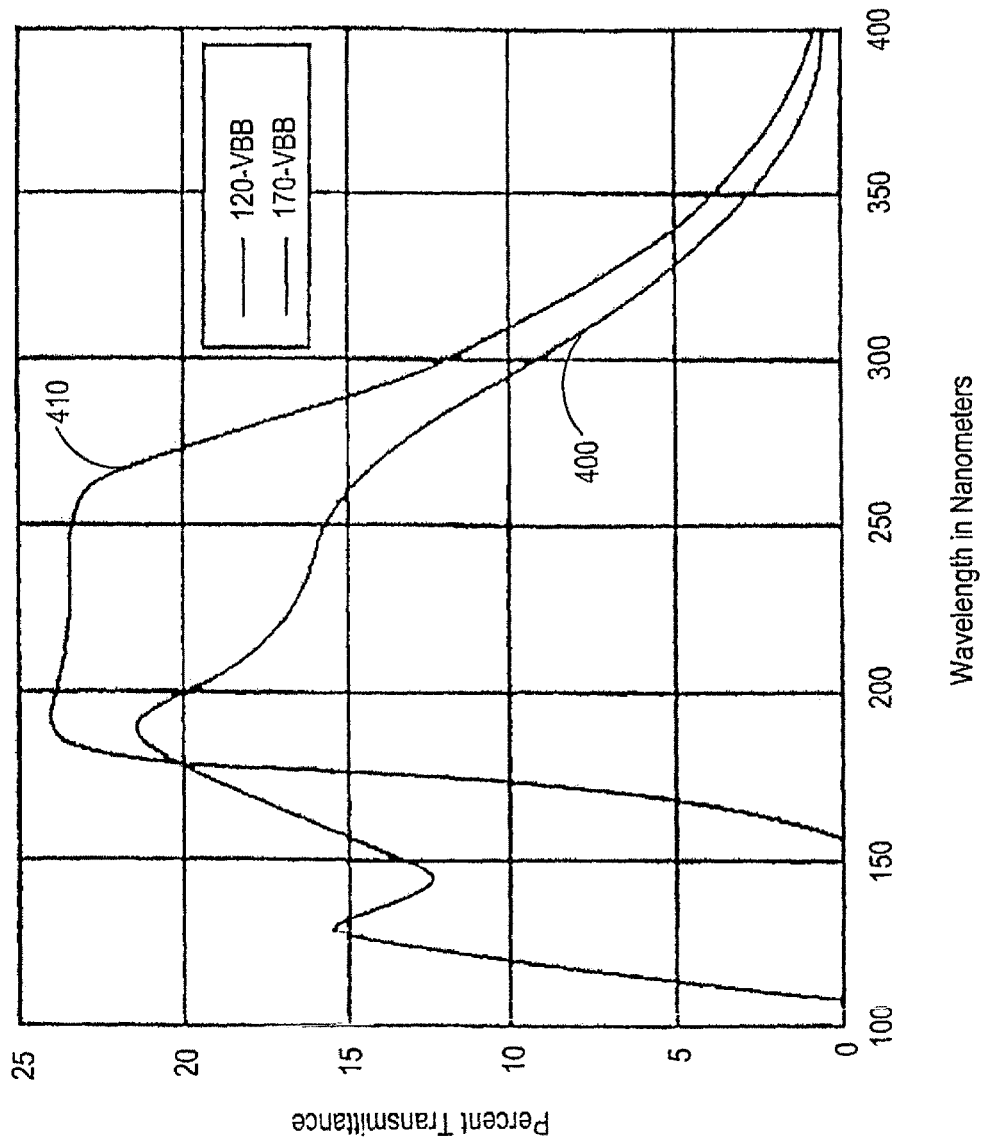
FIG. 4—"Solar-blind" broad-band VUV filter from Acton Research Corporation.

Referring again to FIG. 2, the beam conditioner module 220 allows for the introduction of spatial and/or spectral filtering elements to modify the properties of the source beam. While this functionality may not generally be required, there may arise specific applications where it is deemed advantageous. Examples could include modifying the spatial or temporal coherence of the source beam through use of an aperture, or introduction of a "solar blind" filter to prevent longer wavelength light from generating spurious VUV signals through scattering mechanisms that may occur at the various optical surfaces in the optical beam path. In a particular embodiment of the device the "solar blind" filter is a VUV filter from Acton Research Corporation, typical reflective properties of which are presented in FIG. 4 as shown by plot 400 for the Acton Research part number 120-VBB filter and plot 410 for an Acton Research part number 170-VBB filter.

Figure 5:
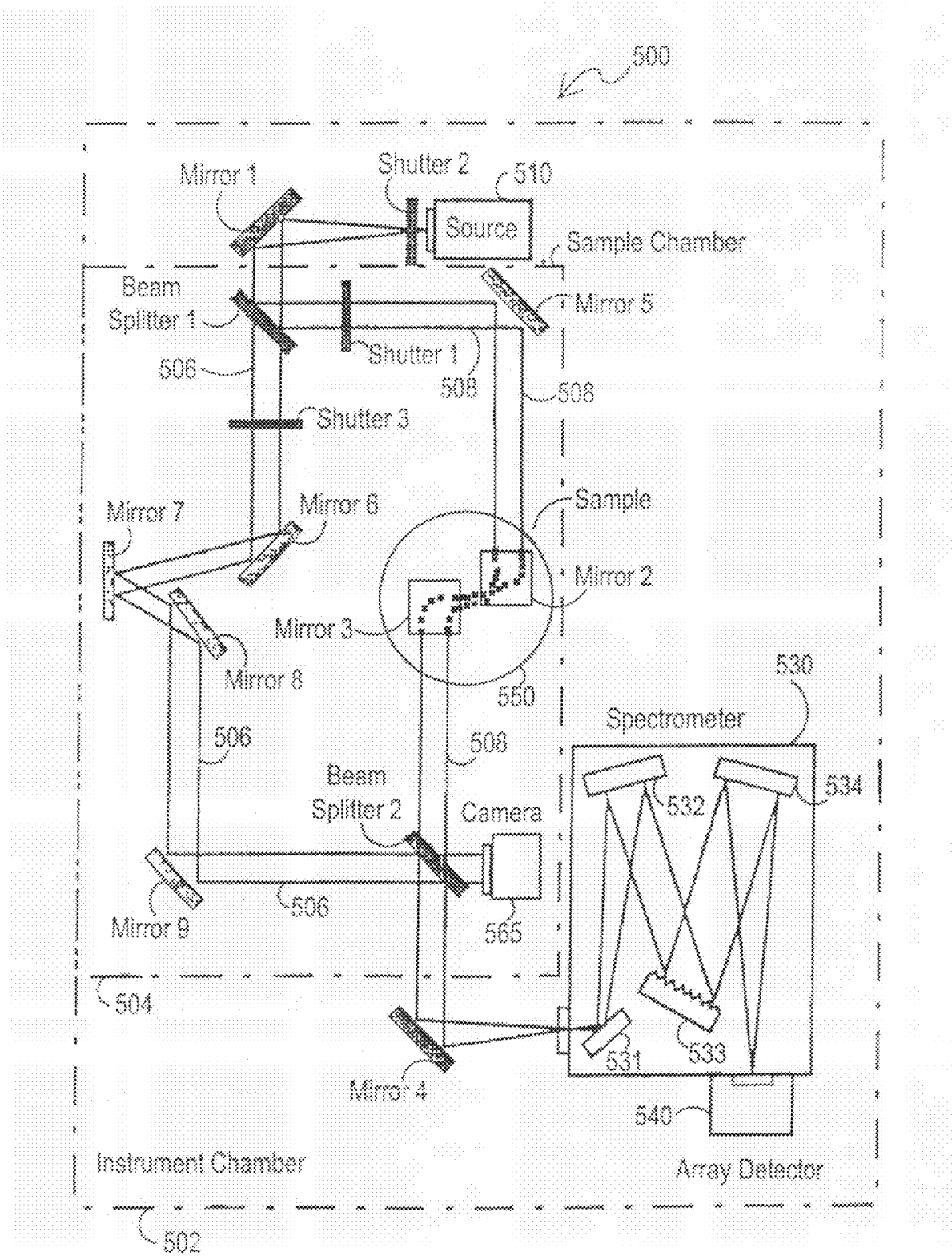
FIG. 5—Top-down schematic view of VUV reflectometer illustrating incorporation of reference channel.

A more detailed diagram of one embodiment of an optical reflectometer metrology tool 500 is provided in FIG. 5, wherein the optics comprising the measurement and reference channels of the device are illustrated in more detail. Though not shown, it will be recognized that the optical reflectometer metrology tool may include the components shown in FIG. 2 such as the purge or vacuum system 280, processor 290, stage 270, etc. As shown in FIG. 5, a source 510, spectrometer 530, and array detector 540 may be provided in an instrumentation chamber 502. A sample chamber 504 is coupled to the instrumentation chamber 502 through coupling mechanisms (not shown).

Referring again to FIG. 5 the optical path for a sample measurement will be described. It is seen that light from the source 510 is collimated and directed by Mirror 1 towards Beam Splitter 1, where the source beam is split into sample and reference beam components (generally indicated by beams 508 and 506 respectively). The sample beam 508 is reflected from the beam splitter 1 towards plane Mirror 5, where it is redirected towards Mirror 2. Here the light is focused down (into the plane of the figure) onto the sample 550. The reflected light (out of the plane of the figure) from the sample 550 is captured by the collimating optic (Mirror 3) where it is directed through Beam Splitter 2 towards the focusing optic, Mirror 4. Here the light is then focused onto the entrance plane of the spectrometer 530. During measurement of the sample Shutters 1 and 2 are open while Shutter 3 remains closed.

Figure 6:
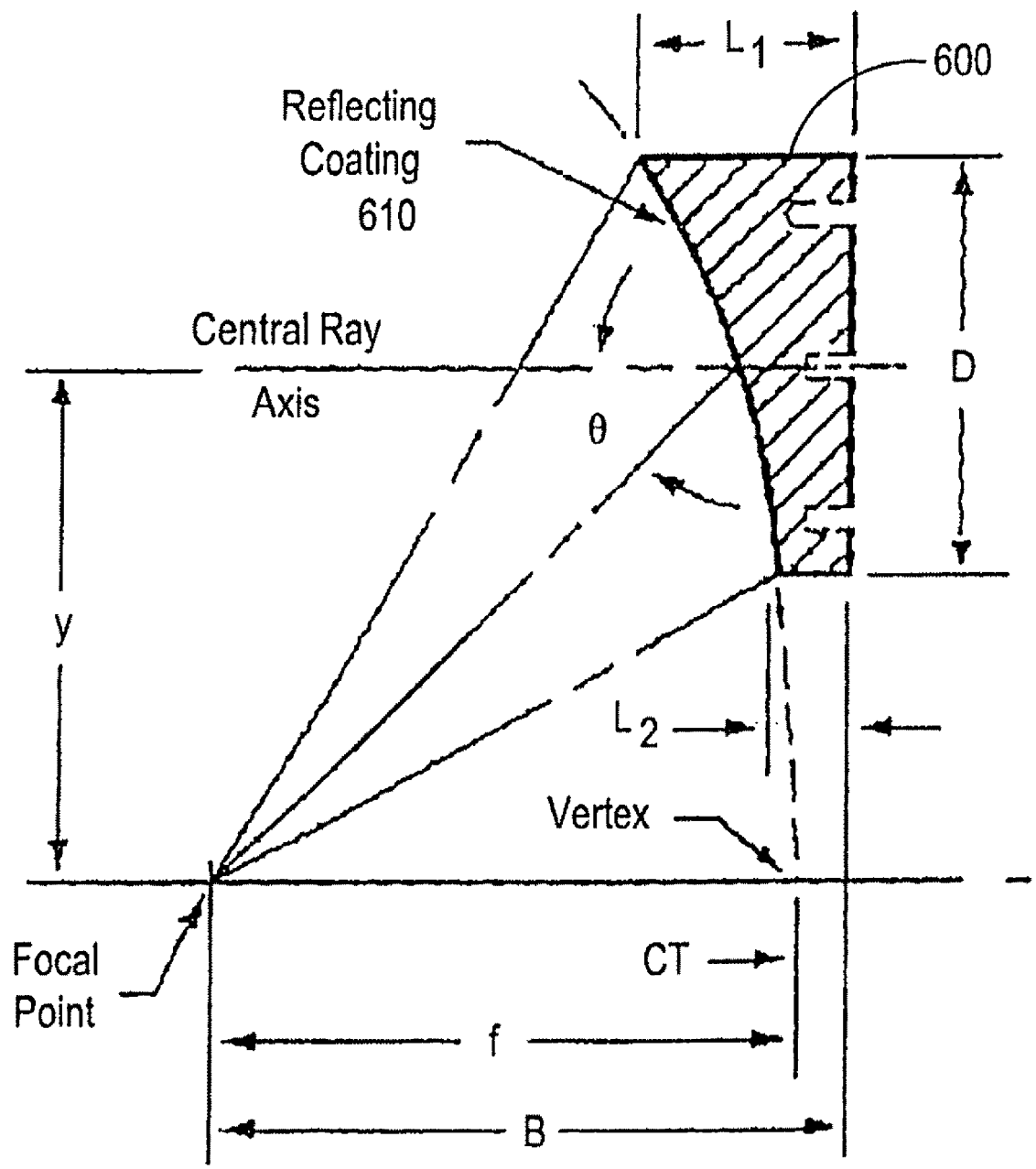
FIG. 6—Typical off-axis parabolic mirror.
Figure 7:
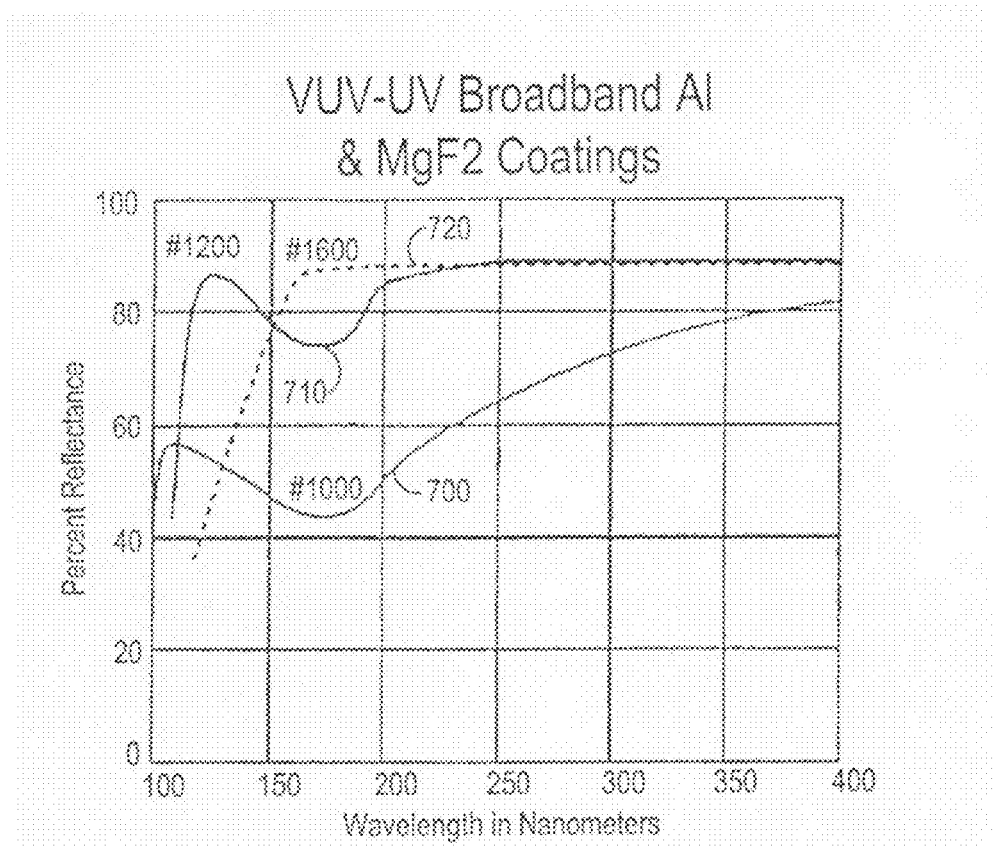
FIG. 7—Broad-band VUV-UV reflective coatings from Acton Research Corporation.

In one embodiment, the mirror 1, mirror 2, mirror 3 and mirror 4 are off-axis parabolic reflectors; an example of such is depicted as off-axis mirror 600 in FIG. 6. These mirrors are preferably polished using conventional techniques following their manufacture and then covered with some form of broad band reflective coating 610 like Al/MgF$_2$ (some manufacturers may implement aluminum and MgF$_2$ layers directly on each other on the mirror or alternatively thin layers of other materials may be located under or over the aluminum layer). Post polishing improves the imaging properties of the mirrors by minimizing issues arising from diamond turning artifacts. The broad band coating 610 is tailored to enhance the reflective properties of the mirrors in the VUV. Examples of particularly well-suited coatings for coating 610 are produced by Acton Research Company. FIG. 7 illustrates reflectance plots for coating #1000, #1200, and #1600 produced by Acton Research Corporation (plots 700, 710 and 720 respectively). For operation at shorter wavelengths other coatings like elemental iridium may be better suited.

Figure 8:
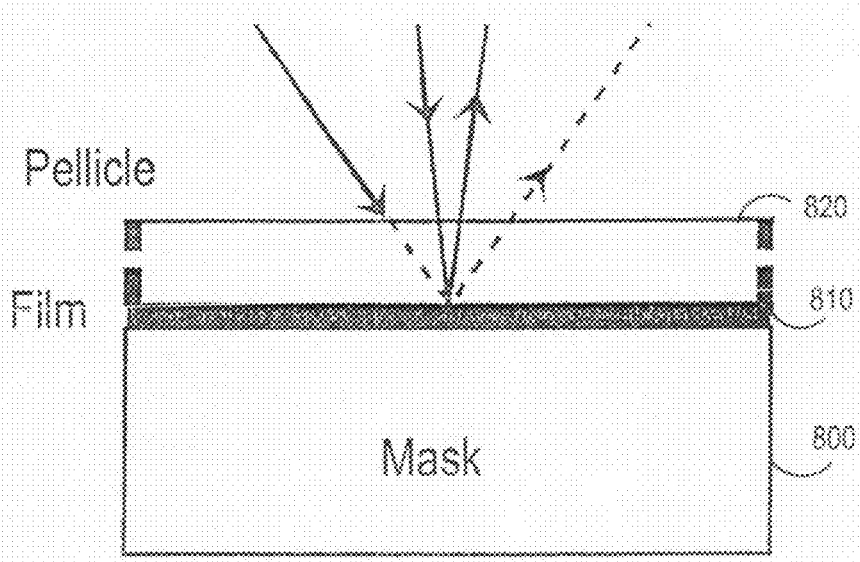
FIG. 8—Example of "through-pellicle" measurement using shallow angle (solid line) and large angle (dashed) incidence configurations.

While other types of mirrors could also be incorporated into the system, the use of off-axis parabolic reflectors enables reflectance data to be obtained using near-normal incidence illumination/collection yielding numerous benefits. These advantages include simplifying the subsequent analysis of measured data since polarization effects can be neglected, yielding symmetric illumination of measurement regions on the sample, minimizing scattering effects at the sample surface encountered using larger angles of incidence and facilitating compact system design, an important consideration for integrated and/or in-line metrology applications. Additionally, certain optical measurements may themselves benefit from use of a near-normal configuration. Typical examples include, but are not limited to, dimensional characterization of high aspect ratio features using scatterometry methods and through-pellicle measurements of photo masks. For example as shown in FIG. 8 and known in the art, a semiconductor photolithography mask substrate 800 may have a film (or films) 810 that is (are) protected by a pellicle 820. Measurements of the through pellicle measurements of the film (films) 810 may benefit from the use of a near normal configuration.

Off-axis parabolic mirrors are regularly produced by a variety of optics manufactures; they are as such, readily available and relatively inexpensive. They offer greater degrees of freedom, with respect to integration and alignment, and do not suffer from astigmatism to the same extent as toroidal mirrors when used in similar applications.

In a particularly useful embodiment of the invention one or more of the off-axis parabolic mirrors is designed such that the off-axis angle (denoted as θ in FIG. 6) is equal to 90°. Such an arrangement provides considerable flexibility and reduced susceptibility to scattering at shorter wavelengths (a consequence of the smaller incident angles involved). Flexibility follows from the fact that rotation of one such optic about an axis parallel to the central ray axis of the optic maps out a two dimensional pattern (i.e. circle) as opposed to a three dimensional pattern (i.e. cone) for optics possessing other off-axis angles. This specific geometrical configuration offers a number of system enhancement possibilities and advantages.

An example of one such enhancement would be to enable simple incorporation of multiple sources into the system. Other sources could be placed at appropriate locations around an axis perpendicular to the central ray axis of the optic. To select another source it would then only be necessary to rotate the optic around the axis. Another advantage of such an arrangement would be realized during the initial alignment phase of the instrument. Using a normal incidence configuration would enable simple determination of proper alignment on both the illumination and collection arms of the tool since they would be working on-axis, in the sense that they would be focusing onto a surface perpendicular to central focusing. This results in better spot definition and hence, better overall imaging performance.

Referring again to FIG. 5, once the light enters the spectrometer 530 it is reflected by a plane mirror 531, collimated by a focusing mirror 532 and incident upon a diffraction grating 533. Some portion of the light diffracted by the grating is collected by the second focusing mirror 534 and focused onto the surface of the VUV sensitive array detector 540. As is known in the art, the light that is reflected from the diffraction grating becomes spatially separated by wavelength across the width of the detector. It is noted that in this particular embodiment all of the optics inside the spectrometer have also been coated with broad band reflective coatings like Al/MgF$_2$ to increase their efficiencies. Ideally, the spectrometer is an imaging spectrometer that is designed in such a manner as to provide stigmatic imaging in a large area flat field as is the case with the 250 is/sm manufactured by Chromex Instruments (see also U.S. Pat. No. 4,932,768). Such spectrometers typically allow a wide range of multiple wavelengths to exit the spectrometer simultaneously for detection by the detector element (as opposed to some types of spectrometers which attempt to restrict the exiting light to a single wavelength). Typically, such spectrometers utilize a fixed diffraction grating since a moveable diffraction grating is not required to generate the data at varying wavelengths. The imaging spectrometer may be utilized in combination with an array detector such that the multiple wavelengths exiting the spectrometer may be spread across the width of the array detector. The columns across the width of the detector are thus presented with light of different wavelengths. The internal elements of imaging spectrometers may be designed such that the multiple wavelengths are sufficiently resolved so that the array detector may accurately obtain data for various wavelengths.

In addition, it is advantageous if the diffraction gratings are of the holographic ion-etched type so as to minimize stray light resulting from light scattering at short wavelengths. Alternate embodiments of the invention could also incorporate other types of VUV spectrometers including non-periodic toroidal grating configurations, like those manufactured by Jobin-Yvon of France, Rowland circle configurations, like those manufactured by Resonance Ltd. of Canada, or Echelette configurations like those manufactured by Catalina Scientific Corp. of the United States. In addition, the diffraction grating utilized need not be a movable but rather may be implemented as a fixed diffraction grating.

While any number of VUV sensitive array detectors could be used with the invention, it is desirable to use a detector that provides efficient conversion of VUV photons while offering a wide dynamic range. Back-thinned, back-illuminated, uncoated charge coupled devices (CCD's) are particularly well-suited for this application as they offer high sensitivity and avoid losses due to absorption of VUV photons in poly-Si gate regions as encountered by their phosphorus coated front-illuminated counterparts. Uncoated devices are generally expected to perform better over a wide range of wavelengths than those possessing anti-reflection layers. Another type of array detector that may be used is a micro channel plate detector coupled to a standard CCD or photodiode array (PDA). One example of a micro channel plate detector suitable for this application is manufactured by Burle Industries, Inc. of the United States. Alternatively, front-illuminated CCD's or photodiode arrays can independently be used if they are equipped with a phosphorus coating that absorbs short wavelength photons and re-emits longer wavelength photons that can then be effectively collected with the devices.

Another aspect of the array detector 540 is that it may be cooled to low temperatures (below 0° C.) to reduce dark counts (i.e. thermally generated carriers) which mask a measured signal and can adversely affect system accuracy in cases where low photon levels prevail. In order to cool the detector, it may be necessary to encapsulate it in a hermetically sealed chamber to prevent condensable species from accumulating on the device. This is usually accomplished by mounting the device in a vacuum chamber sealed with an MgF$_2$ window to permit VUV photons to pass. For operation at shorter wavelengths (generally below about 115 nm, the transmission cutoff for MgF2) the protective window could be removed as the controlled environment would be that of vacuum, rather than a non-absorbing purge gas. A particularly well-suited detector (Model #DV-420-BN) is manufactured by Andor Technology of Northern Ireland. This particular detector is an array detector that has a width of 26.6 mm and a height of 6.7 mm. Such a detector is formed of an array of pixels arranged as rows and columns. In this example a typical pixel may be 26 microns in width and height, though detectors with smaller resolutions on the order of 10 microns are also typically available.

To aid in the selection of discrete measurement locations on patterned samples an optional camera system 565 (i.e. camera plus necessary focusing elements) could be employed. While there are numerous ways in which to integrate such a system into the reflectometer arrangement, one possible method is to use it to capture the beam passing through the sample channel 508 and reflecting from Beam Splitter 2. When utilized in this manner, the camera system 565 could be used to collect images at any time the sample channel 508 is in use (i.e. when Shutter 1 is open). Alternatively, a flip-in mirror could be added to the camera system to temporarily redirect some portion of the sample beam (following reflection from the sample) to the camera. Finally, there is also the option of introducing separate illumination and/or collection optics to the reflectometer in order to acquire images and locate specific features on the sample.

The use of an imaging spectrograph, in combination with an array-based detector, enables entire spectra to be collected much faster and to a higher degree of accuracy (due to lack of moving parts) than with a conventional scanning monochromator and single element detector arrangement. In addition, it enables high quality imaging reflectometry, allowing data from small regions on the sample to be readily collected and spatially resolved. This permits measurements to be performed on actual patterned production samples and not just on blanket "test" substrates or wafers. In fact, the combination of imaging optics and a highly sensitive detection system enables multiple measurements to be performed simultaneously on a series of sites within a localized region.

Figure 9:
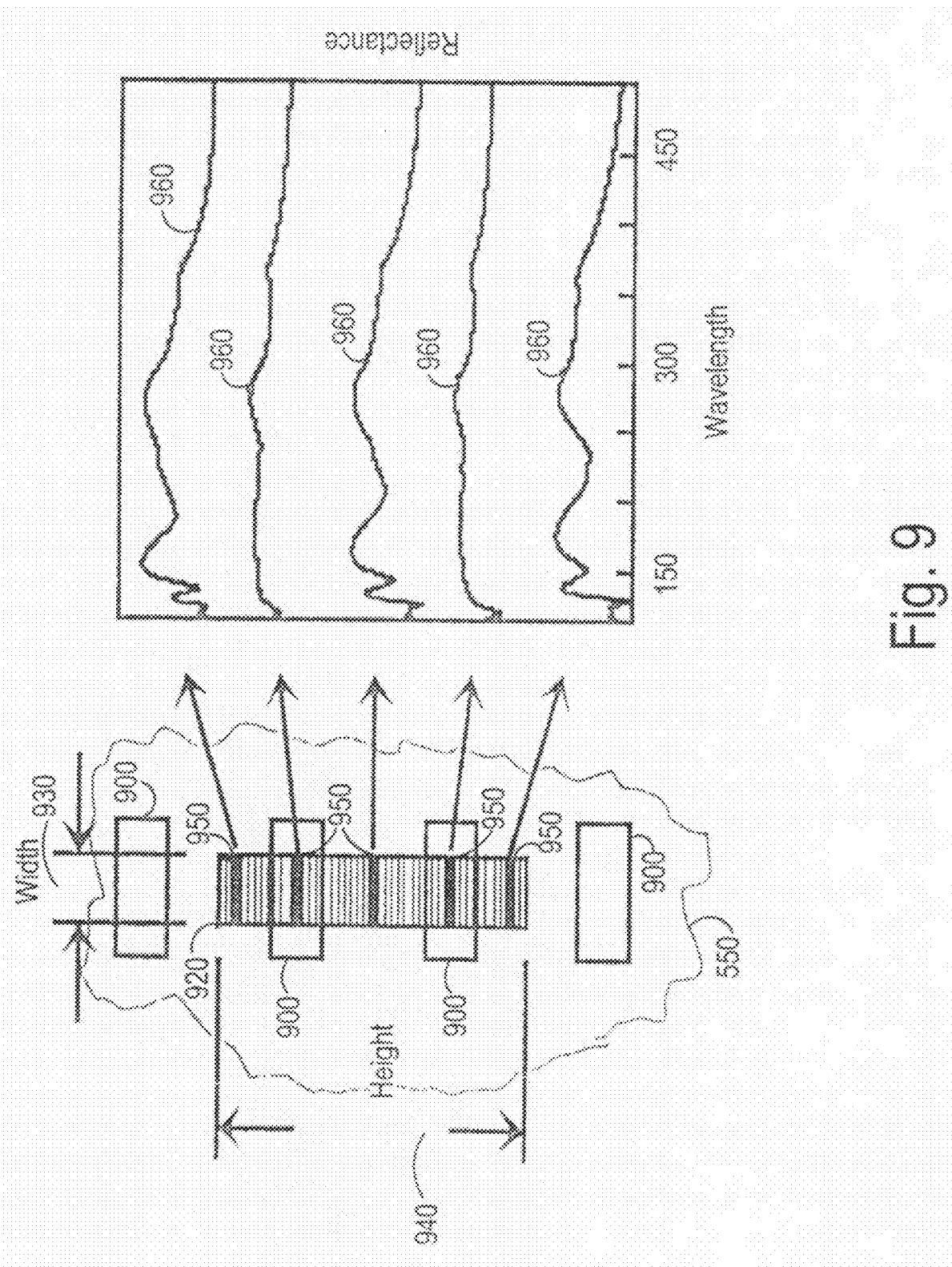
FIG. 9—Use of imaging reflectometer to simultaneously record multiple spectra from different physical locations on patterned sample.

FIG. 9 illustrates the fashion in which such multiple measurements are achieved. These techniques take advantage of the chosen detector being a two-dimensional array detector. Thus for example with regard to FIG. 5, the array detector 540 may be a two dimensional array detector. The left hand side of the FIG. 9 presents a portion of a patterned sample 550 wherein with four rectangular structures 900 formed. For example, such structures 900 may be formed on a semiconductor substrate such as patterned polysilicon structures, metal structures or other structures formed on semiconductor wafers. The structures 900 may be surrounded by an unpatterned region of the semiconductor substrate (it will be recognized that the structures shown are illustrative only to aid in the understanding of the invention and portions or structures of a sample may be subject to simultaneous multiple measurements as described herein). Superimposed on the middle two features of the sample is vertical rectangle 920 defining the spatial region that is imaged onto the spectrometer's entrance slit. While a significantly larger region may actually be illuminated on the sample, only the light reflected from the specified area will be collected by the spectrometer and hence recorded by the detector. The width and height of this region are a function of the slit width 930 and slit height 940 of the spectrometer entrance slit in combination with the supporting collection and illumination optics chosen. Exemplary slits may have widths on the order of 20-30 microns and heights on the order of 1 centimeter. As shown in the example of FIG. 9, the sample and slit may be considered as formed of rows and columns (a row being from left to right on the page such as rows 950, and columns being from top to bottom on the page). The information from the sample that passes through the entrance slit of the spectrometer is then diffracted by the diffraction grating and then presented to the array detector. The row information of the sample physically maps to rows on the detector, however, the column information does not as the diffraction grating disperses the column information such that given wavelength components originating from all columns will map to a single column on the detector. As a result, data corresponding to different vertical positions (i.e. rows) on the sample are imaged onto different vertical positions (rows) of the detector.

As the detector is comprised of a series of pixel rows (typically 256, 512 or 1024) each individual row of pixels will record data corresponding to different discrete locations on the patterned sample. This point is illustrated on the right hand side of FIG. 9 which presents reflectance spectra plots 960 collected from five separate row sites 950 on the sample 550. Thus, for any given row site 950 of sample information a spectra plot for a range of wavelengths may be obtained. Moreover, the array detector may simultaneously collect information from multiple separate row sites 950. Thus, data for multiple wavelengths and for multiple row sites may be simultaneously collected. The resolution of the individual rows of sample sites that may be detected is dependent upon the pixel height utilized in the array detector. Through selection and/or adjustment of collection and illumination optics, entrance slit width and detector binning configurations, a range of measurement sites of various sizes may be achieved. In this fashion a two dimensional region of a sample may be illuminated by the optical path and the data from the two dimensional region may be recorded on the two dimensional array detector. As shown in the spectra plots 960 of FIG. 9, such techniques may be utilized to characterize the sample structures 900 and/or distinguish the sample structures 900 from unpatterned regions of the sample. Further, though the slit width is shown as mapping a given row only upon the sample structure 900, the sample may be moved (left or right in the figure) such that the a given row of the slit width overlaps both patterned and unpatterned regions thus provided data indicative of a combination of both regions.

The ability to simultaneously collect data from a number of discrete locations within a given localized region provides advantages with regards to measurement throughput since a significant portion of measurement time per site in a conventional instrument results from sample placement (i.e. precise adjustment and positioning of sample sites into measurement location). Additionally, this unique capability may also prove useful in applications where comparative measurements between closely separated sites are of interest. Typical examples include, but are not limited to, dishing and erosion studies relating to chemical mechanical polishing applications. Thus, rather than having to take separate multiple measurements performed in conjunction with movement of the sample, a single measurement may return data that relates to multiple positions in a two dimensional area of the sample. It will be recognized that in such techniques the quality of the optical elements (such as mirrors, beam splitters, etc.) should be such that a larger distortion free area is provided as compared to applications in which two dimensional measurements are not being utilized. Thus, the optical VUV reflectometer system provided herein may also be characterized in one embodiment as a two dimensional reflectometer system. It will be recognized that many uses of such two dimensional data collection will advantageously be utilized with a camera element as described above such that pattern recognition of the two dimensional sample area that is being analyzed may occur.

The systems and techniques described herein are particularly advantageous for use in applications where a high speed measurement is desirable. In addition to the capability of obtaining data from a number of discrete locations within a given localized region, these measurements may be obtained without the need for slow step and scan techniques that utilize movable diffraction gratings.

As a result of the absorption issues discussed earlier, small environmental perturbations can significantly influence measured data at VUV wavelengths. Along these lines, it is desirable to provide an apparatus which can perform measurements in a short time period in order to minimize deleterious effects resulting from environmental changes occurring during the measurement process. Furthermore, it is desirable to provide a means by which the measured data can be referenced to a known standard for the purposes of data normalization. Additionally, the means of referencing should be such as to further minimize and/or eliminate altogether errors introduced by data altering environmental changes which may occur between the conclusion of a calibration measurement and the commencement of subsequent sample measurements.

Referencing is necessary to ensure that changes in the system (i.e. output of source, environmental conditions, etc.) are properly accounted for and do not result in inaccurate data. While essential to ensure stability of reflectometry results in any wavelength regime, referencing is of more importance when operating in the VUV due to the lower available photon flux and the heightened sensitivity of the recorded data to the composition of the gaseous medium contained within the optical path.

Referring again to FIG. 5, in the VUV apparatus describe herein, data referencing is accomplished through use of a reference beam channel 506. As described more herein, it is desirable that the reference beam channel be balanced (or of the same beam length) as the source beam channel 508. This reference beam channel 506, illustrated in FIG. 5, is created at Beam Splitter 1 as the source beam is split into sample and reference components. This beam is transmitted through the beam splitter and reflected off Mirrors 6, 7 and 8 before reflecting off Mirror 9. The beam then reflects off Beam Splitter 2 to thereafter follow the identical path to the detector as described for the sample beam channel 508 earlier. Controllable apertures may be utilized to selectively enable or disable the reference beam channel and the sample beam channel. For example, the apertures may be formed from controllable optical shutters. During the reference measurement Shutter 1 is closed, while Shutters 2 and 3 remain open.

Figure 10:
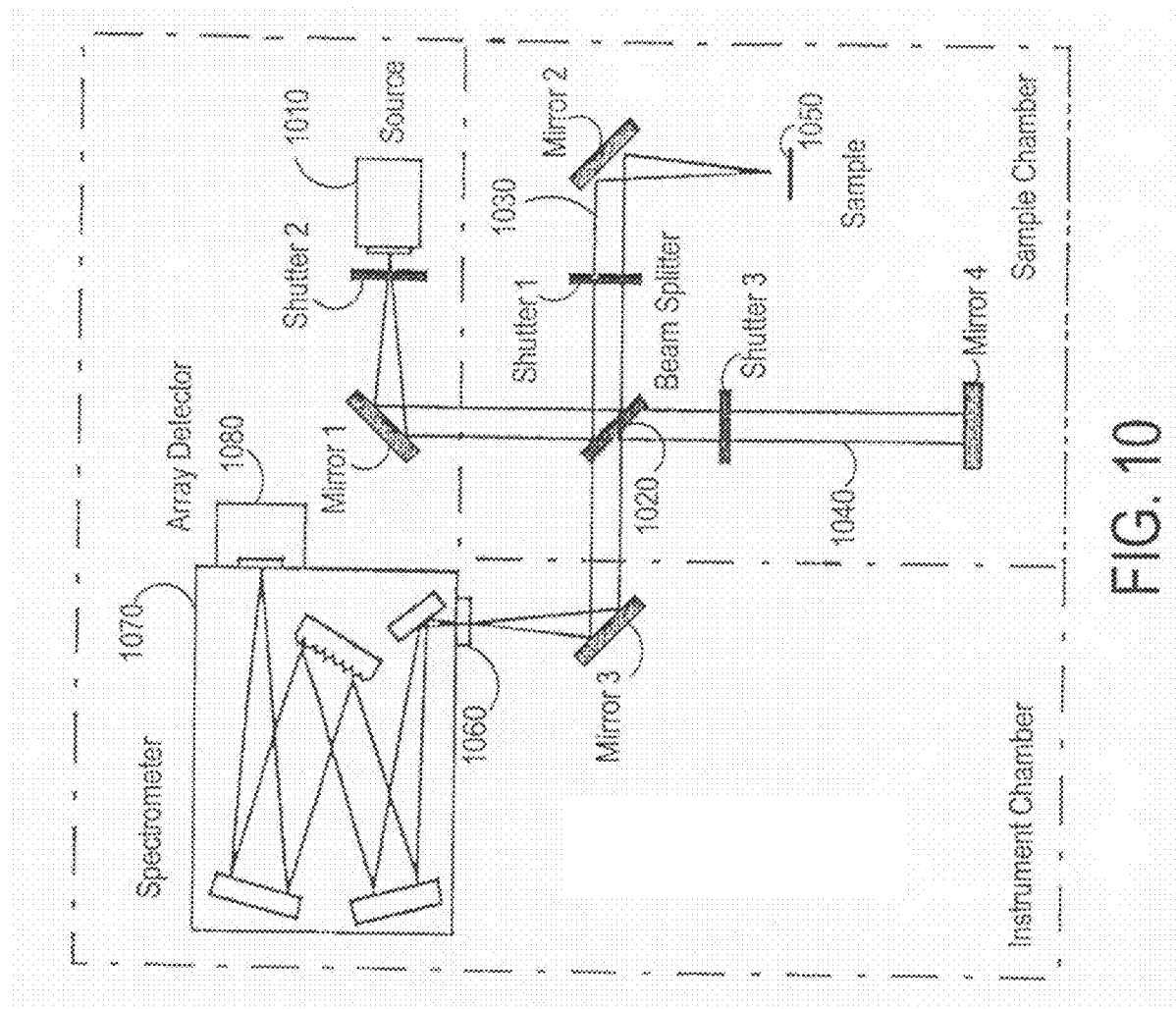
FIG. 10—Schematic view of alternate VUV reflectometer with reference channel.

To one skilled in the art it will be apparent that if the optical paths traveled by the sample and reference beams from Beam Splitter 1 to Beam Splitter 2 are precisely adjusted such that they are near-identical in length they form the two arms of a near-balanced Mach-Zehnder interferometer. It will also be readily apparent that there exist many other equivalent arrangements incorporating other interferometer designs for achieving this objective. An example of one such alternate embodiment is illustrated in FIG. 10, wherein a Michelson interferometer is incorporated into the design. Though not shown other elements of the systems of FIG. 2 or 5, such as coupling mechanisms, a camera, a purge or vacuum system, a processor, etc. may be incorporated with the use of the system of FIG. 10. In the arrangement of FIG. 10, light from the source 1010 is collimated by Mirror 1 and directed towards the Beam Splitter 1020 where the sample beam 1030 and reference beam 1040 are split. The sample beam 1030 travels through Shutter 1 and is focused onto the sample 1050 by an off-axis parabolic reflector (Mirror 2). Light from the sample is captured by the same optic and travels back along its original path. The beam then travels through the Beam Splitter 1020 and is focused onto the entrance slit 1060 of the spectrometer 1070 by another off-axis parabolic reflector (Mirror 3) and finally directed toward an array detector 1080. During the sample measurement Shutters 1 and 2 are open, while Shutter 3 remains closed.

During the reference measurement, the reference beam 1040 passes through the Beam Splitter 1020 and Shutter 3 before it is reflected back along its path by Mirror 4. It then reflects off the Beam Splitter 1020 and is focused onto the entrance slit 1060 of the spectrometer 1070 in a similar fashion to the sample beam. During the reference measurement Shutters 2 and 3 are open, while Shutter 1 remains closed.

The benefit of these reference configurations can be described as follows. As the attenuation of VUV photons due to absorbing atmospheric species is a function of optical path length (the longer the path, the more absorbing molecules encountered), and as the dependence is non-linear in nature, it follows that the sample and reference arms should be substantially of the same length if similar attenuation effects are to be encountered by each beam. If this is not the case, and the arms are of different lengths, then data taken at any time following a calibration measurement will only be accurate if the concentration of absorbing species in the environment is precisely identical to that present when the calibration measurement was performed. As this condition is virtually impossible to ensure it remains highly improbable that accurate results can be obtained unless the sample and reference path lengths are equal.

As described in more detail below, providing a reference beam allows for measurements to be obtained that indicate conditions of the optical reflectometer system. For example, the presence of absorbing gases within the optical reflectometer system can greatly affect the data obtained from a particular sample. The reference beam channel provides a mechanism that is indicative of environmental or other system conditions. The data obtained from the reference channel may then be utilized to adjust or correct the data obtained from a sample. Thus, the use of a reference beam to provide a mechanism to indicate the environmental conditions of the optical path allows for increased accuracy in calculations made from the data obtained from the optical metrology system. In addition, the use of a reference beam may allow suitable sample data to be obtained over a wide range of environmental conditions, thus lessening the environmental criteria, particularly for lower wavelength measurements.

In addition to ensuring that highly accurate reflectance data is obtained, the reference channel arrangement also provides a number of other direct benefits. Firstly, the referencing scheme extends the range of acceptable environmental operating conditions over which reliable and accurate data can be obtained. Quite simply, as long as the concentration of absorbing species is sufficiently low enough to permit a measurable fraction of VUV photons to leave the source, reflect from the sample and reach the detector, accurate measurements can be performed. This reduces the requirements on the controlled environments and makes data collection over a wider range of conditions possible. In essence the reference method enables accurate measurements to be performed over a wide range of suitable, as opposed to reproducible, environments. As well, the interferometer approach herein described, not only balances the path lengths of the channels, but also acts to balance the spectral intensity profiles seen by the detector. This is important as it allows for longer integration times and helps to mitigate any non-linearity effects which may be inherent to the detector.

Figure 11:
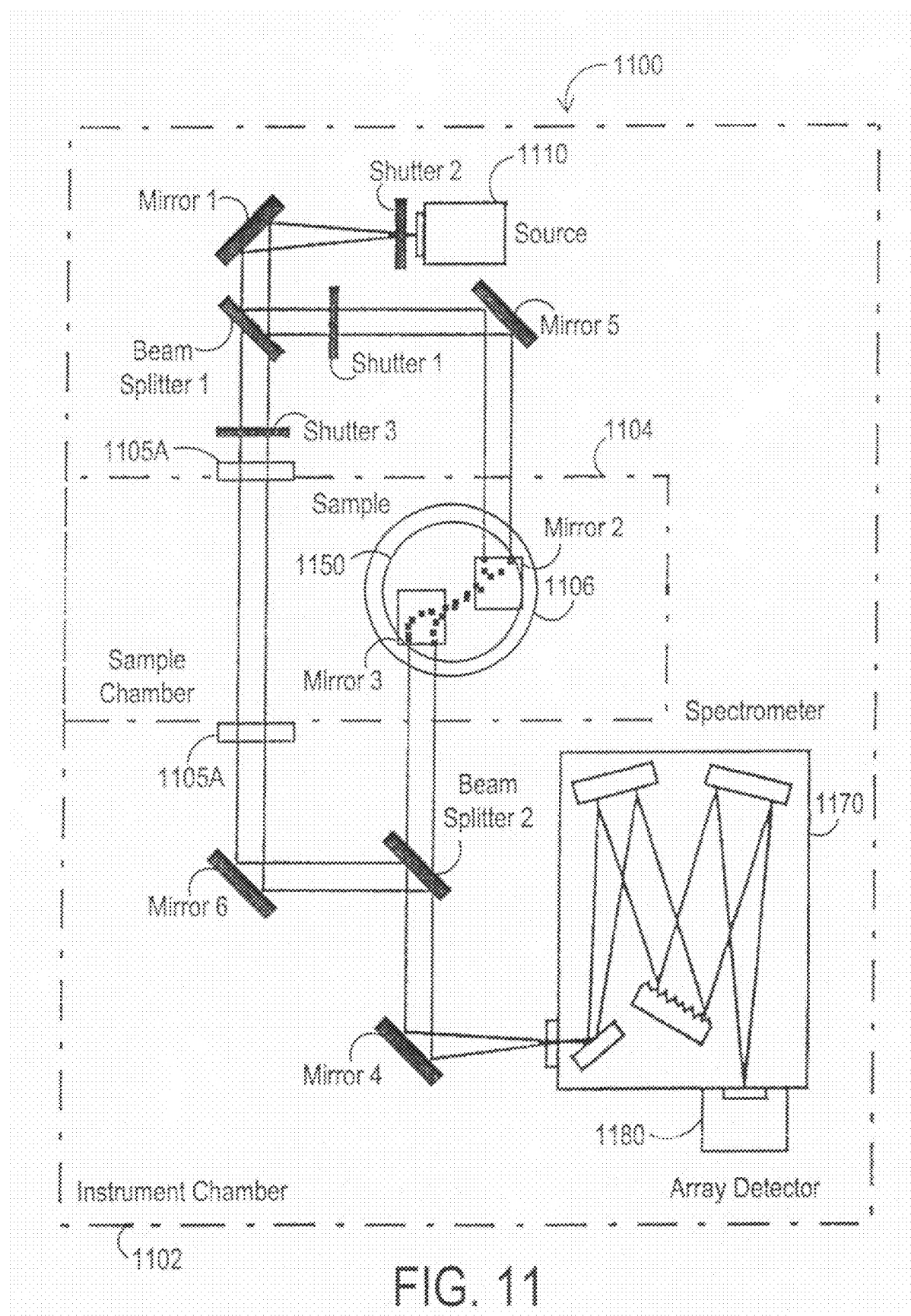
FIG. 11—Schematic view of alternate VUV reflectometer with virtually all optics housed within instrument chamber.

In yet another embodiment of the invention virtually all of the optical elements, with the exception of the sample itself, are housed within the instrument chamber. This configuration, illustrated in FIG. 11, significantly reduces the spatial requirements of the sample chamber, rendering it well suited to integrated process control applications. As shown in FIG. 11, an optical reflectometer metrology tool 1100 is provided. A source 1110, spectrometer 1170, and array detector 1180 are provided within an instrument chamber 1102. Also provided within the instrument chamber are all of the optical elements of both the sample beam path and the reference path. Thus, mirrors 1-6, and shutters 1-3 are all located within the instrument chamber 1102. Mirror 2 focuses the beam down (into the plane of the figure) through a coupling mechanism 1106 into the sample chamber 1104. From the sample 1150, the sample beam then travels up (out of the plane of the figure) through the coupling mechanism to mirror 3. As shown in FIG. 11, the reference beam path passes through two coupling mechanisms 1105A (such as windows or gate valves) that couple the reference beam from the instrument chamber 1102 into the sample chamber 1104 and back into the instrument chamber 1102. In this manner the reference beam is subjected to the environment of the sample chamber just as the sample beam is. Ideally, the distance that the reference beam travels in the sample chamber 1104 will match the distance that the sample beam travels in the sample chamber. Further, it will be noted that the reference beam passes through a coupler mechanism twice just as the sample beam does. Thus, the optical path of the reference beam is designed to closely simulate the conditions of the sample beam. In this manner, the optical paths of the reference beam and the sample beam are similar both overall and with regard to the individual paths in the instrument chamber and the sample chamber. It will be recognized that the path and arrangement on coupling mechanism shown in FIG. 11 is exemplary and other paths and arrangements may be utilized while still achieving the benefits described herein.

Figure 11A:
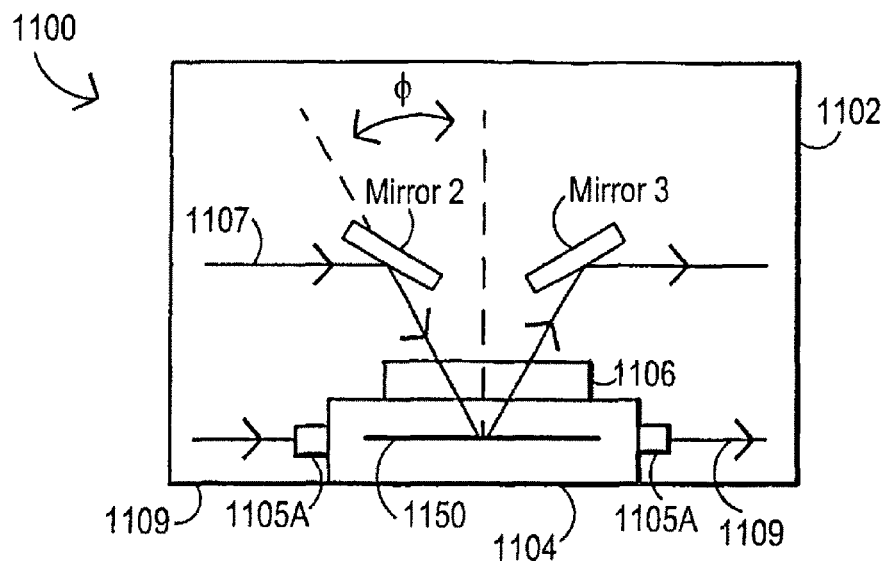
FIG. 11a—Alternate schematic view of the system of FIG. 11.

FIG. 11a illustrates the FIG. 11 arrangement of the instrument chamber 1102 containing mirrors 2 and 3, the coupling mechanism 1106, and the sample chamber 1104 that contains the sample 1150. As shown in FIG. 11a, the sample beam 1107 and the reference beam 1109 travel through the sample chamber 1104. It will be recognized that although perhaps less desirable, a system may be configured such that the reference beam does not pass through the sample chamber. Such a configuration may be utilized, for example, when the path length traveled by the sample beam in the sample chamber is sufficiently short and where the concentration of absorbing species in the sample chamber are sufficiently well-controlled, with respect to an initial calibration time and a later sample measurement time, so that errors introduced by such a configuration are within an acceptable error tolerance. In such a case, the reference beam may be configured so that both the reference beam and the sample beam travel the same optical distance in the instrument chamber. As the reference beam only travels in the instrument chamber the total beam path will thus be different. In this manner the environment that the two beams are subjected to are still generally matched (except with regard to the path length in the sample chamber). This condition may be realized in cases where the sample chamber is purged with a high quality non-absorbing gas or where it is evacuated using high vacuum equipment.

Figure 11B:
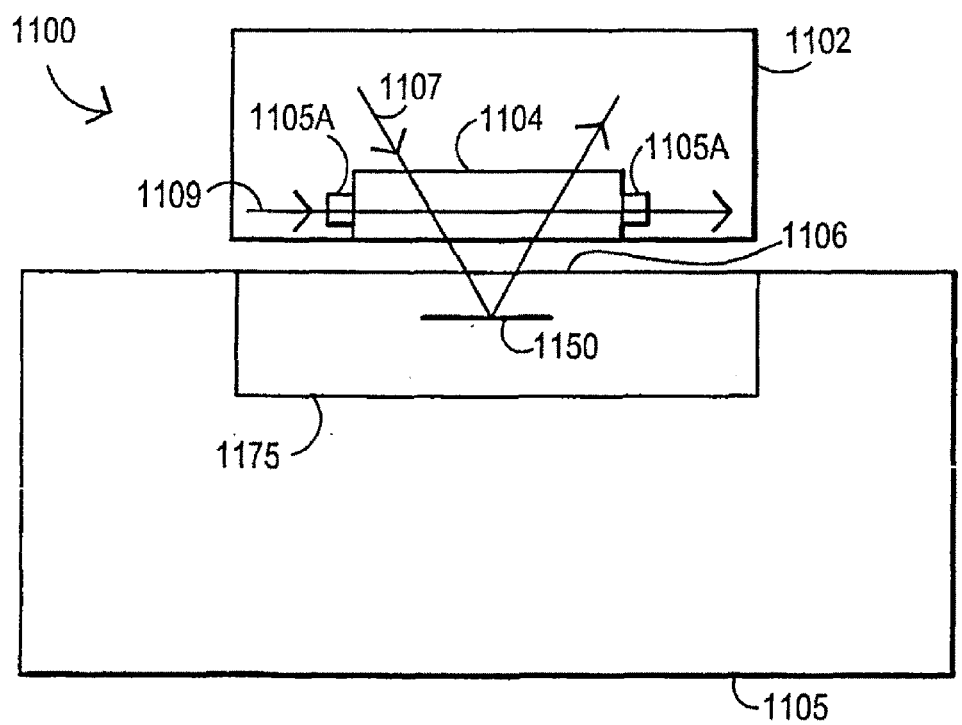
FIG. 11b—Schematic view of a system of FIG. 11 integrated with a process tool.

The systems of FIG. 11 and FIG. 11a may be utilized as stand-alone tools or may be integrated with another process tool. In one embodiment, the system of FIG. 11a may be merely attached to a process tool with some mechanism that allows for transport of the sample between the process tool and the metrology tool sample chamber. FIG. 11b, however, shows an alternative manner for integrating the optical reflectometer metrology tool with a process tool. As shown in FIG. 11b, the instrument chamber 1102 is coupled to a coupling mechanism 1106. The coupling mechanism 1106 may be for example a window. In this case the coupling mechanism 1106 may be a gate valve that is formed on a process tool 1105 or some other mechanism that allows the environment of the process tool 1105 to be shared with the sample chamber 1104. As shown in FIG. 11b, the sample 1150 need not leave the environment of the process tool, rather the sample 1150 may be contained within a region 1175 of the process tool. Region 1175 may be a processing chamber, a transport region or other region within the process tool. In the example shown, when the coupling mechanism 1106 (such as a gate valve) is opened, the environment between the region 1175 and the sample chamber 1104 is shared (note although called a sample chamber, sample chamber 1104 never receives the sample but rather has an environment that is shared with the region that contains the sample). Alternatively opening the coupling mechanism may be considered to effectively expand the sample chamber 1104 to include the region 1175. In this manner environmental conditions such as the concentrations of absorption species may be similar between the region 1175 and the sample chamber 1104. The beam paths for the reference beam 1109 and the sample beam 1107 may be again designed to be of similar length within the common environment of the region 1175 and the sample chamber 1104. The mechanism of FIG. 11b is also advantageous in that integration may be accomplished with the sample tool by providing a single simple coupling mechanism, such as a gate valve. As noted above, if the environment within the region 1175 can be closely controlled, it may be possible to achieve measurements within an acceptable error tolerance without sharing the environment between the sample chamber and the region 1175. In such a case, the coupling mechanism 1106 may be a window and the metrology tool would not need a sample chamber 1104.

The process tool 1105 of FIG. 11b may be any type of sample processing mechanism, such as for example, a deposition process tool, an etch process tool, a photolithography process tool, a planarization process tool, etc. In this arrangement, the sample will be contained within the process tool 1105. The process tool may contain a sample that is located in an optical path that may be accessed by the beam through the coupling mechanism 1106. The sample may be a located in a process tool sample chamber that is dedicated for use for metrology measurements or may be located within some other region of the process tool. In the configuration of FIG. 11b, the optical reflectometer metrology tool 1100 thus may be a separate add on unit that is comprised of an instrument chamber 1102 (and associated elements) that may be connected to a process tool 1105 that has a coupling mechanism 1106. The configuration of FIG. 11b is advantageous in that the optical metrology tool is easily adaptable for use with a wide variety of process tools because the process tool manufacture need only provide a coupling mechanism on the process tool without having to incorporate significant metrology elements within the tool itself.

With the arrangements of FIGS. 11, 11a and 11b, the optical path length within the sample chamber can be quite short, relative to that enclosed within the instrument chamber. In a preferred embodiment the optical path in the sample chamber could be short within the range of microns. Alternatively, to ease design of the process tool the path could be much longer in the range of hundreds of centimeters. The longer the optical path, however, the more desirable it is to minimize the presence of absorbing features and thus increase the environmental demands placed upon the sample chamber. If a short optical path is utilized, the requirements on the quality of the sample chamber environment are reduced, thereby reducing settling times and increasing sample throughput. A further benefit arises as optical surfaces housed within the continuously maintained instrument chamber are less susceptible to contamination than if they were resident in the cyclic environment of the sample chamber. While not explicitly denoted in FIG. 11, it is implied that the optical path lengths of the reference and sample beams are near identical either through judicious design of the sample chamber itself or by some other means of adjustment or positioning of the sample, or one or more of the coupling mechanisms between the sample and instrument chambers. FIGS. 11, 11a, and 11b illustrate the use of a sample chamber of reduced size. It will again be recognized that other features and elements of the systems of FIGS. 2, 5, 11, 11a, and/or 11b may be interchanged with each other even though all of such features or elements are not illustrated within the figures. Thus, for example an optical reflectometer metrology tool of FIG. 11 may utilize camera, a purge or vacuum system, a processor, a Michelson interferometer design, etc. and it will be recognized that the system shown in any particular figure is not limited to use with only those elements illustrated or the arrangement of the elements as shown.

Figure 13:
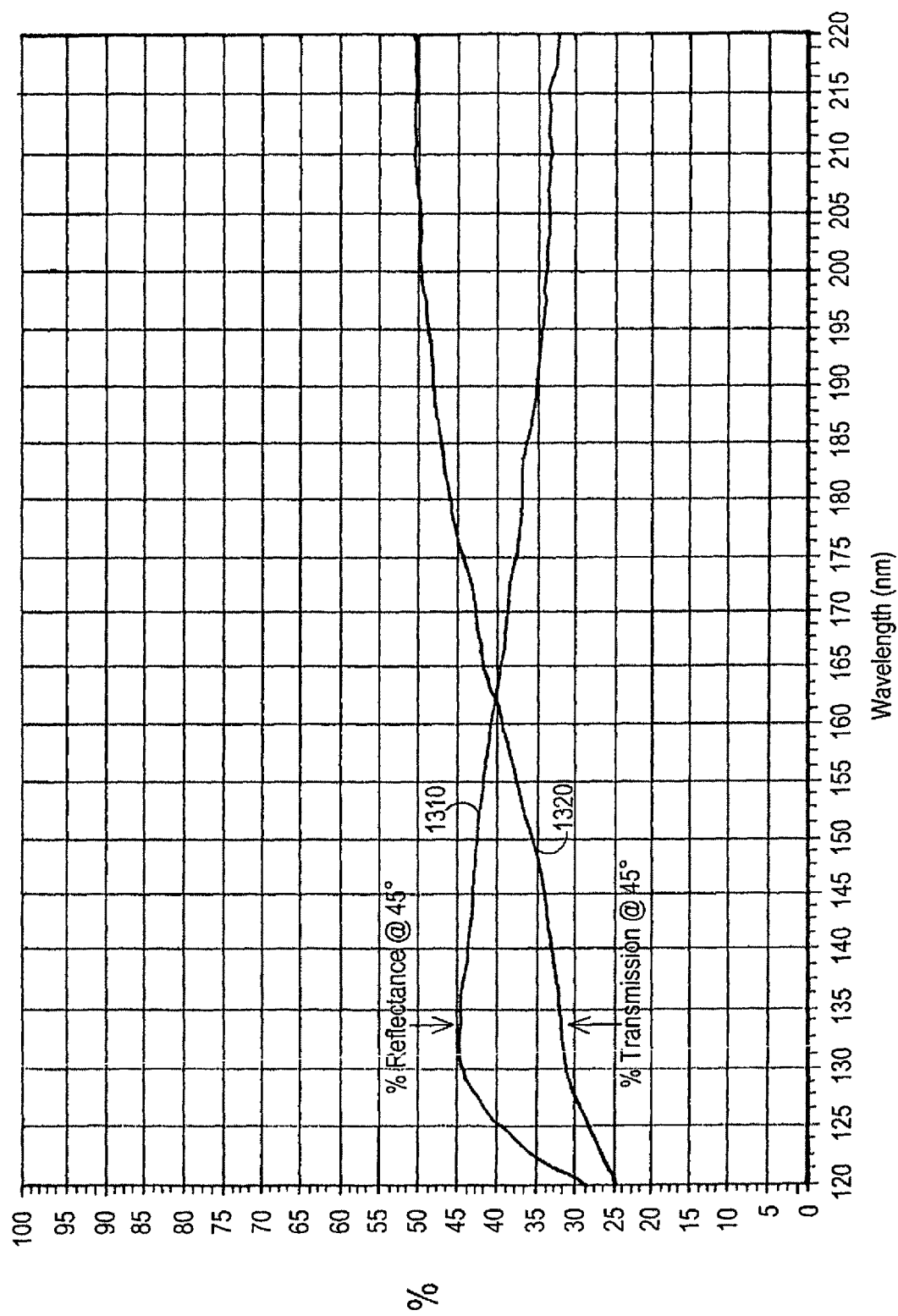
FIG. 13—Typical properties associated with VUV beam splitter manufactured by Acton Research Corporation.

The beam splitters employed in the device can be of various designs. For example, the beam splitters may be partially transmissive beam splitters that obscure the entire beam diameter or fully reflecting mirrors obscuring some portion of the entire beam diameter. If operation at wavelengths above 115 nm is desired and VUV photon flux is sufficient, then conventional thin film interference beam splitters employing $MgF_2$ substrates can be utilized. A particularly well-suited beam splitter for this application is produced by Acton Research Corporation (Model VUVBS-45-MF-2D). Typical reflectance and transmittance properties for this beam splitter are presented in FIG. 13 as plots 1310 and 1320. Plots 1310 and 1320 respectively illustrate the % reflectance at 45° and the % transmission at 45° as a function of wavelength. If operation at wavelengths below 115 nm is desired, or if photon levels are sufficiently low enough, a spatial beam splitter (totally reflecting mirror bisecting the optical path) or flip in mirror approach (replace Beam Splitters 1 and 2 with flip in mirrors and eliminate Shutters 1 and 2) can be used.

Figure 14:
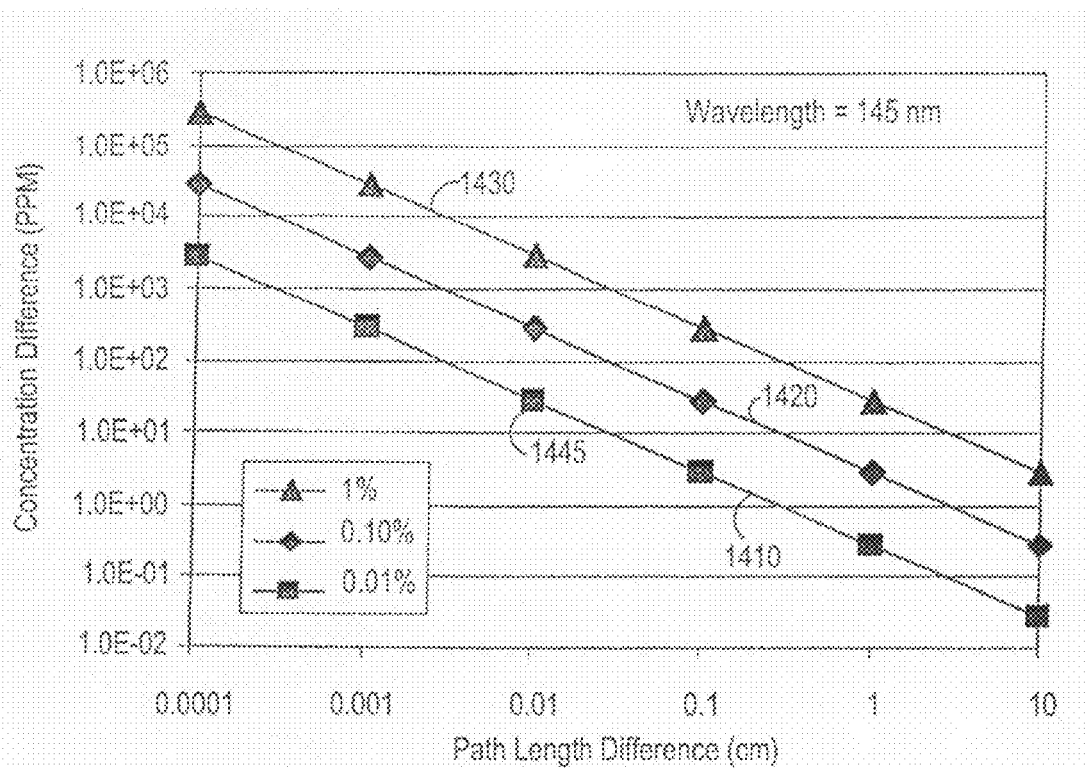
FIG. 14—Error plots as a function of concentration differences and path length differences.

Mirrors 6, 7 and 8 provide a means of adjusting the path length in the reference arm such that it closely parallels the path length in the sample arm such as for example as shown in FIG. 5. Those skilled in the art will recognize that there exist many alternate means of accomplishing this objective. For example, a configuration as shown in FIG. 11 may be utilized in which mirrors 7 and 8 are absent. The benefits associated with this effort are apparent upon examination of FIG. 14 where the difference in absorbance between the sample and reference arms is plotted for different path length differences and concentrations (in PPM) of $O_2$ and $H_2O$ contaminants. FIG. 14 plots the difference in concentrations of the contaminants from an initial time when the system is calibrated and at a later time when an unknown sample is measured versus the differences in path lengths of the sample and reference channels of the instrument. The plots 1410, 1420 and 1430 correspond to lines of absolute errors of 0.01%, 0.10%, and 1% that will be introduced in the measured reflectance data for a specific set of concentration and path length differences. Thus, for example, point 1445 illustrates that an approximate absolute error of 0.01% may result if the concentration difference between the time the calibration sample is measured and the time the sample measurement is measured is between 1.0E+01 and 1.0E+02 and the path length difference is approximately 0.01 centimeters. It will be recognized that FIG. 14 is an exemplary graph to demonstrate the principles described herein. For example the graph in FIG. 14 assumes that the $O_2$ and $H_2O$ change together (i.e. a concentration difference of 10 PPM corresponds to a 10 PPM change in $O_2$ and a 10 PPM change in $H_2O$). Further, it will be recognized that other contaminants that are absorbing species may be present. In addition, though FIG. 14 presents data at a wavelength of 145 nm, other wavelengths will similarly reflect the concepts described.

Thus if a particular application requires that errors be held below 0.1% and if the concentration of absorbing species in the sample chamber can be expected to change on the order of 100 PPM between the initial calibration and the final sample measurement time, then as reflected in FIG. 14 a maximum path length difference may be calculated. In the example presented, such path length difference may be less than about 0.025 cm. If the expected concentration differences are expected to be larger, the acceptable path length differences will be reduced. Likewise, if error must be held lower than the acceptable path length differences (for a given concentration difference) must be lower. It is noted that these effects are highly dependent upon the presence of absorbing species in the ambient and that the absorbance differences for a given path length difference increase non-linearly as the environment degrades.

While different applications can sustain different degrees of inaccuracy, it is likely that in many applications one would generally prefer to keep such errors less than 0.1% and in some cases below 0.01% or less. The range of concentration differences that could be encountered would depend to a large extent on how the instrument was designed and employed. For example, stand alone systems may be designed for use with adequate purge and/or vacuum control such that it is likely that concentration differences could be maintained at very low levels (on the single digit PPM level), whereas in integrated applications where the metrology instrument is attached to other process tools such as described with reference to FIG. 11b (and hence some fraction of the sample chamber resides within that other process tool), it may not be possible to control the differences.

During both the sample and reference measurements Shutter 2 of the embodiments described above with respect to FIG. 5, 10 or 11 acts to accurately control the duration of the measurement, which directly impacts the accuracy of the measured data. As such, Shutter 2 is preferably a high speed electronic shutter that can be precisely controlled on the millisecond timescale. An example of such a shutter is Model 76994 manufactured by Thermo Oriel of the United States. Shutter 2 also acts to prevent light from the source from reaching optical surfaces in the instrument during times when measurements are not actively underway in order to prevent changes in those surfaces which may result from prolonged exposure to the light from the source.

It is important to note that using the designs presented herein, signals from both the sample and reference channels are dispersed using the same region of the diffraction grating within the spectrometer and are recorded using a common detector. This helps to avoid inaccuracies resulting from differences in the local performance of a grating and differences in responses between multiple detectors.

Additionally, it is desirable that a means exist for adjusting or tuning the angles upon which the sample and reference beams enter the spectrometer, such that the two beams are coincident. Differences between the entrance angles of the two beams may result in complications including, but not limited to, artifacts and unwanted features in the ratio of the two signals owing to different effective spectral resolutions (since the two beams "see" different effective slit widths). An effective means of adjusting the entrance angles can be provided through use of a standard kinematic mounting apparatus with which to hold Beam Splitter 2. One skilled in the art will recognize that many other means of adjusting the entrance angles could also be employed. As mentioned above, it may be desirable to closely match the optical path distance of the sample and reference beams such that near equal optical path lengths are obtained. It may be desirable to also match the number and types of optical elements such as mirrors, beam splitters, etc. so that reference and sample paths having substantially similar characteristics are provided. However because absorption resulting from environmental conditions of the chamber may be a dominating factor, the optical path distance may be the most critical factor in matching the beam paths.

In view of the challenges presented by environmental absorption, it is desirable to reduce the overall path length of the device to as short as is practically possible. Limitations on the extent to which this design parameter can be optimized will depend on a number of system characteristics including, but not limited to, the brightness of the source and spectral resolution required. Moreover, it is also beneficial to reduce the volume of the instrument so as to minimize the settling time and quantity of purge gas required to purge the instrument and/or sample chambers. Both of these characteristics can be expected to be influenced to some extent through introduction of forced circulation and intelligent mechanical design to ensure sufficient mixing of gases occurs.

The controlled environment of the instrument brings with it a number of related benefits. Firstly, the use of vacuum or high purity purge conditions necessarily implies an absence of potential contaminates which could lead to oxide growth, hydrocarbon build up, moisture adsorption and the like. This consideration becomes increasingly important as leading edge wafer processing techniques incorporate thinner layers and smaller features, which are now comparable to and/or smaller than the dimensions associated with the thickness of films inadvertently created through contamination processes. In applications where ultra-thin layers are involved it is likely that improvements in measurement accuracy may be realized through pre-measurement treatment of samples in an optional desorber unit (see FIG. 2) in order to remove contamination layers which may be present. As known in the art, such a desorber may remove moisture and other contaminates such as hydrocarbons by using thermal heating. This capability would also play a key role in ensuring the accuracy of calibration and test materials. A further benefit of the controlled environment is that it would provide excellent measurement stability, as the temperature and particulate levels within the instrument could be well controlled.

It may be noted that the referencing techniques described herein provide advantages beyond traditional calibration techniques and that the referencing techniques may be used in combination with calibration techniques and/or in place of calibration techniques. In traditional calibration techniques a reference having a known characteristic (such as a known reflectance) is provided for measurement. The measurement from the known sample is then utilized to assist in analyzing the data that is obtained from a measurement taken from the unknown sample. Such calibration techniques, however, are time consuming if a calibration is performed before every measurement is made on an unknown sample (particularly if multiple measurements are performed upon each sample). In addition, calibration itself introduces errors in that the quality of the calibration sample may degrade overtime (for example as the calibration sample becomes contaminated over time). In addition, the movement of a calibration sample into and out of a sample chamber may introduce further environmental changes that affect the accuracy of the data analysis. The reference techniques described herein may be accomplished without the mechanical introduction of error.

The referencing technique provided herein may be performed, however, quickly and with minimal system impact. Thus for example, a reference measurement may be easily obtained prior to every measurement collected from a sample. Thus real time data referencing closely in time to the sample data collection may be obtained to indicate the conditions of the metrology system. Further, this referencing data may used to adjust the sample data because system absorption effects have been detected. In addition this reference data may truly characterize the system without being dependant upon a standard sample. This referencing data may also be used to adjust the sample data because other system changes have occurred (i.e. like changes in source output). The referencing techniques also may be combined with traditional calibration techniques to more fully characterize collected data. Thus, a system calibration may be performed upon some periodic basis (once a day, once a week, etc.) and the reference techniques may be performed significantly more frequently, for example once per sample or prior to every measurement taken from a sample.

Figure 12:
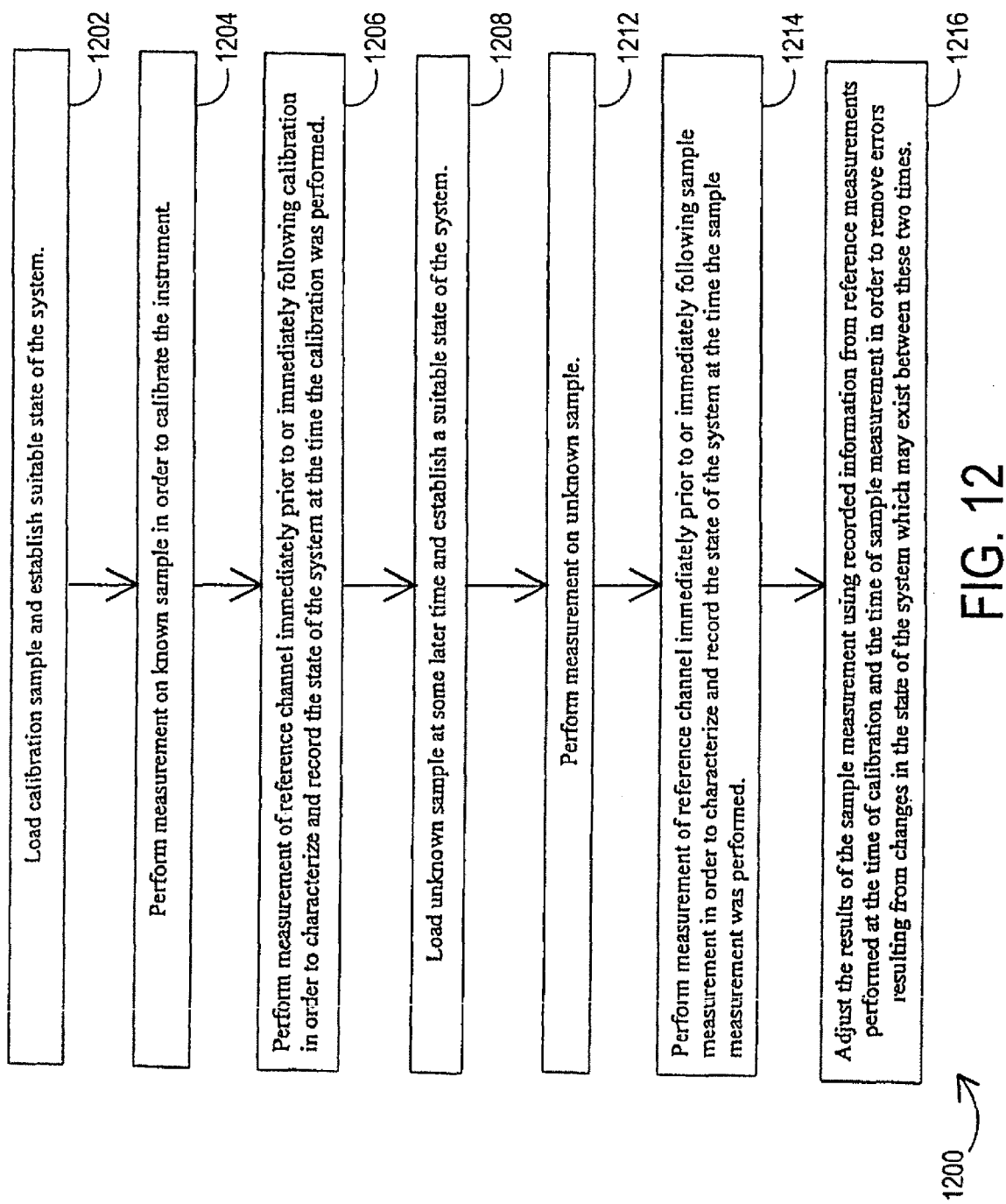
FIG. 12—Typical measurement flow chart.

An example of the typical steps involved in a calibration, referencing and measurement sequence 1200 are provided in a high level in FIG. 12. As shown by step 1202 a calibration sample may be loaded into a sample chamber and a suitable system state (such as absorbing species) may be established. Then, measurements may be performed on the known calibration sample in order to calibrate the optical reflectometer system as shown by step 1204. It will be noted that the system may be actually calibrated at this time or the calibration data may be merely collected to be utilized to adjust any final data results presented from measurements made on an unknown sample (such as adjustments implemented through subsequent software algorithms). Measurements of the reference channel may then be obtained as shown by step 1206 in order to characterize and record the state of the reflectometer system at the time that the calibration measurement was performed. It will be noted that as shown, the measurements of the referencing channel are shown to be performed after the measurement on the calibration sample, however, the referencing measurements may be performed prior to the calibration measurement. It is desirable, however, for such measurements to be made relatively close in time so that the system characteristics at the time of calibration may be determined.

Next an unknown sample that is desired to be analyzed may be loaded into a sample chamber and a suitable system state (such as absorbing species) may be established as shown by step 1208. An optical reflectometer measurement may then be obtained from the unknown sample as shown in step 1212. Measurements of the reference channel may then be obtained as shown by step 1214 in order to characterize and record the state of the reflectometer system at the time that the measurement on the unknown sample was performed. Once again it will be noted that as shown, the measurements of the referencing channel are shown to be performed after the measurement on the unknown sample, however, the referencing measurements may be performed prior to the unknown sample measurement. Finally, as shown in step 1216, the results of the sample measurement may be adjusted using recorded information from the reference measurements performed at the time of the system calibration measurements and at the time of the sample measurement. These adjustments are made in order to remove errors resulting from changes in the state of the system. Thus in this manner changes in the concentration of absorbing species at the time of calibration and the time of measurement of the unknown sample may be accounted for. Thus, the reference beam may be utilized to assist in characterizing the ambient environment concentrations or differences in the concentrations, particularly where other variables such as path length differences are known or may be accurately estimated. As will be described in more detail with reference below to FIG. 14, the presence of non-zero path length differences between the reference beam path and the sample beam path will limit the accuracy of corrections that may be made due to absorbing species concentration variations. Additionally, changes that may be accounted further include changes in elements of the system that are common between the reference beam path and the sample beam path which may exist between the time of calibration measurements and the time of the unknown sample measurements. For example changes of characteristic of the source, shared optics, the spectrometer, the detector, etc. may be addressed. Such changes may be the result of age/lifetime variations, temperature variations, mechanical variations, etc.

Figure 12A:
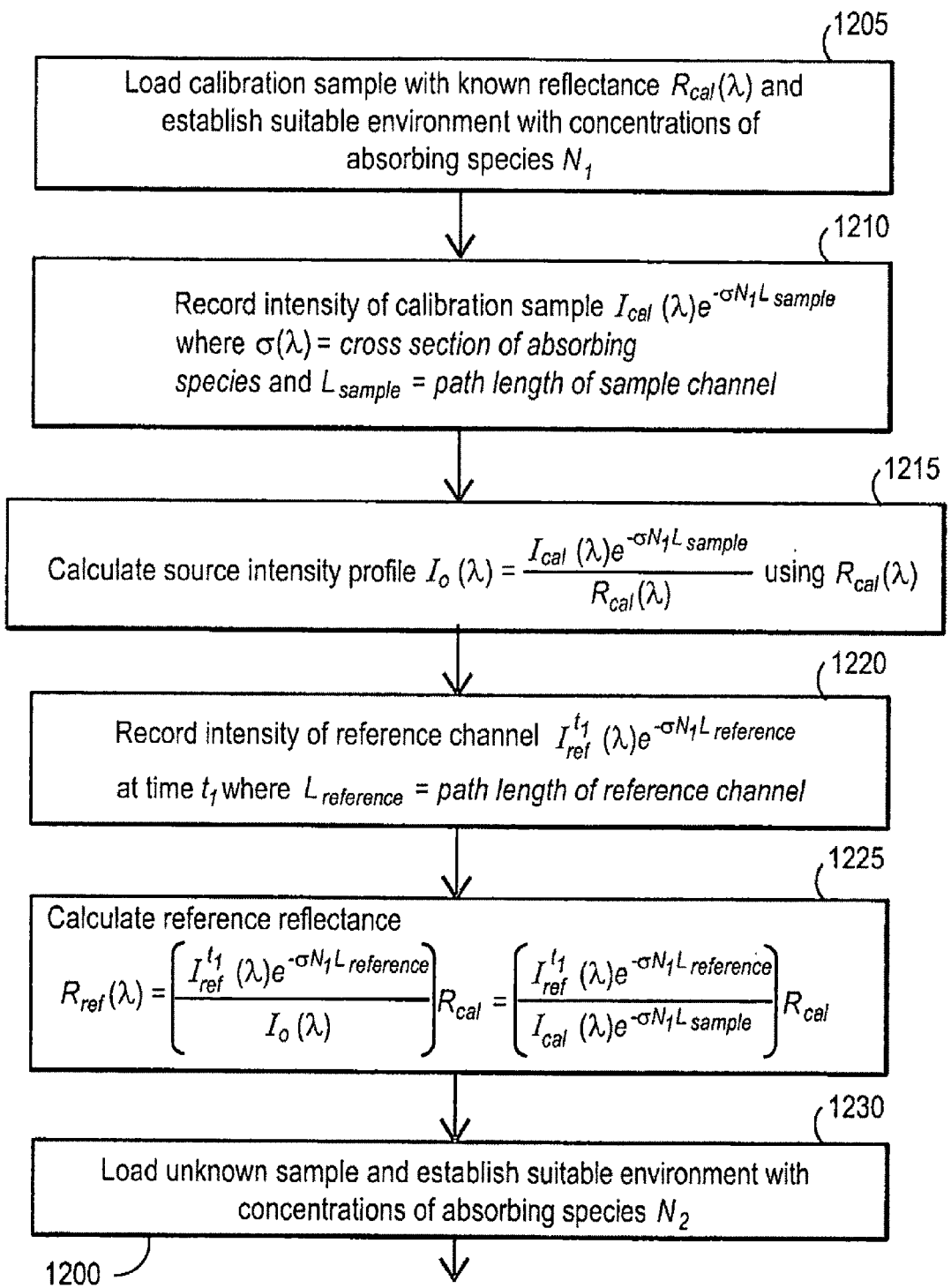
FIG. 12a—(split as FIGS. 12A-A and 12A-B)—Exemplary detailed measurement flow chart.

A more detailed example of the typical steps involved in a calibration, referencing and measurement sequence 1200 are provided in the flowchart of FIG. 12a (split as FIGS. 12A-A and 12A-B). As indicated by step 1205, a calibration sample with a known reflectance may be loaded into a location for measurement (such as within a sample chamber) and then purging and/or vacuum pumping may occur to establish suitably low environmental concentrations of absorbing species. An optical reflectometer measurement may then be obtained from the calibration sample to record an intensity of the calibration sample as indicated by step 1210. Such data may be saved by the processor or other computing system. Next a source intensity profile may be calculated as indicated by step 1215. Step 1220 includes recording the intensity of the reference channel at a time $t_1$. Utilizing the prior recorded and calculated data, a reference reflectance may then be calculated as shown in step 1225.

Next the unknown sample may be loaded into the system and the suitable concentrations of absorbing species may be again obtained as indicated by steps 1230. Another reference measurement may then be recorded and saved as indicated by step 1235 where the intensity of the reference channel is recorded for time $t_2$. The source intensity profile is then calculated again in step 1240 using the data from step 1235. The source intensity profile may be rewritten as shown in step 1245. The intensity of the unknown sample may then be recorded as shown in step 1250 and the sample reflectance can be calculated as shown in step 1255. The sample reflectance may be calculated utilizing the rewritten equations of steps 1260 and 1265. It will be noted that the exponential term the equation of step 1265 is written for the case of two beams (sample and reference) in a single chamber. In the more complicated case of two chambers it would expanded to include two exponential components, one to characterize the differences in the first chamber and the second to characterize the differences in the second chamber.

Additional measurements may then be performed on the same unknown sample or another unknown sample. It will be recognized that for such additional references another loading and measurement of a calibration sample may not occur for each of such measurements, but rather, the calibration data may be stored for re-use and only the referencing and unknown sample steps need be performed again. In yet another embodiment, the data of the referencing steps may also be reused such that additional referencing is not performed for every additional unknown sample measurement. Thus, it will be recognized that the referencing techniques described herein may be utilized in a wide variety of manners while still obtaining at least some of the benefits of the referencing techniques.

As indicated in steps 1255-1265 of FIG. 12a-b, the dependence of the path length and concentration differences are clearly shown. As also indicated in step 1265, when the path length difference (Lsample−Lreference) decreases toward zero, any error caused by the exponential dependence term is reduced since when the difference approaches zero the exponential term approaches unity. It is noted that this will occur independent of the differences in the concentrations (N2−N1). In addition to the typical steps illustrated in the figure, it is recognized that a background measurement performed in the absence of light (i.e. a measurement with both sample and reference shutters closed) would be recorded and subtracted from all subsequent measurements. By nature of the fact that the detector used in the instrument is both cooled and temperature controlled it is unlikely that such background measurements need be performed regularly as the background levels associated with such a detector configuration would be expected to be low and highly stable.

It will be recognized that advantages of the optical metrology systems disclosed herein may be obtained without requiring the use of the referencing techniques described above. Thus, the systems and techniques disclosed herein may be implemented independent of the referencing techniques or in combination with the referencing techniques. Further, the referencing techniques provided herein may be utilized with optical metrology systems different from those disclosed herein or with systems that operate at different wavelengths. The referencing techniques and the optical metrology systems disclosed herein, may however, be particularly advantageous when used in combination.

While not shown in FIGS. 12 and 12a (split as FIGS. 12A-A and 12A-B), it may also be useful in situations, where significant levels of stray-light are present, to perform an additional corrective step during the data acquisition process. Stray light refers to light generated through scattering processes at optical surfaces in the beam path of the system. The presence of such light can ultimately result in spurious counts recorded by the detector (i.e. light of wavelength other than $\lambda_o$ that is incident upon the pixel corresponding to $\lambda_o$). While the VUV apparatus described herein has been designed such to considerably reduce the generation of stray light within the device, it may still be advantageous to correct for this phenomena in some circumstances.

One approach to correct for stray light within the system involves attempting to record light below the spectral range of the instrument (i.e. below the lower wavelength cutoff of the device). Any signal recorded below this region should not, by definition exist, and is instead assumed to have been created through scattering processes. Equipped with an understanding of the intensity of such signal, as a function of wavelength, it is possible to subtract the appropriate "stray light" contribution from longer wavelength regions within the spectral range of the instrument where "real" signals are simultaneously being recorded.

The concepts disclosed herein provide a VUV optical reflectometer metrology tool. The design of the tool is simple and robust rendering it easy to operate at VUV wavelengths. Further, the tool avoids many of the problems associated with ellipsometry techniques. For example, the tool and techniques disclosed herein may be utilized without polarization elements. In ellipsometry, the change in the polarization state of light reflected from the surface of a sample is measured. Typical ellipsometry techniques use at least two polarizing elements (one in the optical path prior to the sample and one in the optical path after the sample). Such techniques are time consuming because of the nature of collecting data for multiple polarization angles. In addition, polarization elements are generally absorbing thus making them unsuitable for low wavelength measurements, particularly in the VUV regions of about 140 nm or less. Thus, the systems and techniques described herein (which may be utilized without polarizing elements) are particularly advantageous for use with wavelengths that are low end VUV regions (or lower). The absorbing nature of polarizing elements also increases the time necessary to collect sufficient light to obtain a measurement.

Thus, it may be desirable to provide a reflectometer tool utilizing the techniques disclosed herein with a non-polarizing optical path such that a polarization independent measurement may be obtained. The polarization independent techniques shown herein provide a phase independent reflectivity amplitude measurement. The reflectometer tools described herein typically include multiple wavelengths within the optical path until the optical path hits the diffraction grating, at which point the wavelengths are spatially separated. Ellipsometry techniques traditionally involve filtering the light source to a single wavelength at some point in the optical path. It should be noted that at least some of the techniques and tools described herein may be useful for applications known as polarized reflectometry. Such applications may typically use a single polarizing element located either before or after the sample to enable collection of reflectivity amplitude data in one of two possible polarization states.

The tools and techniques disclosed herein also are advantageous compared to ellipsometer techniques because of the smaller angle of incidence that is required of the optical beam with reference to the sample. Thus for example as shown with reference to FIG. 11a, an angle of incidence φ of 10° or less and even 4° or less is possible utilizing the techniques disclosed herein as opposed to ellipsometer techniques which often utilize angles of incident on the order of 70°. This is advantageous as the footprint of the metrology tool is smaller and the integration of the metrology tool with process tools is simpler. For example, it is possible to integrate the metrology tools disclosed herein with a process tool through the use of one coupling mechanism as opposed to requiring multiple coupling mechanisms.

Figure 15:
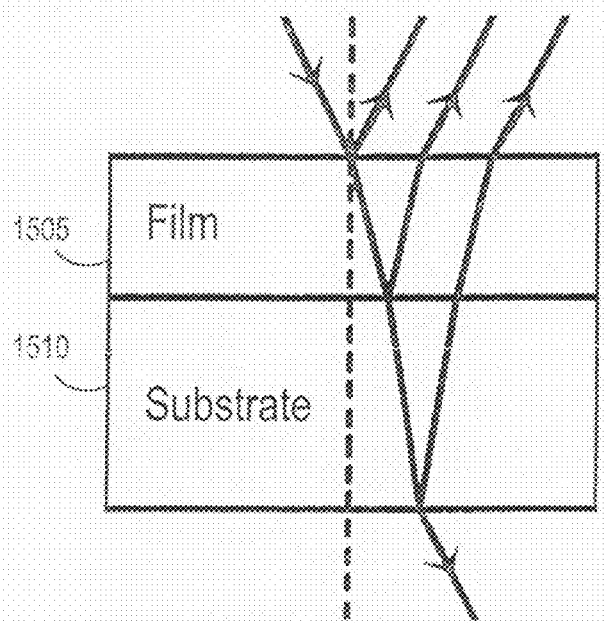
FIG. 15—Schematic representation of typical reflectance measurement.

Once spectral reflectance data is recorded by the detector it is sent to the processor unit depicted in FIG. 2, where it is subsequently reduced via analytical algorithms. These algorithms may generally relate optical data, such as for example reflectance, to other properties of the sample which can then be measured and/or monitored. If the sample is comprised of a thin film 1505 (or stack of thin films) on a substrate 1510, then the situation can be depicted as in FIG. 15 and the associated sample properties may include quantities such as for example, but not limited to, film thickness, complex refractive index, composition, porosity and surface or interface roughness.

Data reduction is generally accomplished using some form of the Fresnel equations in combination with one or more models to describe the optical properties of the material or materials comprising the sample. There are a large number of such models in existence with differing degrees of applicability, depending on the nature of the materials involved. Frequently used models include, but are not limited to, the effective median approximation (EMA) and variations on what is commonly referred to as the "harmonic oscillator". Regardless of the specific models used in the reduction of the data set, the greater goal is generally to use a valid mathematical expression to describe the measured data such that certain parameters relating to properties of the samples (as discussed above) can be obtained through an iterative optimization process. That is, the measured data set is compared to one calculated using an expression that depends on a set of parameters relating to the nature of the sample. The discrepancy between the measured and calculated data sets is minimized by iteratively adjusting the values of the parameters until such time as adequate agreement between the two data sets is achieved. This discrepancy is usually quantified in terms of a "goodness of fit" parameter.

Figure 16:
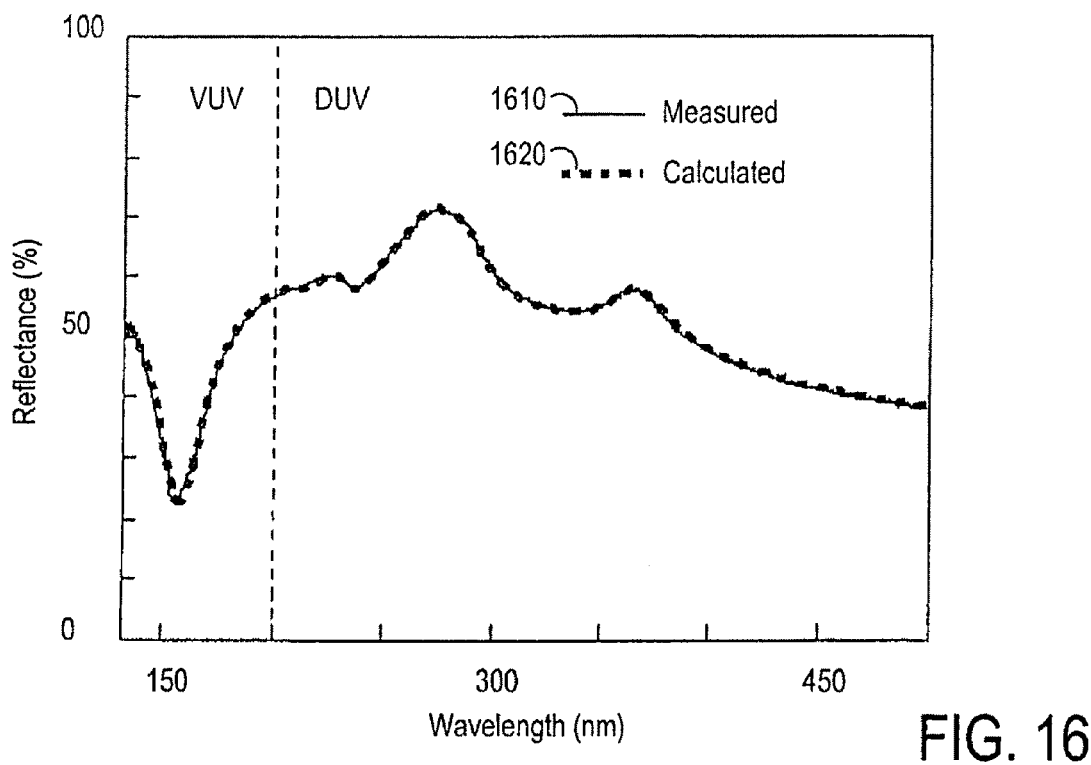
FIG. 16—Measured and calculated reflectance spectra from thin Al2O3 layer deposited on silicon substrate.

As many materials exhibit significantly more structure in the VUV region of their optical properties, than at longer wavelengths in the deep-ultra-violet (DUV) and visible regions, there is a considerable advantage associated with the extended data range afforded by the VUV apparatus described herein, particularly as is relates to the data reduction process. This point is illustrated through the examples provided in FIG. 16 and FIG. 17. The two curves in FIG. 16 represent the measured reflectance spectra 1610 (solid line) and calculated reflectance spectra 1620 (dotted line) of a thin (~50 Å) aluminum oxide ($Al_2O_3$) layer deposited on a silicon substrate. The calculated result was obtained using the data reduction methods outlined above. As is evident, excellent agreement is obtained between the measured and calculated spectra, providing a high degree of confidence in the accuracy of the acquired results.

Figure 17:
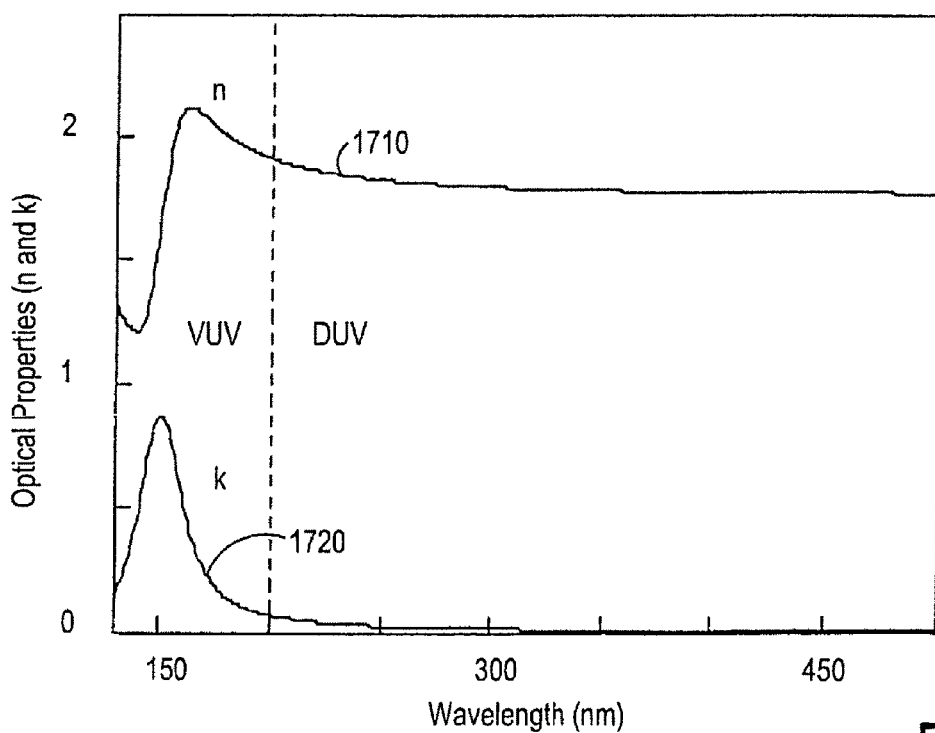
FIG. 17—Optical properties (n and k values) obtained for Al2O3 layer through iterative fitting process.
Figure 18:
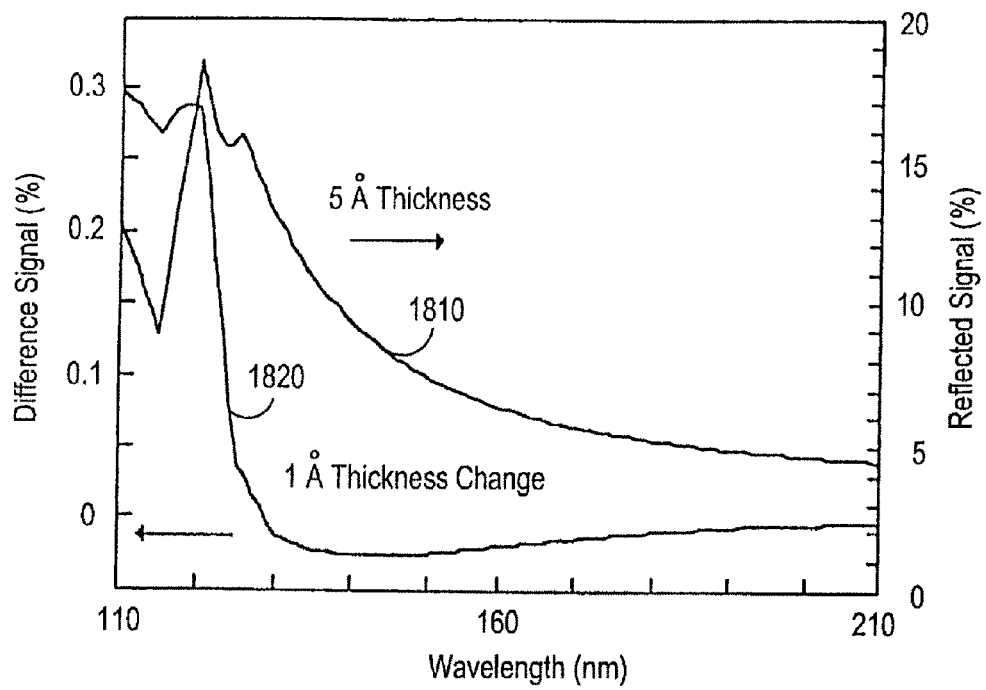
FIG. 18—Reflected signal associated with ultra-thin (5 Å) layer of residual photo resist deposited on mask blank. Difference signal corresponding to a 1 nm increase in layer thickness.
Figure 19:
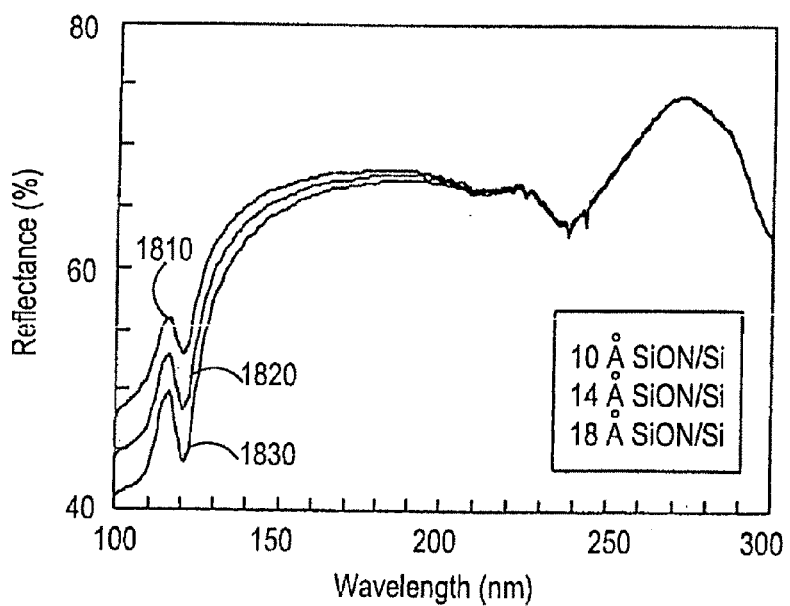
FIG. 19—Reflectance signal from 10 Å, 14 Å, and 18 Å SiON layers on silicon substrates.

The n and k values (the values of the real and imaginary parts respectively of the complex index of refraction) obtained for the $Al_2O_3$ layer are presented in FIG. 17. As is evident from the plot 1710 of n values and the plot 1720 of k values, the optical properties in the DUV and visible region show little in the way of defining structure, as the main peaks associated with the n and k spectra reside exclusively at shorter wavelengths in the VUV. As the parameters in the fitting algorithm are inherently related (among other things) to the position, amplitude and breadth of these peaks it follows that an accurate determination of such parameters is greatly aided by providing the fitting routine with actual measured data spanning the wavelength range of interest. In other words, as the optical properties of many materials tend to exhibit the majority of their defining structure in the VUV (and not in the DUV or visible regions) it is highly desirable to make use of measured data in this spectral region when attempting to accurately determine such properties. FIG. 18 illustrates how the VUV techniques disclosed herein may be utilized to identify and measure very thin layers in a semiconductor process environment. The first curve 1810 in the figure, corresponding to the y-axis on the right hand side, presents the reflectance signal associated with an ultra-thin (5 Å) layer of residual photo resist on a blank mask substrate. The second curve 1820, corresponding to the y-axis on the left hand side, presents the difference signal associated with a 1 Å increase in the film thickness of the said layer of residual photo resist. It is clear that the largest changes in the difference signal appear at shorter VUV wavelengths, and that the difference signal tends to zero as the wavelength approaches the longer wavelengths in the DUV. FIG. 19 provides a further example of how the disclosed methods may be used to measure or monitor the thickness of ultra-thin layers. Three curves are present in the figure and correspond to reflectance spectra recorded from samples consisting of a thin 10 Å layer (curve 1810), a thin 14 Å layer (curve 1820) and a thin 18 Å layer (curve 1830) of silicon oxy-nitride (SiON) deposited on silicon substrates. As is evident, the differences between the spectra are again greatest at the shorter VUV wavelengths and, in this case, essentially non-existent at longer DUV wavelengths. This is an increasingly important aspect as it relates to semiconductor process control since the semiconductor industry is constantly working to incorporate thinner and thinner layers into semiconductor devices.

Figure 20:
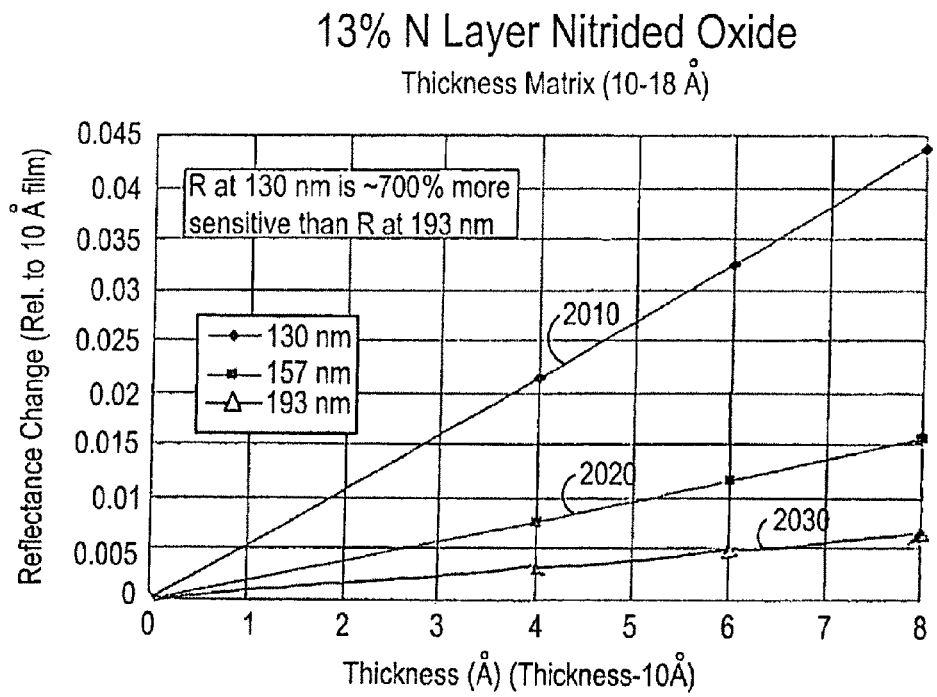
FIG. 20—Reflectance difference signal at 130 nm, 157 nm and 193 nm associated with increase in film thickness for a 10 Å SiON layer.
Figure 21:
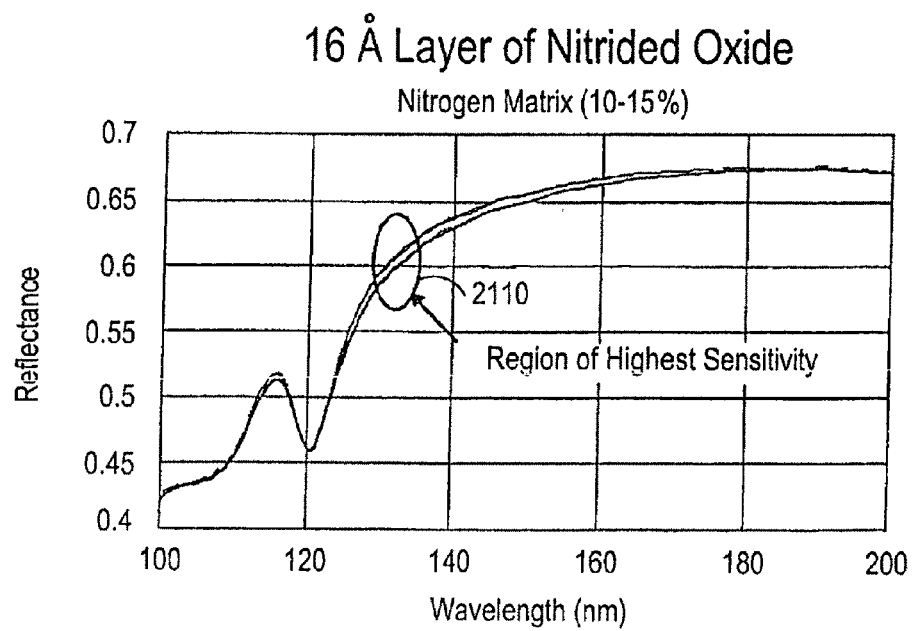
FIG. 21—Reflectance signal associated with matrix of 16 Å SiON layers possessing nitrogen concentrations in the range of 10-15%.
Figure 22:
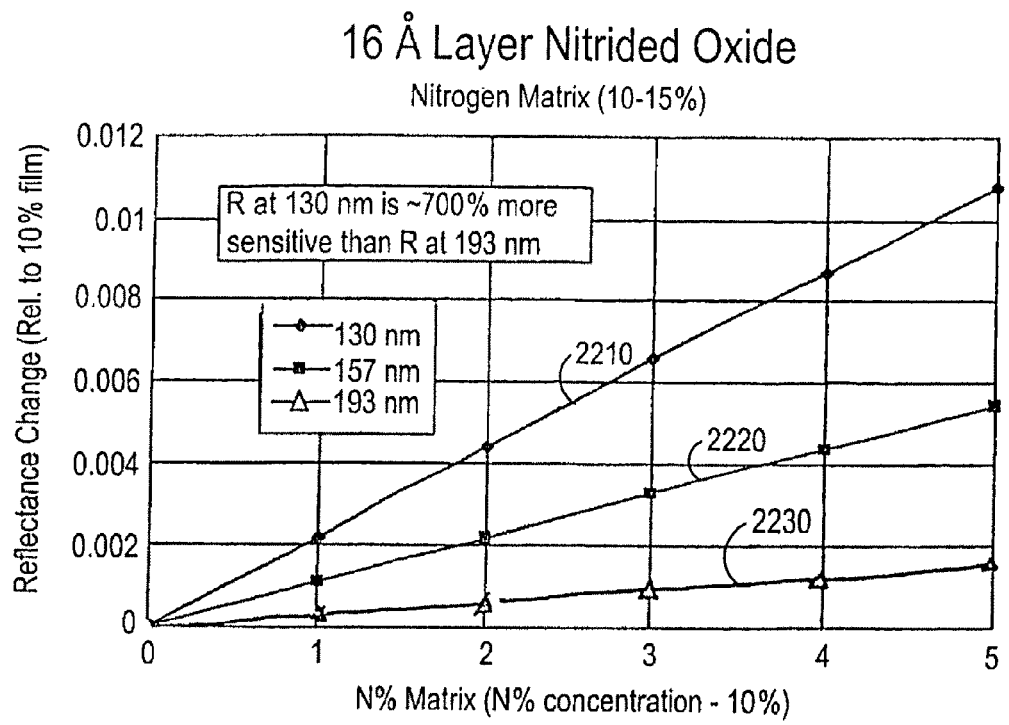
FIG. 22—Reflectance difference signal at 130 nm, 157 nm and 193 nm associated with increase in nitrogen concentration for a 16 Å SiON layer with 10% nitrogen.

This point is further emphasized upon examination of FIG. 20, which presents the reflectance change (relative to a nominal 10 Å layer) for a $SiO_{0.87}N_{0.13}$ layer as a function of film thickness (relative to a nominal 10 Å layer with 13% nitrogen). As is evident from the graph the reflectance changes at 130 nm (plot 2010) for a given change in film thickness are larger in turn than those expected at either 157 nm (plot 2020) or at 193 nm (plot 2030). In fact, the changes in the VUV at 130 nm are approximately seven times greater than those exhibited at in the DUV at 193 nm. FIG. 21 and FIG. 22 illustrate generally how the VUV techniques described herein may be utilized to monitor the composition of a material or film. FIG. 21 presents reflectance spectra for a series of six 16 Å thick SiON layers deposited on Si with concentrations ranging from 10% to 15%. As is evident, region 2110 is the region of highest sensitivity to changes in the composition of the SiON films and is centered at approximately 130 nm. This point is further emphasized following examination of FIG. 22 which presents the reflectance change (relative to a nominal 16 Å SiON layer with 10% nitrogen) for a SiON layer as a function of film thickness (relative to a nominal 10 Å layer). As is evident from the graph the reflectance changes at 130 nm (plot 2210) for a given change in film thickness are larger in turn than those expected at either 157 nm (plot 2220) or at 193 nm (plot 2230).

Figure 22A:
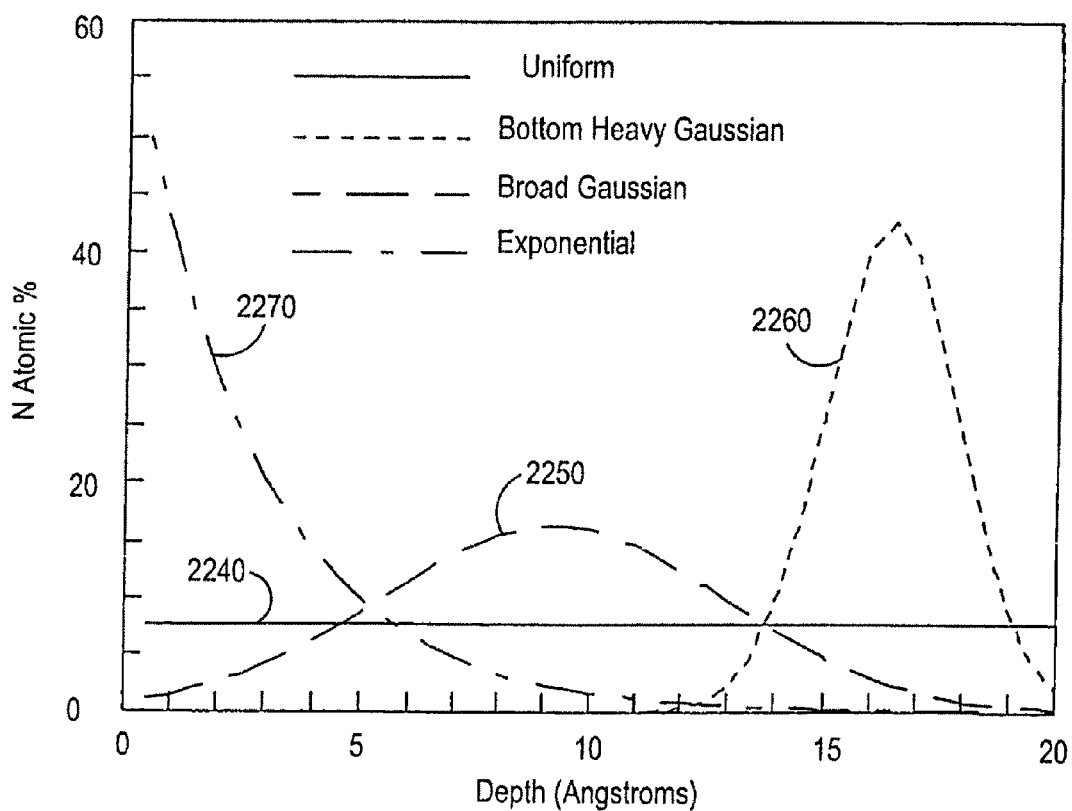
FIG. 22a—Different nitrogen doping profiles for a 20 Å SiON film. In all cases the samples were exposed to the same dose of $1e^{15}$ atoms/cm$^2$.

As a further example of the benefits afforded by the use of the VUV methods presented herein, the determination of the composition of a SiON film exhibiting a non-uniform distribution of nitrogen (as a function of film thickness) is considered. FIG. 22a presents a series of four nitrogen distributions for 20 Å $SiO_2$ films subjected to a dose of $1e^{15}$ nitrogen atoms/$cm^2$. The nitrogen atomic % is plotted as a function of film depth (as measured from the ambient/film interface). While the same numbers of nitrogen atoms are contained within each of the four samples, the distributions of those atoms are considerably different. In one case the nitrogen is uniformly dispersed throughout the thickness of the layer (plot 2240), in another it is incorporated such that it exhibits a broad Gaussian distribution centered in the middle of the film depth (plot 2250), in yet another it exhibits a bottom heavy Gaussian distribution (centered closer to the film/substrate interface) (plot 2260) and in the final case it exhibits a exponentially decaying distribution (plot 2270).

Figure 22B:
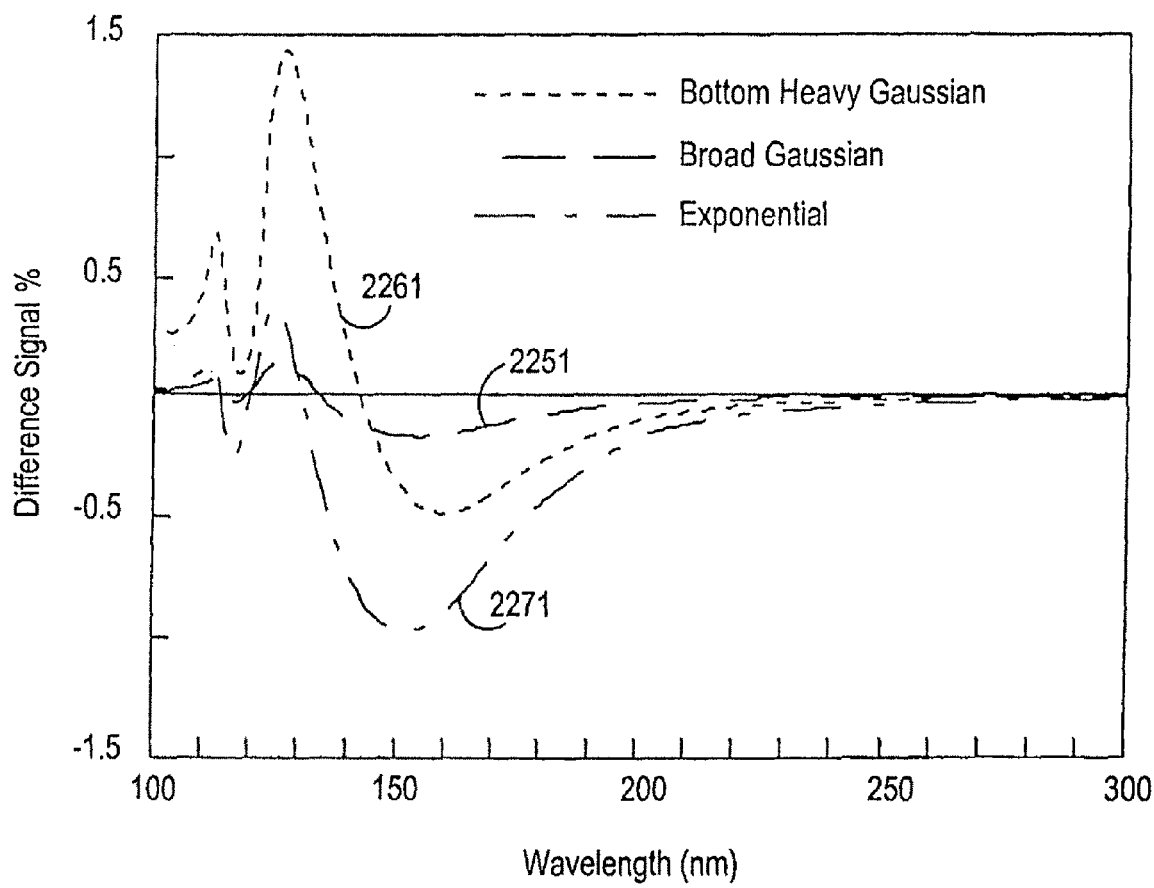
FIG. 22b—Reflectance difference signals (relative to the uniformly doped sample) resulting from a variety of non-uniform nitrogen distributions.

FIG. 22b presents the reflectance difference signals associated with the samples exhibiting the broad centered Gaussian (plot 2251), bottom heavy Gaussian (plot 2261) and exponentially decaying (plot 2271) distributions. The reflectance difference signal is obtained by subtracting the reflectance signal associated with the normally distributed sample from that of the other three. As is evident, the non-uniformly distributed samples all exhibit significant and clearly distinguishable reflectance difference signals in the VUV region of the spectrum, while at the same time exhibiting little or no differences at longer wavelengths. This figure acts to further illustrate how the VUV techniques herein disclosed can be used to measure and/or monitor the compositional profile of very thin layers.

While the exemplary layers of FIG. 17-FIG. 22b are those of Al2O3, photoresist and SiON, it will be recognized that layers and film stacks of other materials, deposited on a variety of substrates including, but not limited to silicon wafers and photo mask blanks, may be measured in a similar fashion.

Another advantage afforded by the VUV wavelengths may be realized when measuring certain film stacks comprised of two or more layers. As the number of films in a stack is increased, so generally is the number of parameters sought in the optimization routine. As the number of parameters increases so does the likelihood that correlations between the parameters may exist. In some circumstances this may contribute to inaccuracy or instability in measured results. In some situations it may be possible to simplify the problem, and hence reduce the number of parameters sought in the optimization routine by exploiting use of the optical data in the VUV through incorporation of an intelligent weighting function.

Figure 23:
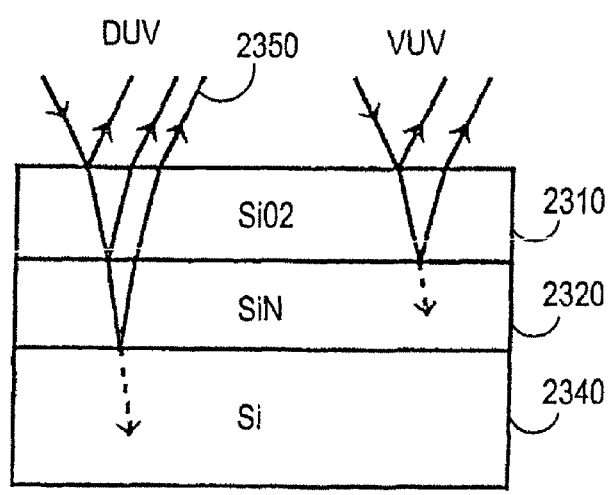
FIG. 23—Interaction of incident DUV and VUV photons with typical semiconductor stack sample during reflectance measurement.
Figure 24:
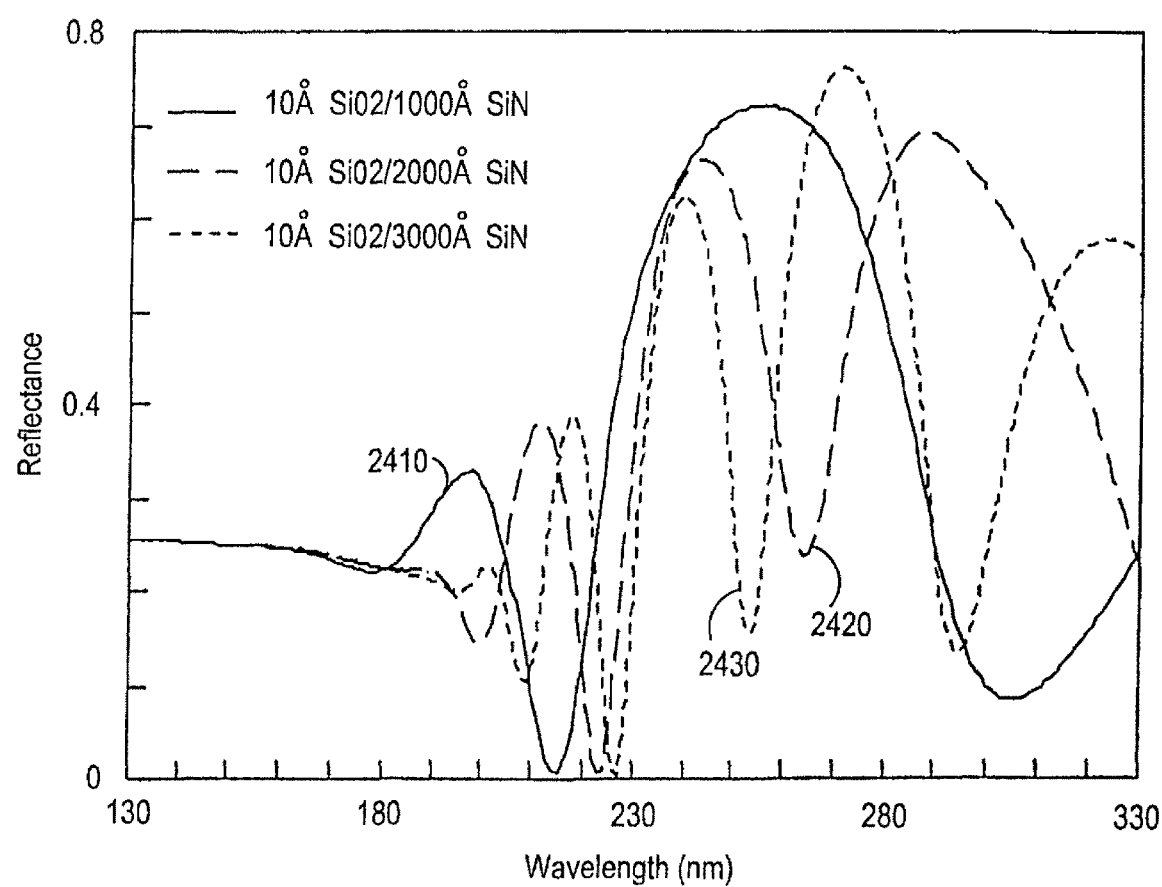
FIG. 24—Reflectance spectra from SiO2/SiN/Si samples exhibiting different SiN thicknesses.

This function, herein referred to as the "dynamic weighting function" involves dynamically ascribing greater or lesser emphasis on specific datum during the optimization process depending on their expected contribution to the determination of the set of parameters being sought. In such an approach the expected contribution is dynamically estimated based on the expected configuration of the sample (i.e. thickness and composition of layers comprising the sample) and is updated on an iteration by iteration basis. For example, as shown in FIG. 23 when measuring a two layer film stack comprised of silicon dioxide ($SiO_2$) layer 2310 and silicon nitride (SiN) layer 2320 deposited on a silicon substrate 2340, it may prove beneficial to place greater emphasis on data points in the VUV during the search for thickness of the top $SiO_2$ film. This follows from the fact that the SiN is, for all intents and purposes, opaque to VUV photons at thicknesses greater than about 1000 Å. Thus as shown in FIG. 23, reflectance 2350 from the SiN-Substrate interface may be present in measurements made with DUV wavelengths but may be absent in measurements made with VUV wavelengths. Hence, the thickness of the underlying SiN layer can essentially be disregarded during the optimization process if DUV and longer wavelength data is neglected. This point is further illustrated upon examination of FIG. 24 and FIG. 25. FIG. 24 presents reflectance data from three $SiO_2$/SiN/Si samples. The SiN layer thickness varies from 1000 Å (plot 2410), to 2000 Å (plot 2420) to 3000 Å (plot 2430) amongst the samples, while the $SiO_2$ layer thickness remains fixed at 10 Å. As is evident, the reflectance spectra from the three samples appear markedly different in the DUV region, and yet virtually identical at VUV wavelengths. This follows from the fact that VUV photons do not penetrate the SiN layer and instead "see" a sample comprised of 10 Å of $SiO_2$ deposited on a SiN substrate. Applying a weighting function which strongly emphasizes the VUV and strongly de-emphasizes the DUV and longer wavelength data thereby reduces the parameter set sought by the optimization routine since the result is then insensitive to the SiN layer thickness. This approach reduces or altogether removes any correlation between the thickness parameters for the $SiO_2$ and SiN layers that may exist, thereby acting to increase the accuracy and repeatability of the measurement results. Additionally, this approach will generally result in convergence of a solution in a significantly shorter period of time than possible using conventional methods.

Figure 25:
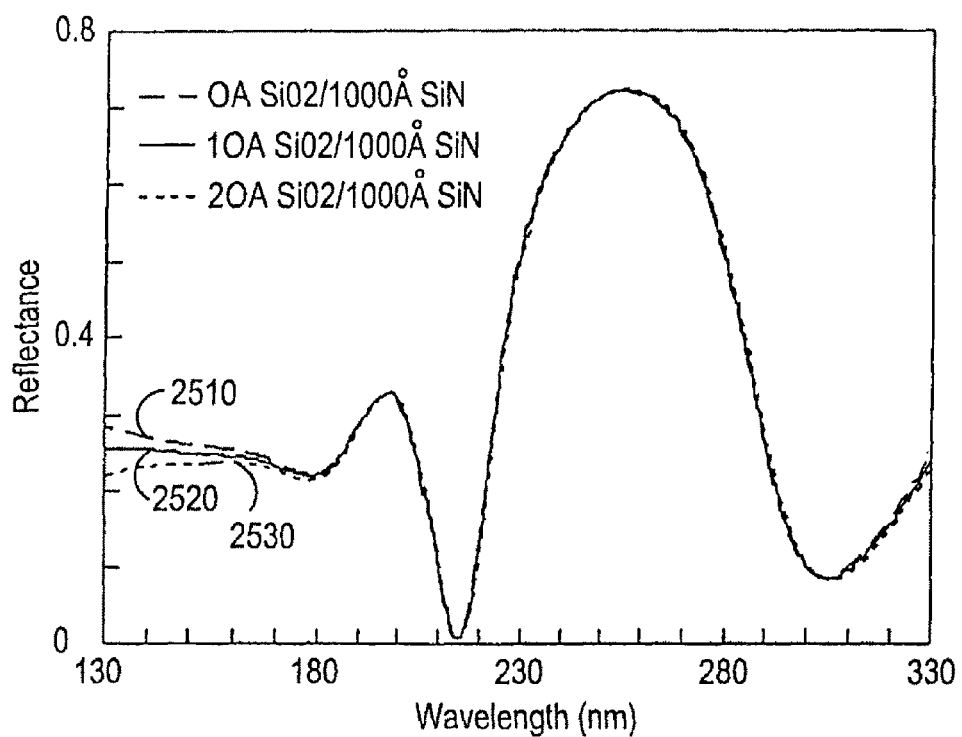
FIG. 25—Reflectance spectra from SiO2/SiN/Si samples exhibiting different SiO2 layer thicknesses.

Further evidence of the benefit of such a dynamic weighting function is provided in FIG. 25, which also presents reflectance spectra from three $SiO_2$/SiN/Si samples. In this case the SiN layer thickness is fixed at 1000 Å amongst the samples, while the $SiO_2$ layer thickness varies from 0 Å (plot 2510), to 10 Å (plot 2520) to 20 Å (plot 2530). As is seen, the spectra exhibit clear differences in the VUV region, while appearing virtually identical in the DUV. Thus, because of the sensitivity of the tools and techniques described herein to absorption effects, the absorption of shorter wavelengths in the thin films being measured may be advantageously utilized. Moreover, in situations in which a rough estimate of the anticipated sample characteristics is known (for example a rough estimate of the underlying SiN film thickness), greater importance (or dynamic weighting) may be placed upon the reflectivity data in certain wavelength regions.

While the exemplary samples of FIG. 23, FIG. 24 and FIG. 25 are comprised of $SiO_2$/SiN/Si is it clear that the dynamic weighting function approach can be used to measure and or monitor samples possessing more than two layers and which, are comprised of different materials.

The dynamic weighting function may also be utilized in conjunction with an iterative data fitting process. For example, for data collected from the SiO2/SiN/Si layers described above with reference to FIGS. 23-25, an iterative process can be utilized to attempt to determine the thickness of each of the layers. During each iteration of the fitting routine the differences between the calculated and measured data sets may be mathematically compared at each wavelength and used to determine whether changes made in the values of the parameters of the fitting routine (in this case the film thicknesses) were an improvement over the parameter values obtained in the previous iteration. It is advantageous to include a weighting factor which takes into account the approximate nature of the sample. For example, the data in FIG. 25 clearly reveals that wavelengths above ~180 nm contain no information about the thickness of the top SiO2 layer. Traditional data fitting methods would ignore this fact and attempt to compare the measured and calculated data at all measured wavelengths when seeking this thickness. As a result, most of the wavelengths being compared (those greater than 180 nm) could only increase the uncertainty into the result since they represent a significant portion of the weighted comparison function. Using the dynamic weighting function approach the problem could be broken down such that only measured data that could reasonably be expected to contain useful information would be included into the weighted comparison function. The method is dynamic since the decision making process (which measured data should be considered) could be repeated after each iteration.

Figure 26:
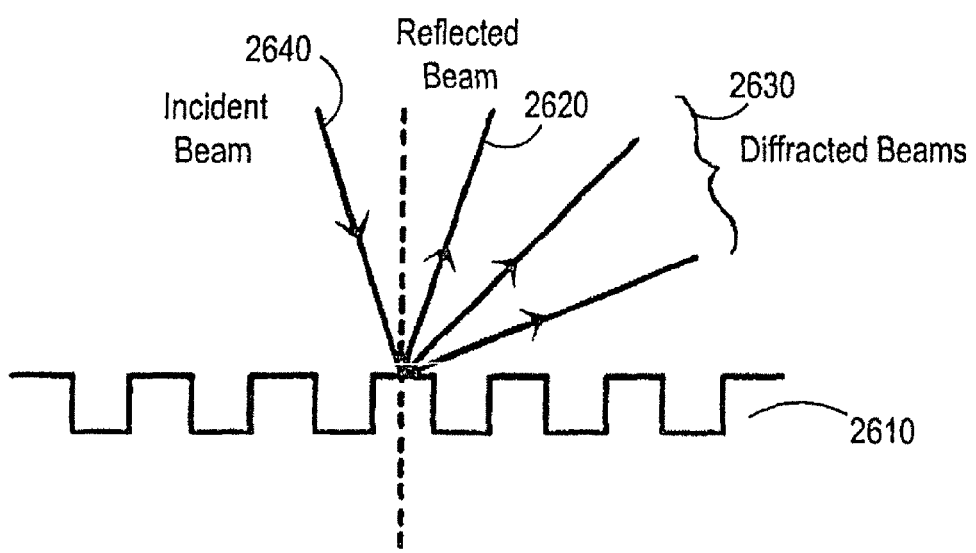
FIG. 26—Schematic representation of typical scatterometry measurement illustrating both reflected and diffracted beams.

When patterned samples are involved additional theoretical constructs are typically invoked to properly describe the light scattering, which occurs as a result of the interaction between the measurement photons and periodic patterned features. Such light scattering is shown with reference to FIG. 26. FIG. 26 illustrates a patterned substrate 2610 and the reflected beam 2620 and diffracted beams 2630 that result from the incident beam 2640. This form of non-imaging optical dimensional metrology is known as scatterometry and commonly involves employment of some form of "rigorous coupled wave analysis" (RCWA) during the data reduction process. This technique exploits the sensitivity of light scattering from a patterned sample and relates the dimensions of the features comprising the sample to the optical signal recorded from such through use of an appropriate mathematical expression. In other words, scatterometry enables the dimensions of patterned features to be determined by accounting for light scattered or diffracted from a sample containing patterned features.

Figure 27:
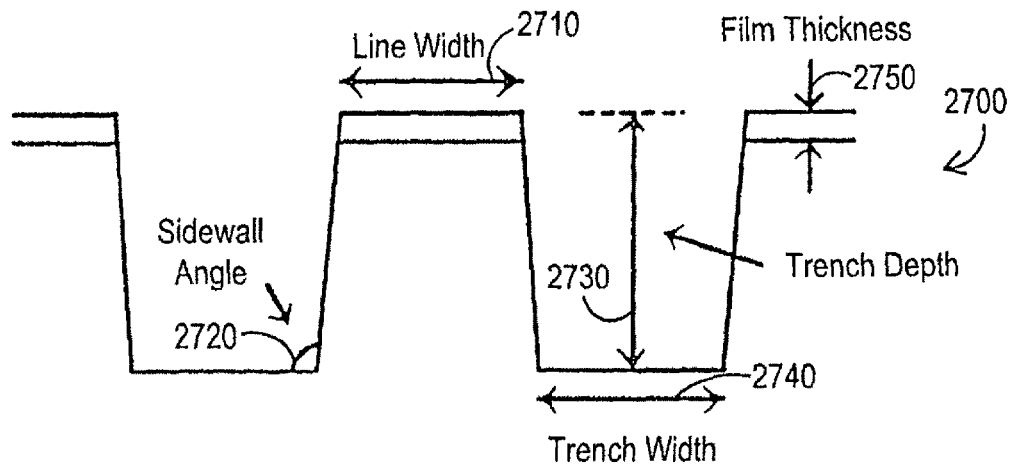
FIG. 27—Schematic representation of typical outputs obtained through scatterometry measurements.

Examples of exemplary quantities that may be measured and/or monitored on a patterned substrate 2700 using this approach are depicted graphically in FIG. 27 and include, but are not limited to, critical dimensions (line widths) 2710, sidewall angles 2720, trench depths (or line height) 2730, trench widths 2740 and film thickness 2750. It is understood that these quantities represent a select number of the many such quantities that may be measured and/or monitored in thin film stacks and/or structures. Patterned thin film samples of this nature are found in many areas including semiconductor devices and storage media.

As a review of light scattering physics reveals, short wavelength photons like those in the VUV are inherently better suited to measuring or monitoring smaller critical dimensions of patterned features than longer wavelength photons, owing to the increased sensitivity afforded by the former. In fact, it can be seen that for many critical dimension metrology applications involving leading edge semiconductor devices, measurement is only possible using short wavelength VUV photons. This point will is further illustrated through the examples provided below.

Figure 28:
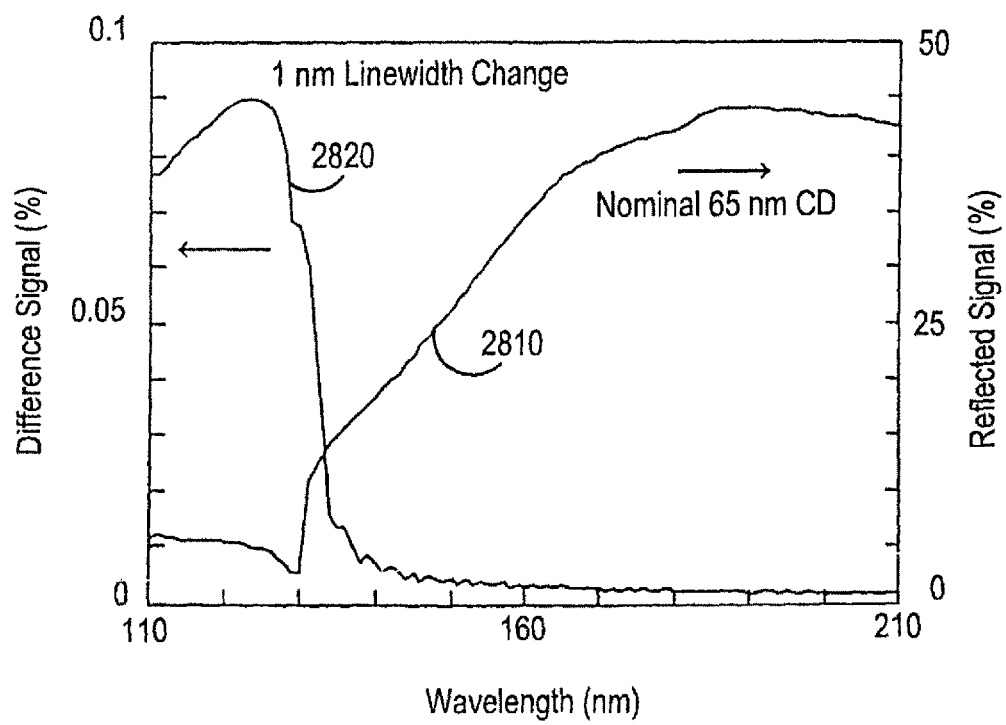
FIG. 28—Reflected signal associated with nominal 65 nm line array and difference signal corresponding to 1 nm increase in nominal 65 nm line width.

FIG. 28 illustrates an exemplary VUV measurement relating to line width determination. The first curve 2810 in the figure, corresponding to the y-axis on the right hand side, presents the reflected signal obtained from a 65 nm line array with a pitch of 130 nm. That is, a line array constructed such as to exhibit 65 nm wide lines separated by 65 nm wide spaces. The second curve 2820 in FIG. 28, corresponding to the y-axis on the left hand side, presents the difference in the reflected signal between 66 nm and 65 nm line arrays. That is, this curve represents the difference signal associated with a 1 nm increase in line width for a line array exhibiting 65 nm wide lines and spaces. As is evident from the figure, distinctive and significant changes in the difference signal are only expected at and below wavelengths corresponding to the pitch of line array (65 nm line width+65 nm space width=130 nm pitch). Hence, in order to measure or monitor the line width in such a structure using the approach described herein, it is necessary that the range of measured wavelengths include those at and below the pitch wavelength.

Figure 29:
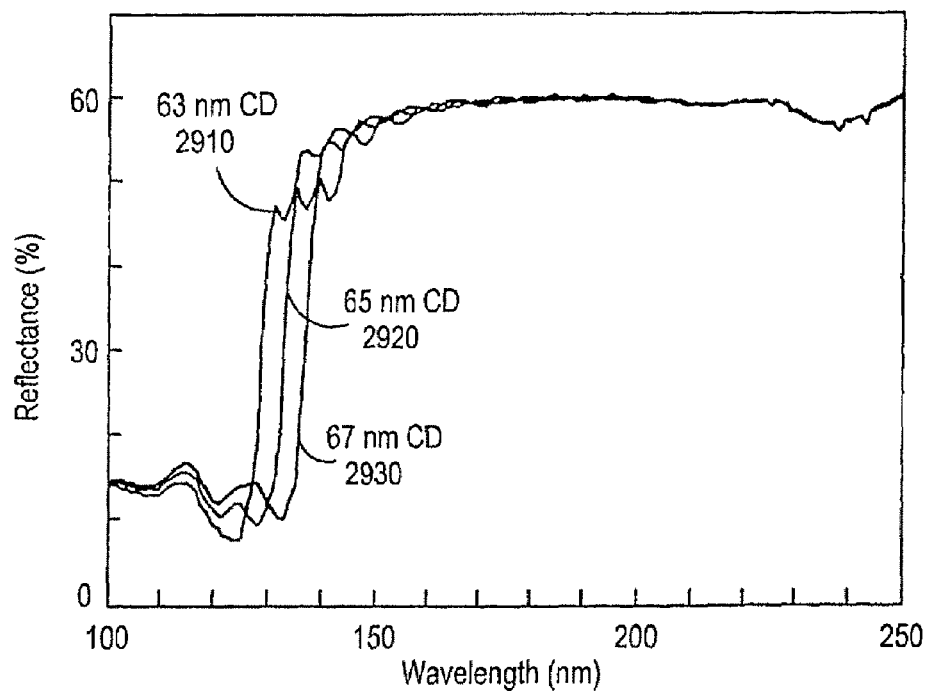
FIG. 29—Reflected signal associated with line arrays comprised of 63 nm, 65 nm and 67 nm lines and spaces.

FIG. 29 illustrates an exemplary VUV measurement relating to pitch determination. The three curves in the figure represent reflectance signal expected from line arrays comprised of 63 nm (curve 2910), 65 nm (curve 2920) and 67 nm (curve 2930) lines and spaces. That is, the data represent signal from line arrays with equal line width and space width, but with pitches of 126 nm, 130 nm and 134 nm. As is evident from the figure, changes in the three spectra are predominantly evident in the spectral region immediately at and below the wavelength corresponding to the line array pitch (again near 130 nm in this example).

Figure 30:
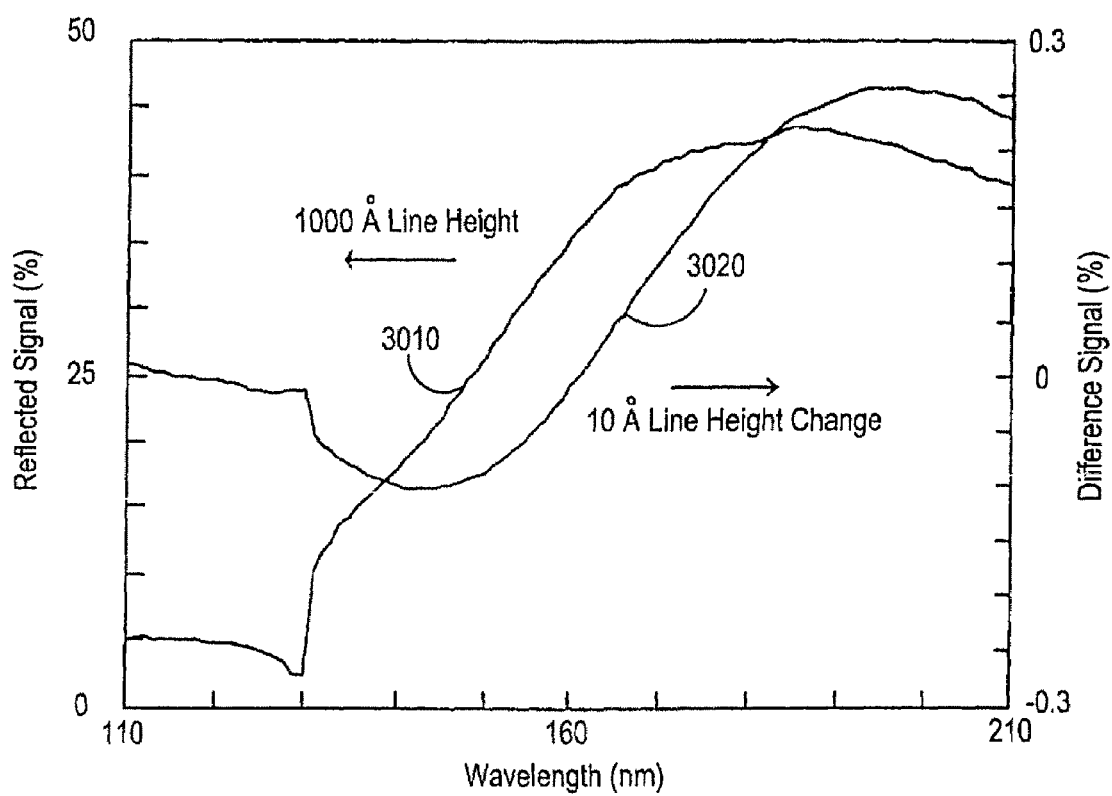
FIG. 30—Reflected signal associated with line array comprised of 65 nm wide lines and spaces (for nominal line height of 1000 Å). Difference signal corresponding to 10 Å increase in line height of said structure.

FIG. 30 illustrates how the VUV techniques and apparatus described herein can be used to measure or monitor changes in the height of lines comprising a line array. Two curves are presented in the figure. The first curve 3010, corresponding to the y-axis on the left hand side, presents the expected reflectance signal from a line array with 65 nm lines and spaces, wherein the line height is 1000 Å. The second curve 3020, corresponding to the y-axis on the right hand side, presents the difference signal associated with a 10 Å increase in line height for the same such line array. As is evident the changes in line height bring about a spectral signature markedly distinct from the changes introduced through in line width and pitch presented earlier (for reference refer to FIG. 29 and FIG. 30). That is, the spectral region exhibiting the smallest difference signal resulting from changes in line height is in fact the same spectral region exhibiting the largest difference signal resulting from changes in line width and pitch.

Application of the VUV techniques and apparatus described herein in the field of semiconductor process control metrology are both numerous and wide-ranging. In general, it has been demonstrated that the VUV reflectometer techniques provided herein may provide data shown reflectance magnitudes at given wavelengths. Further, the sensitivity of these measurements may be meaningfully related to semiconductor manufacturing process data to provide data indicative of various process variables. In this manner the systems and techniques provided herein may be utilized in process control and process characterization applications. Specific examples of a select number of such cases have been presented, however those skilled in the art will recognize that these methods can be further applied in many other situations.

The techniques described herein may be incorporated into off-line stand alone metrology equipment utilized for metrology applications. However, because they may be implemented in a relatively less complex hardware solution that may yield a measurement result relatively quickly and repeatedly, the techniques described herein may be particularly suited for incorporation into any of a wide variety of semiconductor process tools. Thus, for example, the VUV techniques described herein may be incorporated directly into tools used for deposition, etch, photolithography, etc. so that in-line measurements, monitoring and control may be advantageously obtained.

The equipment, components, materials, and techniques described above may be utilized in a system that utilizes a broad band range of wavelengths. For example, a reflectometer that includes VUV wavelengths may be configured to operate in at least one other spectral region. Thus, all or parts of the systems and techniques described above with reference to FIGS. 1-30 may be utilized in conjunction with broad band systems and techniques. FIGS. 31-39 and the associated text below describe various broad band systems and techniques that may be utilized in conjunction with the equipment, components, materials, and techniques described above.

Figure 31:
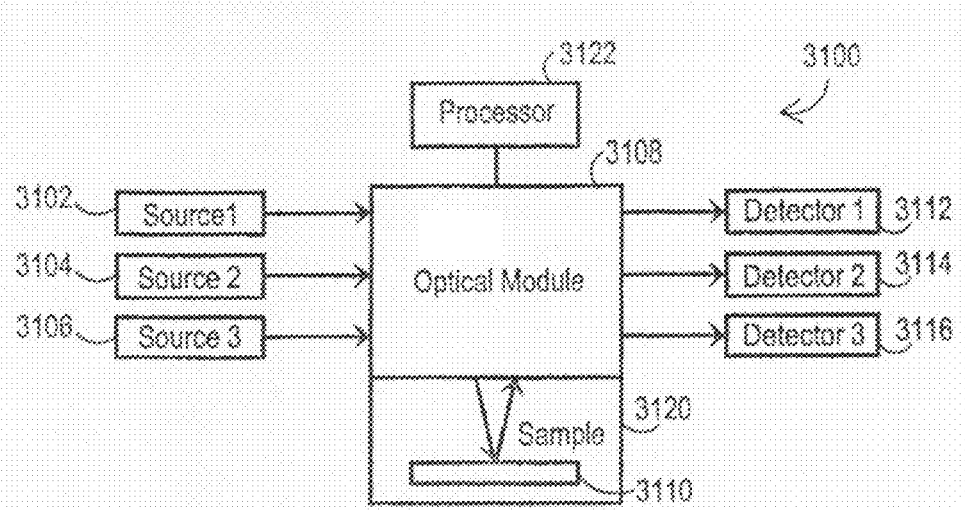
FIG. 31—Schematic representation of broad-band reflectometer with optical module.

A simplified representation of one embodiment of a broad band system 3100 is presented in FIG. 31. In operation, light from one of three sources 3102, 3104, and 3106 is selected, directed and focused by the optical module 3108 onto the surface of the sample 3110. Upon reflection from the sample the light is again collected and directed to one of three detectors 3112, 3114, and 3116, as selected by the optical module 3108. In certain circumstances the optical module may also provide a controlled environment between the sources, sample chamber 3120 and detectors. Additionally, in some cases the optical module may act to improve system performance by providing a means by which collected data is referenced. The optical module is controlled by a processor 3122, which may also be used to analyze data recorded by the detectors.

Figure 32:
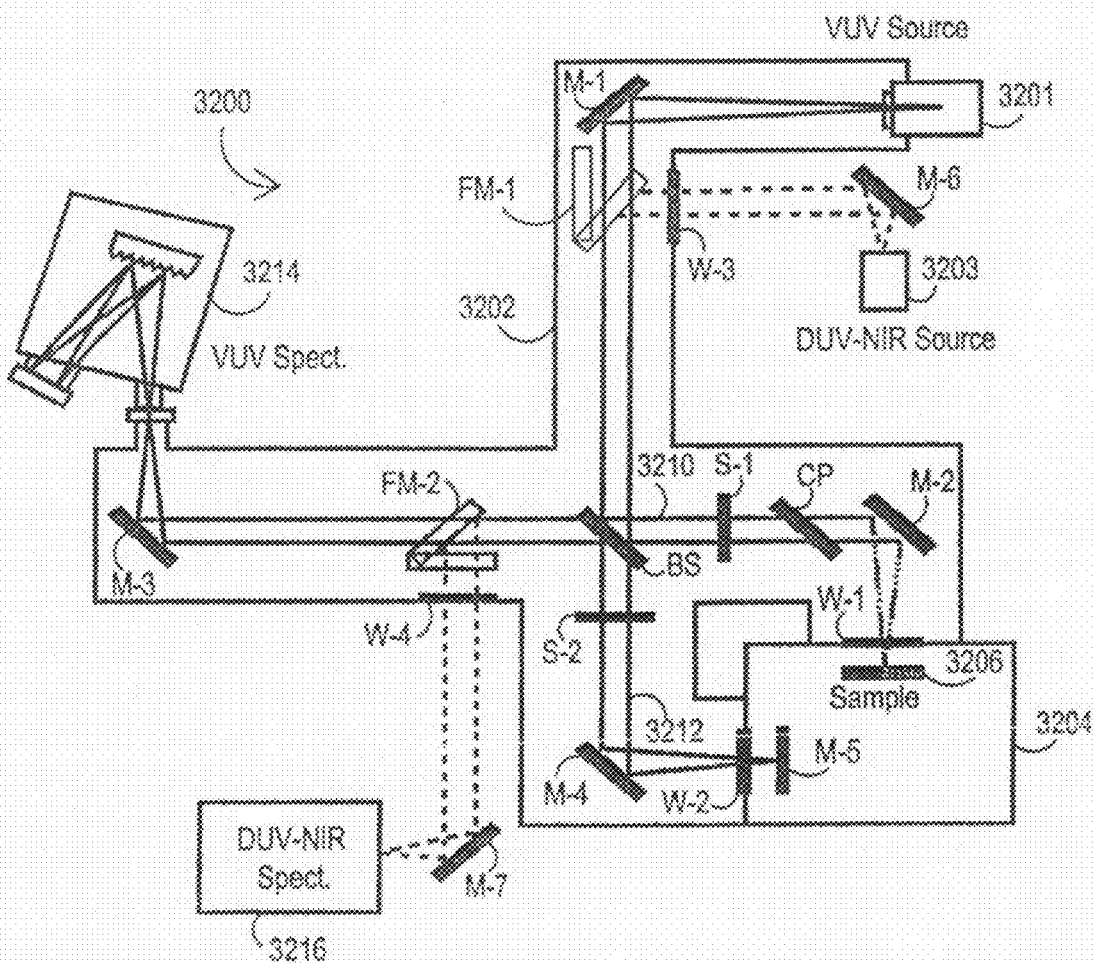
FIG. 32—Broad-band referencing reflectometer covering VUV and DUV-NIR spectral regions.

FIG. 32 presents an embodiment 3200 of the invention configured to collect referenced broad band reflectance data in both the VUV and DUV-NIR. In operation light from these two spectral regions is obtained in a serial manner. That is, reflectance data from the VUV is first obtained and referenced, following which, reflectance data from the DUV-NIR region is collected and referenced. Once both data sets are recorded they are spliced together to form a single broad band spectrum.

The instrument is separated into two environmentally controlled chambers, the instrument chamber 3202 and the sample chamber 3204. The instrument chamber 3202 houses most of the system optics and is not opened to the atmosphere on a regular basis. The sample chamber 3204 houses the sample 3206 and a reference optic mirror M-5 and is opened regularly to facilitate changing samples.

In operation the VUV data is first obtained by switching flip-in source mirror FM-1 into the "out" position so as to allow light from the VUV source 3201 to be collected, collimated and redirected towards beam splitter element BS by focusing mirror M-1. Light striking the beam splitter is divided into two components, the sample beam 3210 and the reference beam 3212, using a balanced Michelson interferometer arrangement. The sample beam is reflected from the beam splitter BS and travels through shutter S-1. Shutter S-2 is closed during this time. The sample beam continues on through compensator plate CP and is redirected and focused into the sample chamber through window W-1 via focusing mirror M-2. The compensator plate is included to eliminate the phase difference that would occur between the sample and reference paths resulting from the fact that light traveling in the sample channel passes through the beam splitter substrate but once, while light traveling in the reference channel passes through the beam splitter substrate three times due to the nature of operation of a beam splitter. Hence, the compensator plate is constructed of the same material and is of the same thickness as the beam splitter. This ensures that light traveling through the sample channel also passes through the same total thickness of beam splitter substrate material. Window W-1 is constructed of a material that is sufficiently transparent to VUV wavelengths so as to maintain high optical throughput in the system as described above.

Light entering the sample chamber 3204 strikes the sample 3206 and is reflected back through W-1 where it is collected, collimated and redirected by mirror M-2. Light from mirror M-2 travels through compensator plate CP, shutter S-1 and beam splitter BS, where it passes unhampered by flip-in detector mirror FM-2 (switched to the "out" position at the same time as FM-1), where it is redirected and focused onto the entrance slit of the VUV spectrometer 3214 by focusing mirror M-3. At this point light from the sample beam is dispersed by the VUV spectrometer and acquired by its associated detector.

Following collection of the sample beam 3210, the reference beam 3212 is measured. This is accomplished by closing shutter S-1 and opening shutter S-2. This enables the reference beam 3212 to travel through beam splitter BS and shutter S-2, wherein it is redirected and focused into the sample chamber through window W-2 via focusing mirror M-4. Window W-2 is also constructed of a material that is sufficiently transparent to VUV wavelengths so as to maintain high optical throughput in the system as described above.

Once inside the sample chamber 3204, light is reflected from the surface of plane reference mirror M-5 and is reflected back towards mirror M-4 where it is collected, collimated and redirected towards beam splitter BS. Light is then reflected by beam splitter BS towards mirror M-3 where it is redirected and focused onto the entrance slit of the VUV spectrometer 3214.

Once both the sample and reference beams are collected a processor (not shown) can be used to calculate the referenced VUV reflectance spectrum.

Following measurement of the VUV data set, the DUV-NIR data is obtained by switching both the source and detector flip-in mirrors, FM-1 and FM-2 respectively, into the "in" position. As a result, light from the VUV source 3201 is blocked and light from the DUV-NIR source 3203 is allowed to pass through window W-3, after it is collected, collimated and redirected by focusing mirror M-6. Similarly, switching flip-in mirror FM-2 into the "in" position directs light from the sample beam 3210 (when shutter S-1 is open and shutter S-2 is closed) and reference beam 3212 (when shutter S-2 is open and shutter S-1 is closed) through window W-4 onto mirror M-7 which focuses the light onto the entrance slit of the DUV-NIR spectrometer 3216 where it is dispersed and collected by its detector. Suitable DUV-NIR spectrometers and detectors are commonplace in today's market. A particularly well-matched combination is manufactured by Jobin Yvon of France. The VS-70 combines a highly efficient (f/2) optical design that does not employ turning mirrors. This instrument has a small physical footprint, incorporates an order sorting filter and can be used with either a linear CCD or PDA detector.

The flip-in mirrors utilized into the system are designed such that they are capable of switching position quickly and in a repeatable fashion in order to minimize losses in optical throughput associated with errors in beam directionality. A particularly well suited motorized flip-in mirror is manufactured by New Focus of the United States. In a slightly modified embodiment, these mirrors could be replaced altogether by beam splitter/shutters pairs; however this would be accompanied by an undesirable loss in VUV signal strength.

Once both the sample and reference beams are obtained the processor is used to calculate the referenced DUV-NIR reflectance spectrum. In this manner, referenced reflectance data is serially obtained in the VUV and DUV-NIR spectral regions. It is noted that both the VUV and DUV-NIR spectrometers need be equipped with necessary sorting filters to avoid complications due to higher order diffraction components.

As vacuum compatible components are typically more complicated to design and expensive to manufacture than their standard counterparts, it follows that system elements not critical to VUV operation be mounted outside the controlled environment. Hence, the DUV-NIR source 3203 and spectrometer/detector 3216 are mounted outside the controlled environment. Such an arrangement is not required however.

Figure 33:
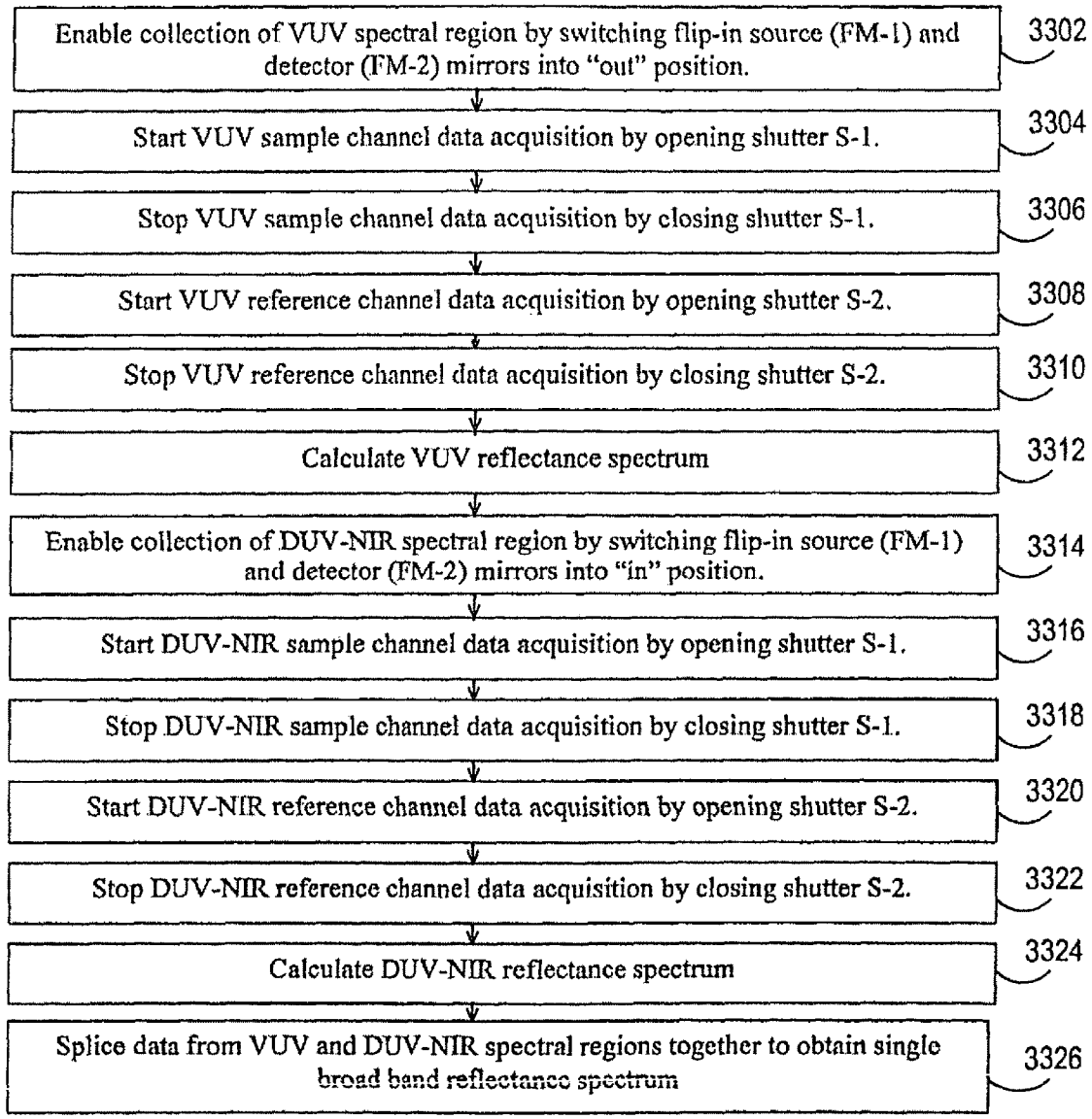
FIG. 33—Serial measurement flowchart for broad-band referencing reflectometer covering VUV and DUV-NIR spectral regions.

A flowchart 3300 summarizing the serial collection process associated with the operation of this embodiment of the invention is presented in FIG. 33. More particularly, as shown in step 3302, the system first enables collection of a VUV spectral region by switching flip-in source (FM-1) and detector (FM-2) mirrors into the "out" position. Then in step 3304, the system starts VUV sample channel data acquisition by opening shutter S-1. Further, in step 3306, VUV sample channel data acquisition is stopped by closing shutter S-1. Then in step 3308, VUV reference channel data acquisition is started by opening shutter S-2. Next in step 3310, VUV reference channel data acquisition is stopped by closing shutter S-2. Further in step 3312, the VUV reflectance spectrum is calculated. Then, in step 3314, collection of the DUV-NIR spectral region is enabled by switching flip-in source (FM-1) and detector (FM-2) mirrors into "in" position. Next, in step 3316 the DUV-NIR sample channel data acquisition is started by opening shutter S-1. Then in step 3318 DUV-NIR sample channel data acquisition is stopped by closing shutter S-1. Then in step 3320 the DUV-NIR reference channel data acquisition is started by opening shutter S-2. Next in step 3322, DUV-NIR reference channel data acquisition is stopped by closing shutter S-2. Further in step 3324, DUV-NIR reflectance spectrum is calculated. Then in step 3326, data from VUV and DUV-NIR spectral regions is spliced together to obtain single broad band reflectance spectrum.

There are many benefits afforded by this embodiment of the invention. For example, the system has been optimized for efficient and accurate VUV performance. Among other things this requires that the environment containing the optical path traversed by the VUV photons be controlled such that concentrations of absorbing species like oxygen and moisture are maintained at sufficiently low levels so as to permit adequate optical throughput. This may be achieved in a variety of ways as described in more detail above. Such techniques include purging the environment with a non-absorbing gas and/or through evacuation via a vacuum system, depending on the level of system performance required.

During acquisition of the VUV data, the flip-in source and detector mirrors are switched to the "out" position and therefore do not contribute any mechanical uncertainty to the measurement. In fact, there are no moving optical elements involved in the acquisition of the VUV data (aside from the shutters). This is advantageous for multiple reasons. Firstly, short wavelength VUV measurements are typically more challenging to perform than those in other wavelength regions due to the low photon flux available and general shortage of efficient optics and coatings that can be employed. Secondly, characterization of ultra-thin (<100 Å) films relies heavily on accurate intensity or amplitude information, since reflectance spectra from such films do not generally exhibit distinct spectral features related to interference effects as do spectra from their thicker film counterparts.

Another benefit afforded by this embodiment is that it provides a fast and automated means of referencing collected data sets such that highly repeatable results are achieved. This capability acts to reduce or altogether remove errors introduced by changes in the optical throughput of the system. At longer wavelengths such changes are typically driven by variations in source output, while in the VUV changes in the concentrations of absorbing species in the environment of the optical path are expected to dominate.

A further benefit afforded by this embodiment of the invention relates to use of the single optical delivery/collection module. This common module acts to facilitate the collection of data from the same location on the sample using the same spot size and orientation regardless of the spectral region investigated. To this end, the DUV-NIR source and spectrometer are selected such that they maintain substantially similar light gathering/delivery characteristics to those of the VUV source and spectrometer. This aspect of the system is particularly important in situations where patterned samples are under study.

Additionally, the single optical module simplifies alignment of the instrument during integration and manufacturing, particularly with respect to complications arising from auto-focusing routines.

A further benefit afforded by the invention arises from its serial method of operation. Stray light generated through scattering processes may be problematic since it cannot be simply referenced out and can thus lead to non-linear system response and inaccuracies in the recorded reflectance data. By collecting and referencing data from each of the wavelength regions sequentially, the intensity of scattered photons recorded at the detector can be significantly reduced. This follows since only light from one source propagates through the system at any given time. Hence, light from other spectral regions cannot scatter and lead to spurious signals recorded at the detector. This is particularly advantageous when working in the VUV wavelength region, as scattering mechanisms play a much larger role than at longer wavelengths.

Figure 34:
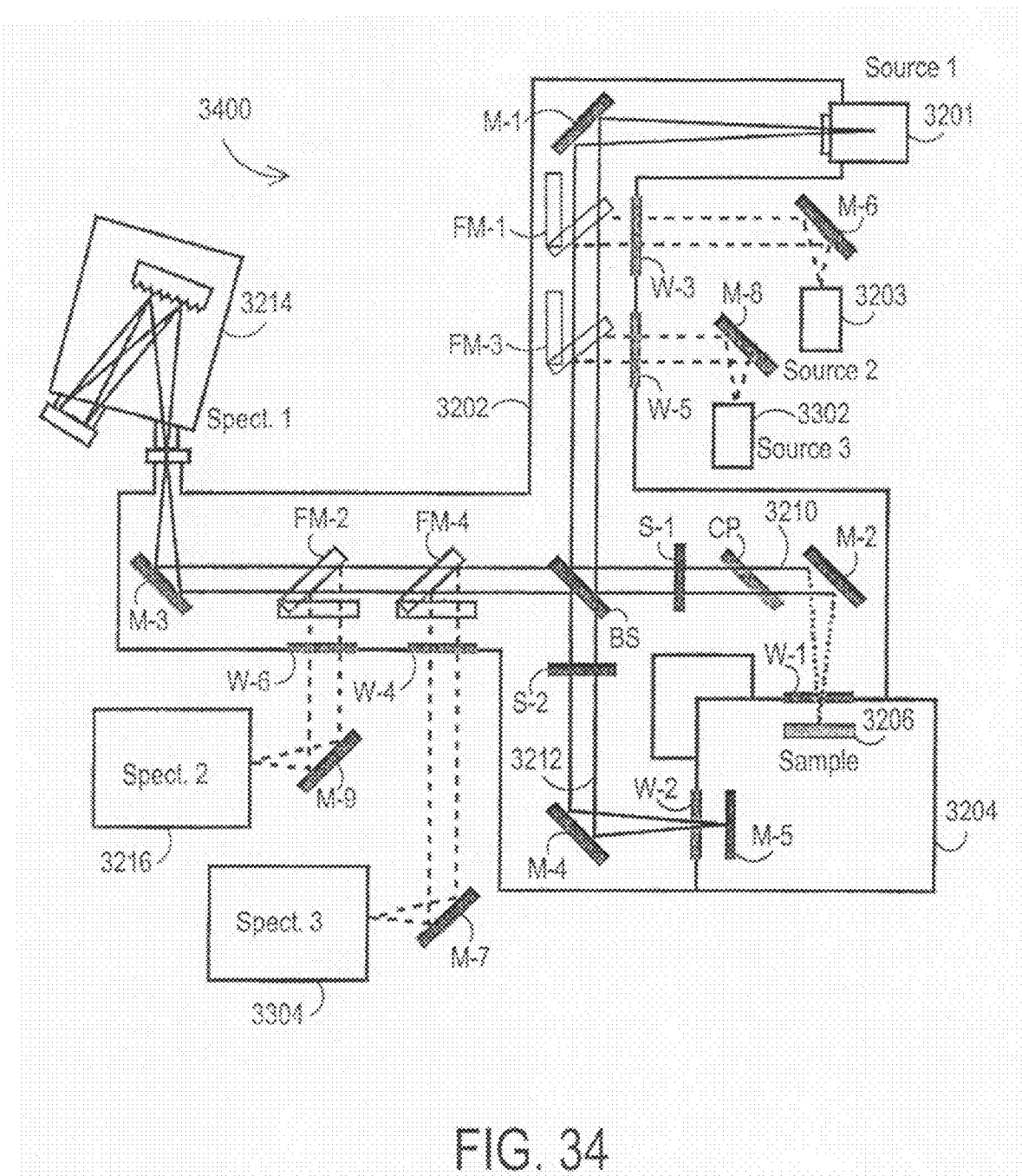
FIG. 34—Broad-band referencing reflectometer covering three spectral regions.

The broad band system and techniques described above can be readily extended to encompass other spectral regions simply through the addition of alternate sources, spectrometers and detectors. FIG. 34 presents an alternate broad band system 3400 in one embodiment of the invention optimized for operation in a first spectral region and designed to perform well in second and third spectral regions. For example, in addition to sources 3201 and 3203 such as shown in FIG. 32, a third source 3302 may be utilized. In one embodiment, the source 3201 may be a VUV source, the source 3203 may be a DUV source and the source 3302 may be a NIR source. Corresponding VUV spectrometer 3214, DUV spectrometer 3216 and NIR spectrometer 3304 may be utilized with the respective associated source. As before, sets of source and detector flip-in mirrors are used to deliver light from alternate sources and to alternate spectrometers and detectors. In this embodiment first spectral region data is collected with all flip-in mirrors (FM-1, FM-2, FM-3, and FM-4) in the "out" position, second spectral region data is collected utilizing source 3203 with only flip-in mirrors FM-1 and FM-2 switched to the "in" position and third spectral region data is collected utilizing source 3302 with only FM-3 and FM-4 switched to the "in" position.

Figure 35:
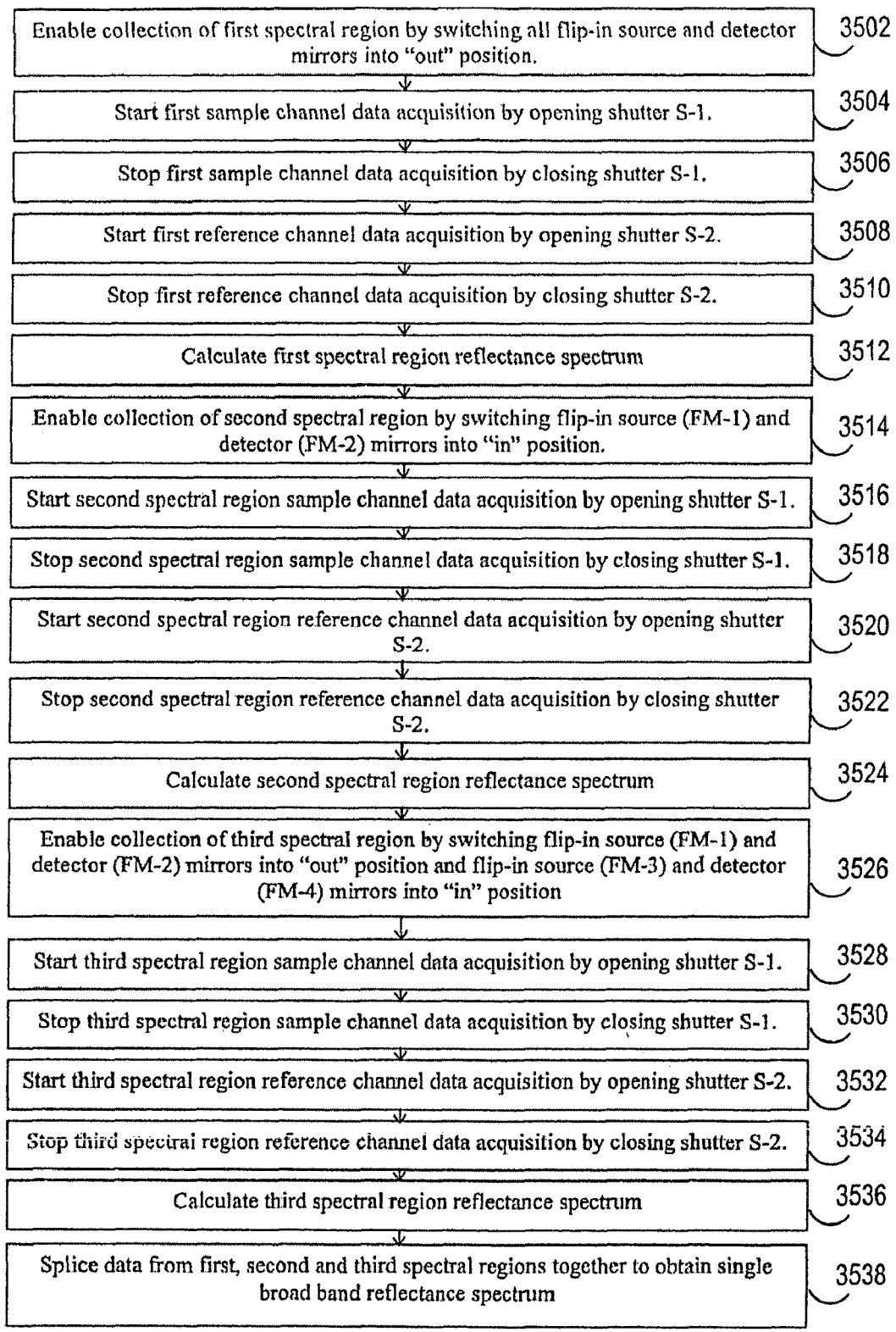
FIG. 35—Serial measurement flowchart for broad-band referencing reflectometer covering three spectral regions.

A flowchart 3500 of the serial measurement process for this embodiment is presented in FIG. 35. More particularly, as shown in step 3502, collection of the first spectral region is enabled by switching all flip-in source and detector mirrors into the "out" position. Then in step 3504, a first sample channel data acquisition is started by opening shutter S-1. Next, in step 3506 the first sample channel data acquisition is stopped by closing shutter S-1. Further in step 3508, the first reference channel data acquisition is started by opening shutter S-2. Then in step 3510, the first reference channel data acquisition is stopped by closing shutter S-2. Then in step 3512, the first spectral region reflectance spectrum is calculated. Further in step 3514, collection of the second spectral region is enabled by switching flip-in source (FM-1) and detector (FM-2) mirrors into the "in" position. Next in step 3516, the second spectral region sample channel data acquisition is started by opening shutter S-1. Next in step 3518, the second spectral region sample channel data acquisition is stopped by closing shutter S-1. Then in step 3520, the second spectral region reference channel data acquisition is started by opening shutter S-2. Next in step 3522, the second spectral region reference channel data acquisition is stopped by closing shutter S-2. Further in step 3524, the second spectral region reflectance spectrum is calculated. Then in step 3526, collection of the third spectral region is enabled by switching flip-in source (FM-1) and detector (FM-2) mirrors into the "out" position and flip-in source (FM-3) and detector (FM-4) mirrors into the "in" position. Then in step 3528, the third spectral region sample channel data acquisition is started by opening shutter S-1. Next in step 3530, the third spectral region sample channel data acquisition is stopped by closing shutter S-1. Next in step 3532, the third spectral region reference channel data acquisition is started by opening shutter S-2. Further in step 3534, the third spectral region reference channel data acquisition is stopped by closing shutter S-2. Then in step 3536, the third spectral region reflectance spectrum is calculated. Next in step 3538, data from the first, second and third spectral regions is spliced together to obtain a single broad band reflectance spectrum.

Figure 36:
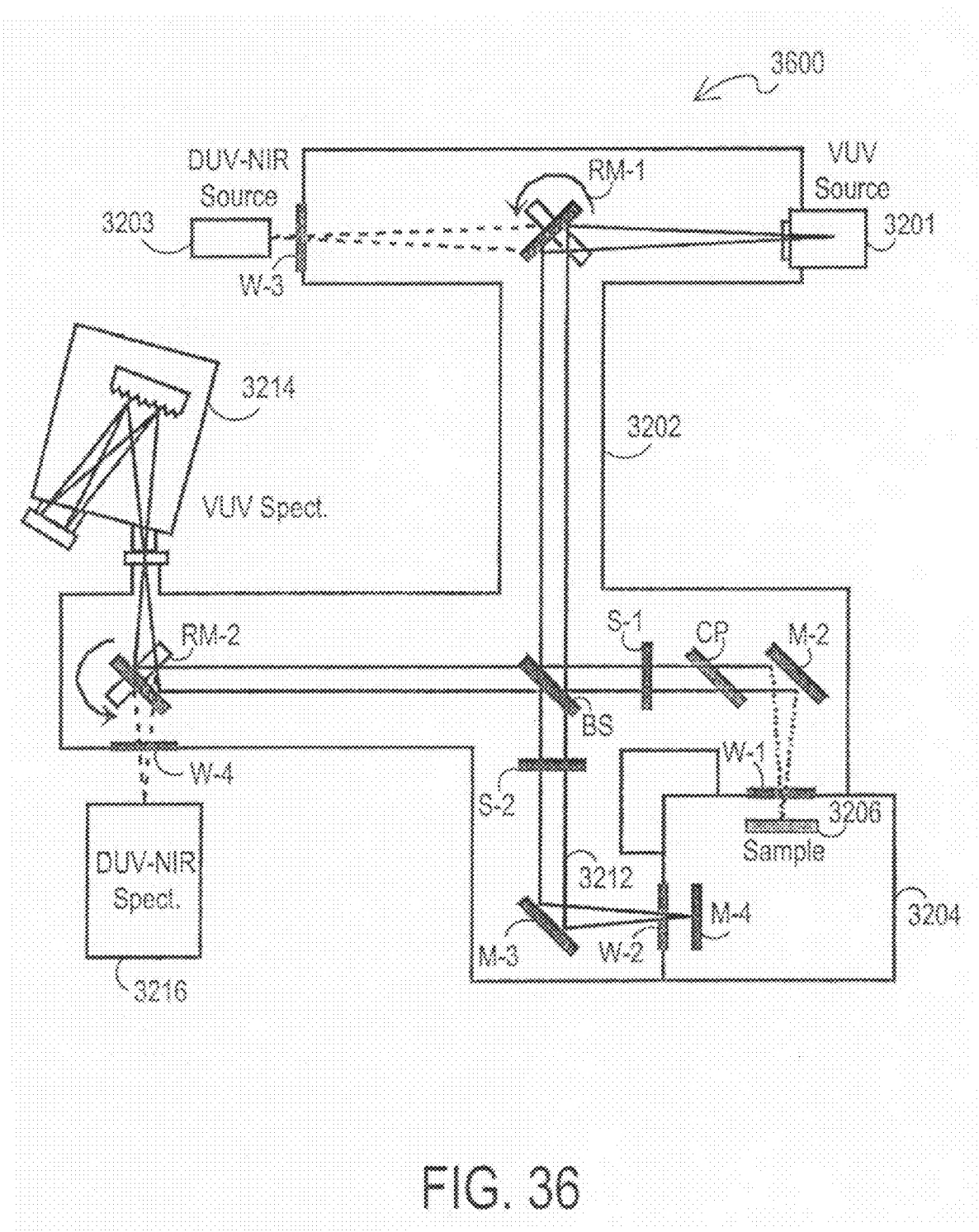
FIG. 36—Alternate embodiment of broad-band referencing reflectometer using rotating mirrors and covering VUV and DUV-NIR spectral regions.

An alternate broad band system 3600, in one embodiment of the invention, is presented in FIG. 36 wherein the selection of sources 3201 and 3203 and spectrometers 3214 and 3216 is accomplished through the rotation of focusing optics RM-1 and RM-2, rather than through use of flip-in mirrors. In this embodiment RM-1 and RM-2 are off-axis parabolic mirrors with a turning angle of 900. Hence, RM-1 can be rotated about the optical axis defined by the line joining RM-1 and beam splitter BS in order to collect light from either the VUV source 3201 or DUV-NIR source 3203. Similarly, focusing mirror RM-2 can be rotated about the axis defined by the line between RM-2 and BS in order to focus light onto the entrance slit of either the VUV spectrometer 3214 or DUV-NIR spectrometer 3216.

This arrangement utilizes fewer optical components than that of the embodiment of FIG. 32 and hence, may render a smaller instrumental footprint. A potential drawback to this approach is that it does introduce some degree of mechanical uncertainty into the VUV measurement process due to the rotation of focusing optics RM-1 and RM-2.

Figure 37:
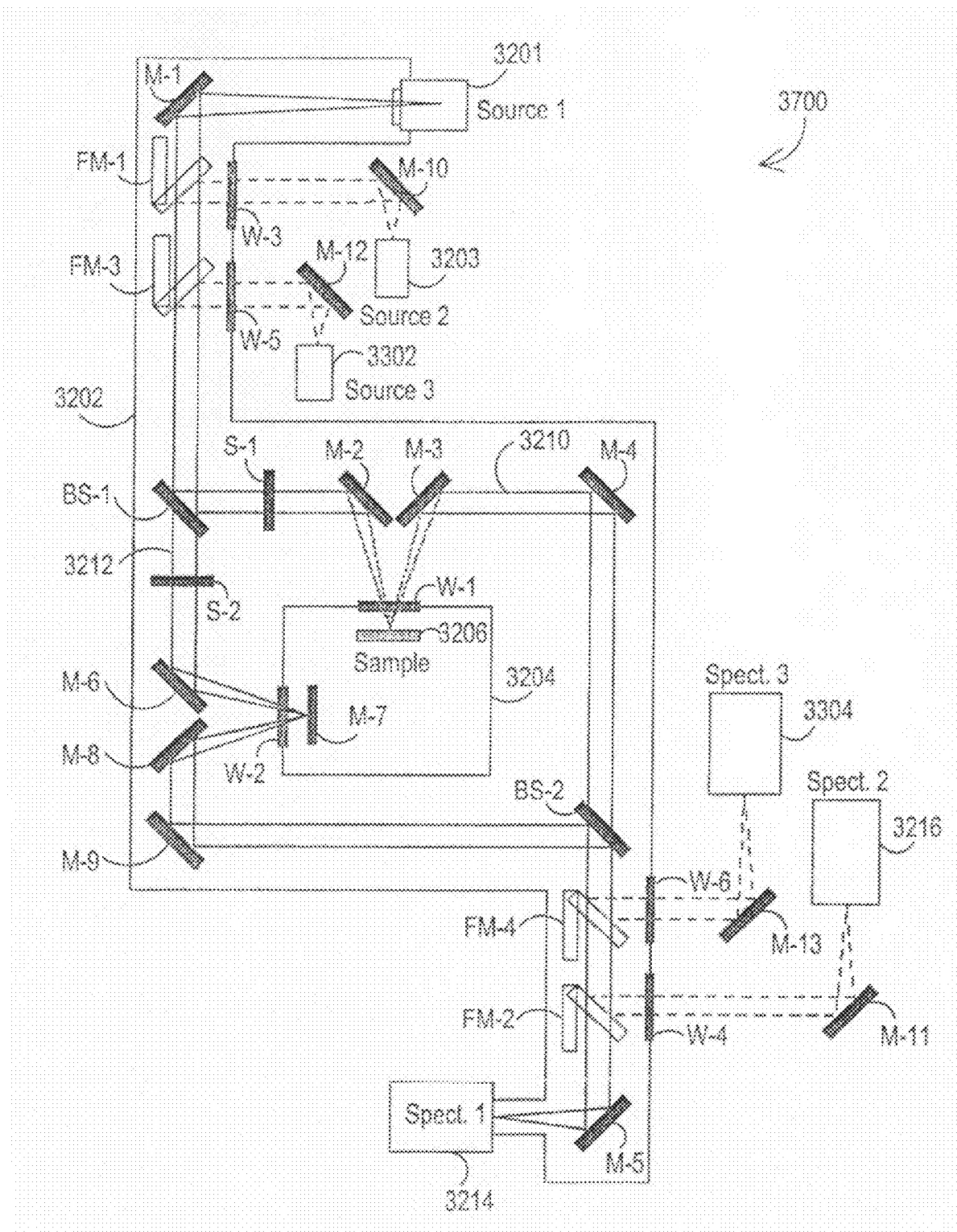
FIG. 37—Alternate embodiment of broad-band referencing reflectometer covering three spectral regions.

An alternate embodiment of the invention is presented in FIG. 37 with regard to system 3700 wherein the balanced interferometer employed in the referencing channel 3212 is of the Mach-Zehnder type rather than the Michelson configuration depicted in the embodiments of FIG. 32, FIG. 34 and FIG. 36. This embodiment requires additional optical elements but provides greater flexibility with respect to the angular delivery and collection of light to and from the surface of sample 3206.

In operation, light from the first source 3201 is collected, collimated and re-directed by focusing mirror M-1 towards beam splitter BS-1 where it is divided into sample beam 3210 and reference beam 3212 components. The sample beam 3210 is enabled when shutter S-1 is open and shutter S-2 is closed. In this state light reflected from beam splitter BS-1 is collected and focused onto the sample through window W-1 by focusing mirror M-2. Light reflected from the sample 3206 exits the sample chamber 3204 via window W-1 and is collected, collimated and redirected by focusing mirror M-3 towards plane mirror M-4. Light leaving mirror M-4 travels through the second beam splitter BS-2 and is collected and focused onto the entrance slit of the first spectral region spectrometer 3214 by focusing mirror M-5. At this point light from the sample beam 3210 is dispersed by the spectrometer and acquired by the detector.

Following collection of the first spectral region sample beam, the first spectral region reference beam is measured. This is accomplished by closing shutter S-1 and opening shutter S-2. This allows the reference beam 3212 to travel through beam splitter BS-1, wherein it is redirected and focused into the sample chamber 3204 through window W-2 via focusing mirror M-6. Once inside the sample chamber 3204 light is reflected from the surface of plane reference mirror M-7 and is collected, collimated and redirected towards plane mirror M-9 by focusing mirror M-8. This light is reflected by beam splitter BS-2, and is redirected and focused onto the entrance slit of the first spectral region spectrometer 3214 by focusing mirror M-5. Once both the sample and reference beams are obtained the referenced reflectance data for the first spectral region is calculated using a processor (not shown).

Data from the second and third spectral regions are again collected using sets of source and detector flip-in mirrors to deliver light from alternate sources and to alternate spectrometers and their associated detectors. Specifically, second spectral region data is collected when only flip-in mirrors FM-1 and FM-2 are switched to the "in" position and third spectral region data is collected when only FM-3 and FM-4 are switched to the "in" position.

Figure 38:
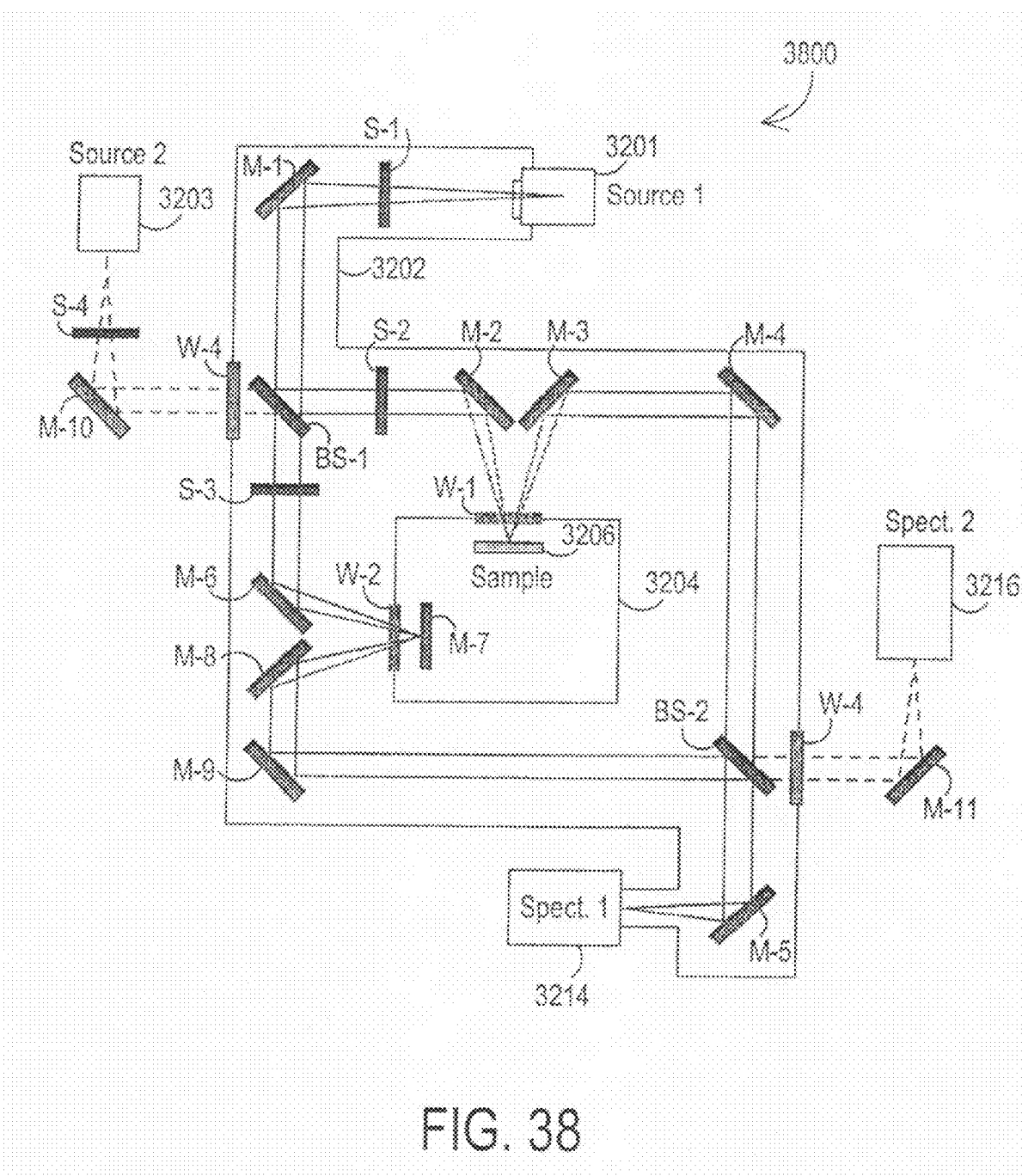
FIG. 38—Alternate embodiment of broad-band referencing reflectometer without flip-in mirrors and covering two spectral regions.

Yet another embodiment of the invention is presented as system 3800 in FIG. 38. This dual spectral region configuration also incorporates a Mach-Zehnder interferometer referencing system but does not require the use of flip-in mirrors to select between spectral regions. Instead, two additional source shutters (S-1 and S-4) have been added to the system to accomplish this task. When measurements of the first spectral region are performed shutter S-1 is open and shutter S-4 is closed. Conversely, when second spectral region measurements are performed shutter S-1 is closed and S-4 is open.

As this embodiment does not utilize flip-in mirrors it follows that system repeatability could to some extent be improved relative to the previously described embodiments since mechanical positioning errors associated with the flip-in mirrors have been removed.

Figure 39:
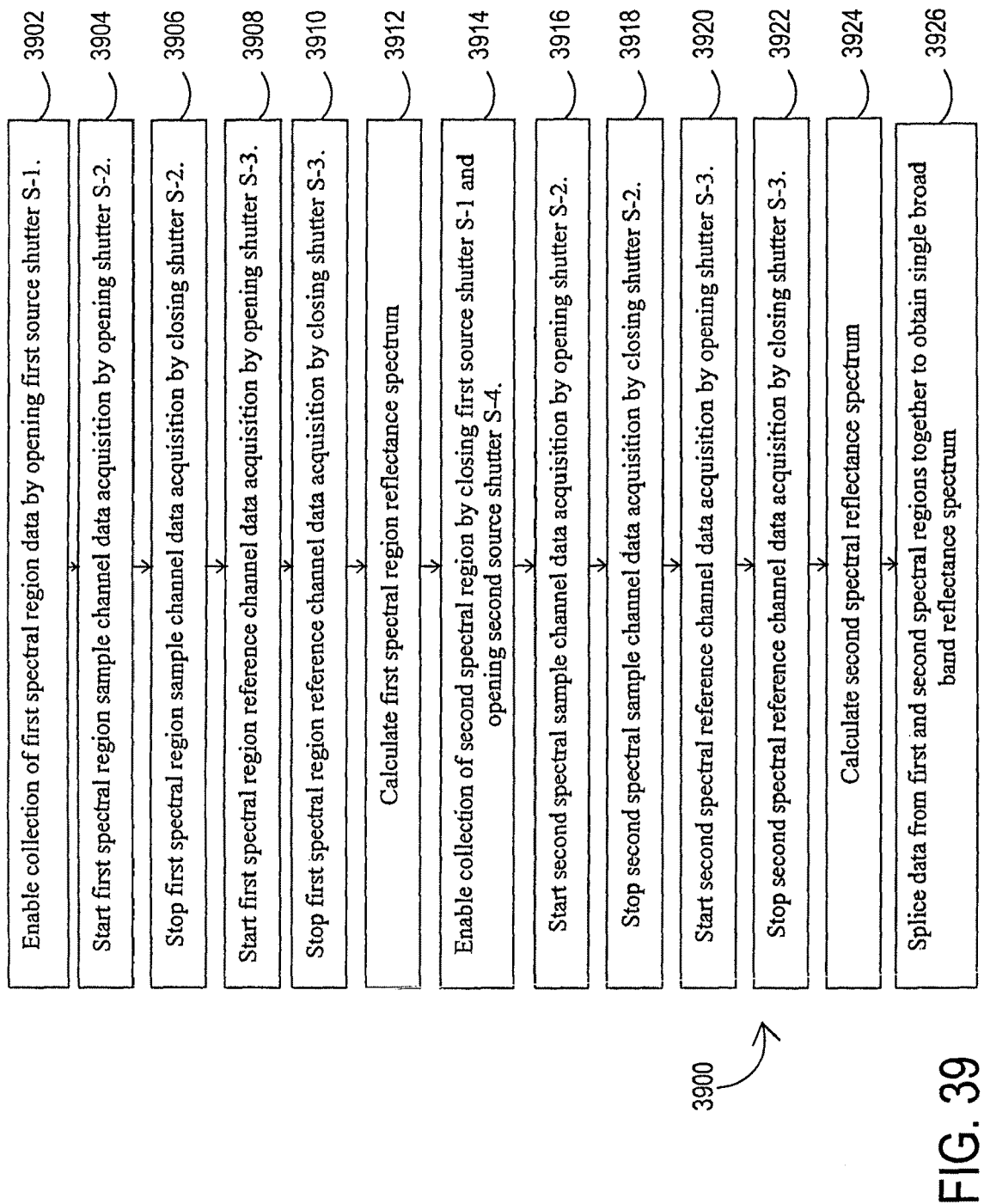
FIG. 39—Serial measurement flowchart for broad-band referencing reflectometer without flip-in mirrors and covering two spectral regions.

A flowchart 3900 of the serial measurement process for the embodiment of FIG. 38 is presented in FIG. 39. More particularly, as shown in step 3902, collection of the first spectral region data is enabled by opening first source shutter S-1. Then in step 3904, the first spectral region sample channel data acquisition is started by opening shutter S-2. Next in step 3906, the first spectral region sample channel data acquisition is stopped by closing shutter S-2. Then in step 3908, the first spectral region reference channel data acquisition is started by opening shutter S-3. Further in step 3910, the first spectral region reference channel data acquisition is stopped by closing shutter S-3. Then in step 3912, the first spectral region reflectance spectrum is calculated. Next in step 3914, collection of the second spectral region is enabled by closing first source shutter S-1 and opening second source shutter S4. Then in step 3916, the second spectral sample channel data acquisition is started by opening shutter S-2. Next in step 3918, the second spectral sample channel data acquisition is stopped by closing shutter S-2. Further in step 3920, the second spectral reference channel data acquisition is started by opening shutter S-3. Then in step 3922, the second spectral reference channel data acquisition is stopped by closing shutter S-3. Next in step 3924, the second spectral reflectance spectrum is calculated. Then in step 3926, data from the first and second spectral regions is spliced together to obtain a single broad band reflectance spectrum.

Thus, as described above broad band systems are provided that may be optimized for operation in a first spectral region and capable of performing well in at least one other spectral region. Common delivery and collection optics in an optical module enable measurements in separate spectral regions to be collected using similar spot properties. For example, similar spot sizes for collection from the sample may be obtained. Further the orientation of the collection spot may be substantially similar between the different spectral regions. Furthermore, the systems and techniques described allow for a serial data collection approach whereby data from separate spectral regions is collected sequentially to avoid stray light complications. The systems may be designed such that no moving optical elements (apart from shutters) are involved in the collection of data from the first spectral region. Additionally, the systems may incorporated an optical module which presents selectable sources and detectors optimized for separate spectral regions. The optical module may also provide a mechanism for quickly referencing measured data so as to ensure that highly repeatable results are achieved.

The broad band systems and techniques described above accordingly provide a metrology system that allows for the accurate collection of optical metrology data from a sample over multiple spectral ranges. By having a optical data for a wide range of wavelengths, fitting algorithms employed by a user of the instrument may achieve faster convergence and more accurate results by taking full advantage of the higher level of constraint afforded by a data set comprised of two or more spectral regions.

When the optical data is collected for multiple spectral regions as described above, the data may be combined in a computer, processor or the like to form a continuous set of data that may be analyzed. The data may be combined in a wide range of manners and, ideally, the data from each spectrometer would match at the point where the spectral regions join. For example, predetermined wavelengths may be selected to determine which spectrometer will be utilized to collect data for particular wavelengths. For example, for wavelengths below 190 nm data may be taken solely from the VUV spectrometer and for wavelengths greater than 190 the data may be taken from a DUV-NIR spectrometer. However, such an approach may cause discontinuities in the collected data at the wavelength crossover point if the results vary from each spectrometer at the crossover point. Such variations may complicate fitting algorithms and the processing of the data. In another approach, the wavelength for which data is collected from each spectrometer may overlap for some determined range, for example 20 nm. In this overlap region, the data for each wavelength may be calculated as an average from each spectrometer. In yet another alternative graded averages or best fit algorithms could be applied to join the data. Any other suitable approach that combines the data from each spectral region may also be utilized.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as presently preferred embodiments. Equivalent elements may be substituted for those illustrated and described herein and certain features of the invention may be utilized independently of the use of other features, all as would be apparent to one skilled in the art after having the benefit of this description of the invention.

What is claimed is:

1. A method for analyzing a scattering or diffracting structure that includes a pattern having a pitch, the method comprising:
providing a below deep ultra-violet (DUV) wavelength reflectometer configured for normal incidence operation and having a light source that provides at least below DUV wavelength light, including vacuum ultra-violet (VUV) wavelengths at and below the pitch of the pattern;
obtaining reflectance data from the scattering or diffracting structure, including reflectance data for the VUV wavelengths; and
utilizing the reflectance data to obtain dimension information of the pattern.

2. The method of claim 1, further comprising utilizing referencing to account for system and environmental changes to adjust reflectance data obtained through use of the reflectometer.

3. The method of claim 1, wherein the reflectometer utilizes a non-polarizing optical path such that a polarization independent measurement may be obtained.

4. The method of claim 1, wherein the below DUV wavelength light is non-polarized at a point in an optical path of the reflectometer at which the scattering or diffracting structure is located.

5. The method of claim 1, wherein the dimension information comprises at least one of line width, sidewall angle, line height, trench depth, trench width and film thickness.

6. The method of claim 1, wherein scatterometry techniques are utilize to determine the dimension information.

7. The method of claim 6, wherein rigorous coupled wave analysis techniques are utilized to determine the dimension information.

8. A method for analyzing a scattering or diffracting structure, comprising:
providing a below deep ultra-violet (DUV) wavelength referencing reflectometer, comprising a source beam channel configured for normal incidence operation and having a non-polarizing optical system that provides at least below deep ultra-violet wavelength light, and comprising a reference beam channel that is balanced with the source beam channel; and
utilizing scatterometry techniques for obtaining dimensional information of the scattering or diffracting structure.

9. The method of claim 8, further comprising utilizing referencing to account for system and environmental changes to adjust reflectance data obtained through use of the reflectometer.

10. The method of claim 9, wherein the dimension information comprises at least one of line width, sidewall angle, line height, trench depth, trench width and film thickness.

11. The method of claim 8, wherein the dimension information comprises at least one of line width, sidewall angle, line height, trench depth, trench width and film thickness.

12. The method of claim 8, wherein rigorous coupled wave analysis techniques are utilized to determine the dimension information.

13. A scatterometry method to determine dimensional information of a patterned structure having a pitch, the method comprising:
providing a reflectometer that utilizes at least in part below deep ultra-violet (DUV) wavelength light, including vacuum ultra-violet (VUV) wavelengths at and below the pitch;
obtaining reflectance data from the scattering or diffracting structure, including reflectance data for at least some of the VUV wavelengths; and
utilizing scatterometry techniques to analyze the reflectance data to obtain dimension information of the patterned structure.

14. The method of claim 13, wherein the reflectometer utilizes a non-polarizing optical path such that a polarization independent measurement may be obtained.

15. The method of claim 13, wherein the below DUV wavelength light is non-polarized at a point in an optical path of the reflectometer at which the patterned structure is located.

16. The method of claim 13, wherein the dimension information comprises at least one of line width, sidewall angle, line height, trench depth, trench width and film thickness.

17. The method of claim 13, wherein the scatterometry techniques include rigorous coupled wave analysis techniques.

18. A method for analyzing a scattering or diffracting structure, comprising:
    providing a below deep ultra-violet (DUV) wavelength reflectometer configured for normal incidence operation and having a light source that provides at least below DUV wavelength light;
    obtaining reflectance data from the scattering or diffracting structure, including reflectance data for wavelengths below DUV wavelengths; and
    utilizing the reflectance data to obtain dimension information of the scattering or diffracting structure including at least one dimension of 20 Å or less.

19. The method of claim 18, wherein utilizing the reflectance data comprises using a balanced reference beam channel to account for system and environmental changes to adjust the reflectance data.

20. The method of claim 18, wherein utilizing the reflectance data comprises applying scatterometry techniques to determine the dimension information.

* * * * *